(12) United States Patent
Spangenberg et al.

(10) Patent No.: US 11,692,185 B2
(45) Date of Patent: Jul. 4, 2023

(54) ANGIOGENIN EXPRESSION IN PLANTS

(71) Applicant: Agriculture Victoria Services PTY LTD, Bundoora (AU)

(72) Inventors: German Spangenberg, Bundoora (AU); Aidyn Mouradov, Mill Park (AU); Jianghui Wang, Bundoora (AU); Benjamin Graeme Cocks, View Bank (AU); Matthew Knight, Airport West (AU); Matthew McDonagh, Williamstown (AU)

(73) Assignee: Agriculture Victoria Services PTY LTD, Bundoora (AU)

( * ) Notice: Subject to any disclaimer, the term of this patent is extended or adjusted under 35 U.S.C. 154(b) by 0 days.

(21) Appl. No.: 16/820,051

(22) Filed: Mar. 16, 2020

(65) Prior Publication Data
US 2021/0032611 A1  Feb. 4, 2021

Related U.S. Application Data

(63) Continuation of application No. 13/510,511, filed as application No. PCT/AU2010/001543 on Nov. 18, 2010, now abandoned.

(30) Foreign Application Priority Data

Nov. 18, 2009 (AU) ................. 2009905627

(51) Int. Cl.
A01H 6/54 (2018.01)
A01H 6/46 (2018.01)
A01H 6/20 (2018.01)
A01H 6/74 (2018.01)
C12N 9/22 (2006.01)
C12N 15/82 (2006.01)

(52) U.S. Cl.
CPC ........... *C12N 9/22* (2013.01); *C12N 15/8257* (2013.01)

(58) Field of Classification Search
CPC ............................. C12N 9/22; C12N 15/8257
See application file for complete search history.

(56) References Cited

U.S. PATENT DOCUMENTS 4,956,282 A * 9/1990 Goodman ............... C07K 14/57
                                                    435/69.51
2005/0130263 A1 * 6/2005 Havukkala ............. G01H 9/004
                                                    435/69.1

FOREIGN PATENT DOCUMENTS

WO   1990/004414 A1   5/1990
WO    00/20557 A2    4/2000
WO   WO-0020612    *   7/2000 ........... C07K 14/415
WO    01/32714 A1    5/2001
WO   WO2007049829 A1 *  5/2007 ............. C12P 21/02

OTHER PUBLICATIONS

Menkhaus et al. 2004. Consideration for the recovery and recombinant proteins from plants. Biotechnol. Prog. 20: 1001-1014. (Year: 2004).*
Forner et al. 2007. The red fluorescent protein eqFP611: application in subcellular localization tudies in higher plants. BMC Plant Biology. 7:28: 1-12. (Year: 2007).*
Twyman, R. 2004. Host Plants, systems and expression strategies for molecular farming in Molecular Farming. Ed. Fisher & Schilbers. pp. 191-216. (Year: 2004).*
Puigbo et al. 2007. Optimizer: a web server for optimizing the codon usage of DNA sequences. Nucleic Acids Research. vol 35: W126-W131. (Year: 2007).*
Abenes, M. et al. "Transient expression and oil body targeting of an *Arabidopsis* oleosin-GUS reporter fusion protein in a range of oilseed embyros" Plant Cell Reports, 1997, pp. 1-7, vol. 17.
Acharya, K. R. et al., Crystal structure of human angiogenin reveals the structural basis for its functional divergence from ribonuclease, Proc. Natl Academy Sci. USA, 1994, pp. 2915-2919, vol. 91.
Baghdady, A. et al., Eucalyptus gunnii CCR and CAD2 promoters are active in lignifying cells during primary and secondary xylem formation in *Arabidopsis thaliana*, Plant Physiol. Biochem., 2006, pp. 674-683, vol. 44.
Bai, Y. et al., Genetic transformation of elite turf-type cultivars of Tall Fescue, International Turfgrass Society Research Journal, 2001,pp. 129-136, vol. 9.
Bilang, R. et al., The 3'-terminal region of the hygromycin-B-resistance gene is important for its activity in *Escherichia coli* and Nicotiana tabacum, Gene, 1991, pp. 249-250, vol. 100.
Bond, M. D. et al., Isolation of bovine angiogenin using a placental ribonuclease inhibitor binding assay, Biochemistry, 1988, pp. 6282-6287, vol. 27.
Borisjuk, N. et al., Calreticulin expression in plant cells: developmental regulation, tissue specificity and intracellular distribution, Planta, 1998, pp. 504-514, vol. 206.
Chen, Z. et al., A DNA sequence element that confers seed-specific enhancement to a constitutive promoter, EMBO J., 1988, pp. 297-302, vol. 7.
Christensen, A. H. et al., Maize polyubiquitin genes: structure, thermal perturbation of expression and transcript splicing, and promoter activity following transfer to protoplasts by electroporation, Plant Mol Biol., 1992, pp. 675-689, vol. 18.
Daniell, H. et al., Breakthrough in chloroplast genetic engineering of agronomically important crops, Trends in Biotechnology, 2005, pp. 238-245, vol. 23.

(Continued)

*Primary Examiner* — Karen M Redden
(74) *Attorney, Agent, or Firm* — Larson & Anderson, LLC

(57) ABSTRACT

The present invention relates to plant-produced angiogenins, to related plant cells, plant calli, plants, seeds and other plant parts and products derived therefrom and to uses of plant-produced angiogenins.
The present invention also relates to expression of angiogenin genes in plants and to related nucleic acids, constructs and methods.

10 Claims, 52 Drawing Sheets

Figure 12:
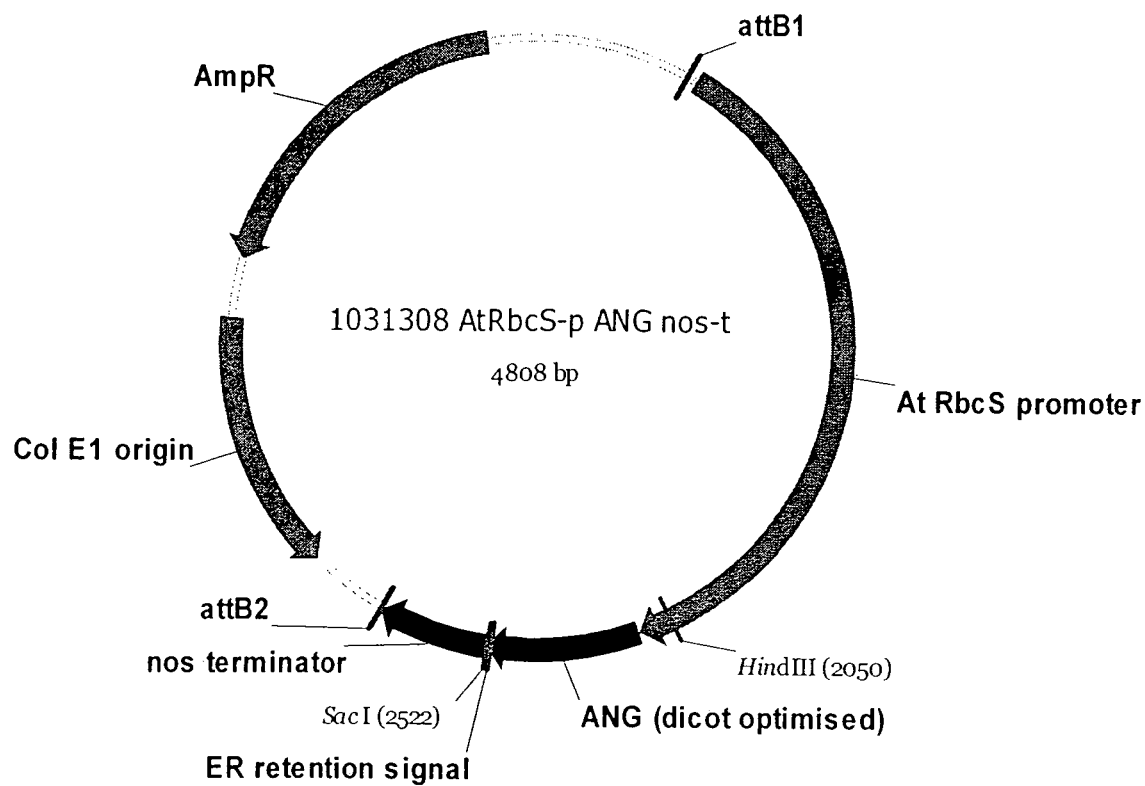

Specification includes a Sequence Listing.

(56) References Cited

OTHER PUBLICATIONS

Denecke, J., et al., Protein secretion in plant cells can occur via a default pathway, Plant Cell, 1990, pp. 51-59, vol. 2.

Doczi, R. et al., Conservation of the drought-inducible DS2 genes and divergences fro their ARS paralogues in solanaceous species, Plant Phys Biochem., 2005, pp. 269-276, vol. 43.

Gao, X. et al., Identification and characterisation of folistatin as a novel angiogenin-binding protein, FEBS Lett., 2007, pp. 5505-5510, vol. 581.

Gao, X., et al., Mechanisms of action of angiogenin, Acta Biochim Biophys. Sin., 2008, pp. 619-624, vol. 40.

Gleba, D. et al., Use of plant roots for phytoremediation and molecular farming, Proc. Natl. Acad. Sci. USA, 1999, pp. 5973-5977, vol. 96.

Hara-Nishimura, I. et al., Diversity and formation of endoplasmic reticulum-derived compartments in plants. Are these compartments specific to plant cells, Plant Physiol, 2004, pp. 3435-3439, vol. 136.

Harper, J. W. et al., Conformational characterization of human angiogenin by limited proteolysis, J Protein Chem., 1988, pp. 355-363, vol. 7.

Hashizume, F. et al., Development and evaluation of transgenic rice seeds accumulating a type II-collagen tolerogenic peptide, Transgenic Res., 2008, pp. 1117-11259, vol. 17.

Hauffe, K. D. et al., Combinatorial interactions between positive and negative cis-acting elements control spatial patterns of 4CL-1 expression in transgenic tobacco, Plant J., 1993, pp. 235-253, vol. 4.

Huang, C. N. et al., Estimating Viability of Plant Protoplasts Using Double and Single Staining, Protoplasma, 1986, pp. 80-87, vol. 135.

Herbers, K. et al., Cloning and characterization of a cathepsin D inhibitor gene from *Solanum tuberosum* L, Plant Mol Biol, 1994, pp. 73-83, vol. 26.

Hu, H. et al., alpha-Actinin-2, a cytoskeletal protein binds to angiogenin, Biochem. Biophys. Res. Commun, 2005, pp. 661-667, vol. 329.

Jamal, A et al. "Role of genetic factors and environmental comditions in recombinant protein production for moelcular farming" Biotechnology Advances, 2009, pp. 914-923, vol. 27.

Jin, L. et al., Molecular cloning, expression profile and promoter analysis of the novel ethylene responsive transcription factor gene GhERF4 from cotton, Plant Phys Biochem., 2008, pp. 46-53, vol. 46.

Kay, R. et al., Duplication of CaMV35S promoter sequences creates a strong enhancer for plant genes, Science, 1987, pp. 1299-1302, vol. 236.

Keller, B. et al., Vascular-Specific Expression of the Bean GRP 1.8 Gene is Negatively Regulated, Plant Cell, 1991, pp. 1051-1061, vol. 3.

Kishimoto, K. et al., Endogenous angiogenin in endothelial cells is a general requirement for cell proliferation and angiogenesis, Oncogene, 2005, pp. 445-456, vol. 24.

Koyama T et al, Promoter of *Arabidipsis thaliana* Phosphate Transporter Gene Drives Root-Specific Expression ofTransgene in Rice, Journal of Bioscience and Bioengineering, 2005, pp. 38-42, vol. 99, No. 1.

Kragler, F. et al., Identification and analysis of the plant peroxisomal targeting signal 1 receptor NtPEX5, Proc. Natl. Acad. Sci. USA, 1998, pp. 13336-13341, vol. 95.

Lamacchia, C. et al., Endosperm-specific activity of a storage protein gene promoter in transgenic wheat seed, J. Exp Bot., 2001, pp. 243-250, vol. 52.

Lebrasseur, N. D. et al., Local and systemic wound-induction of RNase and nuclease activities in *Arabidopsis*: RNS1 as a marker for a JA-independent systemic signaling pathway, The Plant Journal, 2002, pp. 393-403, vol. 2, No. 4.

Lee, W. S., et al., Maize oleosin is correctly targeted to seed oil bodies in *Brassica napus* transformed with the maize oleosin gene, Proc. Natl. Acad. Sci. USA, 1991, pp. 6181-6185.

Lienard, D. et al., Pharmng and transgenic plants, Biotechnology Annual Review, 2007, pp. 115-147, vol. 13.

Lin, K. et al., Generation and analysis of the transgenic potatoes expressing heterologous Thermostable B-amylase, Plant Science, 2008, pp. 649-657, vol. 174.

Liu, D. et al., High transgene expression levels in sugarcane (*Saccharum officinarum* L.) driven by the rice ubiquitin promoter RUBQ2, Plant Science, 2003, pp. 743-750, vol. 165.

Ma, J. K-C., et al., The Production of Recombinant Pharmaceutical Proteins in Plants, Nature Reviews Genetics, 2003, pp. 794-805, vol. 4, No. 10, MacMillan Magazines, GB XP002464355.

Markert, Y. et al., Increased proteolytic resistance of ribonuclease A by protein engineering, Protein Eng., 2001, pp. 791-796, vol. 14.

Marraccini, P., et al., Molecular cloning of the complete 11S seed storage protein gene of Coffea arabica and promoter analysis in transgenic tobacco plants, Plant Physiol Biochem, 1999, pp. 273-282, vol. 37.

Marty, F., Plant Vacuoles, Plant Cell, 1999, pp. 587-600, vol. 11.

McElroy, D. et al., Isolation of an efficient actin promoter for use in rice transformation, Plant Cell, 1990, pp. 163-171, vol. 2.

Murray, E. E. et al., Codon usage in plants, Nucleic Acids Research, 1989, pp. 477-498, vol. 17.

Newton, D. et al., Antitransferrin Receptor Antibody-RNase Fusion Protein Expressed in the Mammary Gland of Transgenic Mice, Journal of Immunological Methods, 1999, pp. 159-167, vol. 231, No. 1-2.

Ouellet, F. et al., The wheat wcs120 promoter is cold-inducible in both monocottyledeonous and dicotelydonous species, FEBS Letters, 1998, pp. 324-328, vol. 423.

Pedersen, K. et al, Cloning and sequence analysis reveal structural variation among related zein genes in maize, Cell, 1982, pp. 1015-1026, vol. 29.

Pizzo, E. et al., Ribonucleases and Angiogenins from Fish, Journal of Biological Chemistry, 2006, pp. 27454-27460, vol. 281, No. 37.

Ramirez, Y. et al., Fruit-Specific Expression of the Human Immunodeficiency Virus Type 1 Tat Gene in Tomato Plants and Its Immunogenic Potential in Mice, Clin Vaccine Immunol., 2007, pp. 685-692.

Romero, H. et al., Expression profile analysis and biochemical properties of the peptide methionine sulfoxide reductase A (PMSRA) gene family in *Arabidopsis*, Plant Science, 2006, pp. 705-714, vol. 170.

Schernthaner, J. P. et al., Endosperm-specific activity of a zein gene promoter in transgenic tobacco plants, EMBO J, 1988, pp. 1249-1255, vol. 7.

Schillberg, S. et al. "Molecular farming of recombinant antibodies in plants" Cellular and Molecular Life Science, 2003, pp. 443-445, vol. 60.

Schouten, A. et al. "The C-Terminal KDEL sequence increases the expression level of a single-chain antibody designed to be targeted to both the cytosol and the secretory pathway in trangenic tobacco" Plant Molecular Biology, 1996, pp. 781-793, vol. 30.

Schunmann, P.H.D., et al., Characterization of promoter expression patterns derived from the Pht1 phosphate transporter genes of barley (*Hordeum vulgare* L.), Journal of Experimental Botany, 2004, pp. 855-865, vol. 55.

Selinger, D. A., et al., The Maize Regulatory Gene B-Peru Contains a DNA Rearrangement That Specifies Tissue-Specific Expression Through Both Positive and Negative Promoter Elements, Genetics, 1998, pp. 1125-1138, vol. 149.

Sharma, A. K. et al., Plants as bioreactors: Recent developments and emerging opportunities, Biotechnology Advances, 2009, pp. 811-832, vol. 27, No. 6, XP027185668, ISSN: 0734-9750, [retreived on Jun. 30, 2009].

Shapiro, R. et al., Human placental ribonuclease inhibitor abolishes both angiogenic and ribonucleolytic activities of angiogenin. Proceedings of the National Academy of Sciences USA, 1987, pp. 2238-2241, vol. 84.

Siebertz, B. et al., cis-Analysis of the wound inducible promoter wun-1 in transgenic tobacco plants and histochemical localization of its expression,The Plant Cell, 1989, pp. 960-968, vol. 1.

(56) References Cited

OTHER PUBLICATIONS

Sojkul, P et al. "A plant signal peptide-hepatitis B surface antigen fusion protein with enhanced stability and immunogenicity expressed in plant cells" 2003, PNAS, pp. 2209-2214, vol. 100, No. 5.

Spangenberg, G. et al., Transgenic tall fescue and red fescue plants fom microprojectile bombardment of embryogenic suspension cells, J Plant Physiol, 1995, pp. 693-701, vol. 145.

Spangenberg, G et al., Transgenic perennial ryegrass (*Lolium perenne*) plants from microprojectile bombardment of embryogenic suspension cells, Plant Sci, 1995, pp. 209-217, vol. 108.

Stark, D. et al., Regulation of the Amount of Starch in Plant Tissues by ADP Glucose Pyrophosphorylase, Science 1992, pp. 287-292, vol. 258.

Szopa, J. et al., Structural organization, expression, and promoter analysis of a 16T isoform of 14-3-3 protein gene from potato, Plant Phys Biochem, 2003, pp. 417-423, vol. 41.

Tran, L. et al., Isolation and functional analysis of *Arabidopsis* stress-inducible NAC transcription factors that bind to a drought-responsive cis-element in the early responsive to dehydration stress 1 promoter, Plant Cell, 2004, pp. 2481-2498, vol. 16.

Twyman, R. M. et al., Molecular farming in plants: host systems and expression technology, Trends in Biotechnlogy, 2003, pp. 570-578, vol. 21, No. 12.

Wan, B. et al, Expression of rice Ca2+-dependent protein kinases (CDPKs) genes under different environmental stresses, FEBS Letters, 2007, pp. 1179-1189, vol. 581.

Yamaguchi-Shinozaki, K. et al., Characterisation of the expression of a desiccation-responsive rd29 gene of *Arabidopsis thaliana* and analysis of its promoter in transgenic plants, Mol. Gen. Genet., 1993, pp. 331-340, vol. 236.

Yang, N.S. et al., Maize sucrose synthase-promoter directs phloem cell-specific expression of GUS gene in transgenic tobacco plants, Proc. Natl. Acad. Sci. US, 1990, pp. 4144-4148, vol. 87.

Ye, X. et al., Transgenic Italian ryegrass (*Lolium multiflorum*) plants from microprojectile bombardment of embryogenic suspension cells, Plant Cell Rep., 1997, pp. 379-384, vol. 16.

Yoon, JM. et al., Cloning and Cytotoxicity of Fusion Proteins of EGF and Angiogenin, Life Science, 1999, pp. 1435-1445, vol. 64, No. 16.

Zhang, X. et al., The indigenous plasmid pQBR103 encodes plant-inducible genes, including three putative helicases, 2004, FEMS Micro. Ecol., 2004, pp. 9-17, vol. 51.

Zhang, H. et al., Interaction between angiogenin and fibulin 1: Evidence and implication, Acta Biochimica et Biophysica Sinica, 2008, pp. 375-380, vol. 40.

Zheng, Jing-Min et al., Recent advance in the investigation of angiopoietin-like protein, Journal of Medical Postgraduates, 2007, pp. 1194-1197, 1201, vol. 20, No. 11.

Zoubenko, O. V. et al., Efficient targeting of foreign genes into the tobacco plastid genome, Nucleic Acids Res., 1994, pp. 3819-3824, vol. 22.

\* cited by examiner

<u>ATGGTCATGGTCCTGAGCCCCCTGTTTTTGGTCTTCATACTGGGTCTGGGTCTGACCCCAGTGGCCCCGGCT</u>CAAGATGA
CTACAGATACATACACTTCCTGACCCAGCACTACGATGCCAAACCAAAGGGCCGGAATGACGAATATTGTTTTAACATGA
TGAAAAATCGACGCCTGACCAGACCTTGCAAAGACCGCAACACCTTTATTCATGGCAACAAGAATGACATTAAGGCCATC
TGTGAGGACAGAAATGGACAGCCTTACAGAGGCGATCTCAGAATAAGCAAGTCTGAATTCCAGATCACCATCTGCAAGCA
TAAAGGAGGTTCCTCCCGGCCTCCATGCCGGTACGGAGCCACAGAAGACTCCAGAGTCATTGTTGTCGGCTGTGAAAATG
GCTTGCCCGTCCACTTTGATGAGTCCTTTATCACTCCACGCCACTAG

FIGURE 1

MVMVLSPLFLVFILGLGLTPVAPAQDDYRYIHFLTQHYDAKPKGRNDEYCFNMMKNRRLTRPCKDRNTFIHGNKNDIKAI
CEDRNGQPYRGDLRISKSEFQITICKHKGGSSRPPCRYGATEDSRVIVVGCENGLPVHFDESFITPRH

FIGURE 2

ATGGTCATGGTCCTGAGCCCCCTGTTCCTGGTCTTCATCCTGGGTCTGGGTCTGACCCCAGTGGCCCCAGCTCAAGATGA
CTACAGATACATCCACTTCCTGACCCAGCACTACGATGCCAAACCAAAGGGCCGGAACGACGAGTACTGCTTCAACATGA
TGAAGAACCGACGCCTGACCAGACCTTGCAAAGACCGCAACACCTTCATCCACGGCAACAAGAACGACATCAAGGCCATC
TGTGAGGACAGAAATGGACAGCCTTACAGAGGCGATCTCAGAATCAGCAAGTCTGAGTTCCAGATCACCATCTGCAAGCA
TAAAGGAGGTTCCTCCCGGCCTCCATGCCGGTACGGAGCCACAGAAGACTCCAGAGTCATTGTTGTCGGCTGTGAGAATG
GCTTGCCCGTCCACTTTGATGAGTCCTTTATCACTCCACGCCACTAG

FIGURE 3

```
Cow       : ATGGTCATGGTCCTGAGCCCCTGTTTTTGGTCTTCATACTGGGTCTGGGTCTGACCCCA   60
Human     : ATGGTGATGGGCCTGGGCGTTTTGTTGTTGGTCTTCGTGCTGGGTCTGGGTCTGACCCCA   60
Gorilla   : ATGGTGATGGGCCTGGGCGTTTTGTTGTTGGTCTTCGTGCTGGGTCTGGGTCTGACCCCA   60
Chimp     : ATGGTGATGGGCCTGGGCGTTTTGTTGTTGGTCTTCGTGCTGGGTCTGGGTCTGACCCCA   60
Monkey    : ATGGTGATGGGCCTGGGCCTTTTCTTGTTGGTCTTCATGCTGGGTCTGGGTCTGACCCCA   60
Horse     : ATGGCGATGAGCCTCTGCCCCTGTTGTTGGTCTTCGTGCTGGGTCTGGGTCTGACCCCA   60
Pig       : ATGGTGATATTGCTCGGCCCCTGCTGTTGGTCTTCATGCTGGGTCTGGGTCTGCCCCCG   60
Rat       : ATGGAGATGAGCCTGCGTCCTCTGTTGTTGGTTTTTGTGCTGGGTCTGGTTTCGACCCCT : 60
Mouse     : ATGGCGATAAGCCCAGGCCCGTTGTTCTTGATCTTCGTGCTGGGTCTGGTTGTCATCCCT : 60
Chicken   : ATGACAATGAGCCCATGTCCTTTGTTGTTGGTCTTCGTGCTGGGTCTGGTTGTCATTCCT : 60

Cow       : GTGGCGCCGGCTCAAGATGACTACAGATACATAGACTTCCTGACCCAGCACTACGATGCC : 120
Human     : CCGACGCCTGGCTCAGGATAACTGCAGGTACACACAGTTCCTGACCCAGCACTATGATGCC : 120
Gorilla   : CCGACGCCTGGCTCAGGATAACTCCAGGTACACACAGTTCCTGACCCAGCACTATGATGCC : 120
Chimp     : CGGACGCCTGGCTCAGGATAACTCCAGGTACACACAGTTCCTGACCCAGCACTATGATGCC : 120
Monkey    : GCCACGCCTGGCTCAGGATAACTCCAGGTACAGACAGTTCCTGACCCAAGCACTATGATGCC : 120
Horse     : CCATCCCTGGCTCAGGATGATTCCAGGTACAGACAGTTCCTGACCAAGCACTATGATGCC : 120
Pig       : CTGAGCCTGGCTAAGGATGAAGACAGGTACACACACTTCCTGACCCAGCACTACGATGCC : 120
Rat       : TCAAGTCTGGCTCAGGACGACCCAGGTACACGAAGTTCCTGACTCAGCACTATGATGCC : 120
Mouse     : CCACTCTGGCTCAGGATGACTCCAGGTACACAAAATTCCTGACTCAGCACCATGACGCC : 120
Chicken   : CCAAGTCTGGCTCACAATGAAG---GGTACGAAAATTCCTACGTCAGCACTATGATGCC : 117

Cow       : AAACCAAAGGGCCGGAATGACGAATATTGTTTTAACATGATGAAAATCGACGCCTGACC   180
Human     : AAACCACAGGGCCGGCATGACAGATACTGTGAAAGCATCATGAGGACACGGGGCCTGACC   180
Gorilla   : AAACCACAGGGCCGGCATGACAGATACTGTGAAAGCATCATGAGGACACGGGGCCTGACC   180
Chimp     : AAACCACAGGGCCGGCATCACAGATACTGTGAAAGCATCATGAGGACACGGGGCCTGACC   180
Monkey    : ACACCACAGGGCCGGAATGACAGATACTGTGAAAGCATGATGAGGACAGCGGGCCTGACC   180
Horse     : AATCCAACGGGGCCGGAATGACAGATACTGTGAAAGCATCATGGTGAGACGACACCTGACC   180
Pig       : AAACCAAAGGGCCGGCATGGCAGATACTGTGAAAGCATAATGAAGCAACGAGGCCTGACC   180
Rat       : AAGCCCAAGGGTCGGCATGCCAGATACTGCGAAAGTATGATGAGGACAAGACGCCTAACC   180
Mouse     : AAGCCAAAGGGCCGGACGACAGATACTGTGAACGTATCATGAAGACAAGAAGCCTAACC   180
Chicken   : AAGCCAAAGGGCCGGACGACAGATACTGTGAAAGTATGATGAAGGAAAAGAAAGCTAACC   177

Cow       : AGACCTTGCAAAGACCGCAACACGTTTATTCATGGCAACAAGAATGACATTAAGGCCATC : 240
Human     : TCACCCTGCAAAGACATCAACACATTTATTCATGGCAACAAGCGCAGCATCAAGGCCATC   240
Gorilla   : TCACCCTGCAAAGACATCAACACATTTATTCATGGCAACAAGCGCAGCATCAAGGCCATC : 240
Chimp     : TCACCCTGCAAAGACATCAACACATTTATTCATGGCAACAAGCGCAGCATCAAGGCCATC : 240
Monkey    : TCACCCTGCAAAGACATCAACACGTTTATTCATGGCAACAGTCGCCACATCAAGGCCATC : 240
Horse     : ACACCCTGCAAAGACACCAACACTTTTATTCATGGCAACAGCAGCAGCATCAAGGCCATC : 240
Pig       : AGACCCTGCAAAGAGGTCAACACGTTTATTCATGGCACGAGCAATGATATCAAGGCCATC : 240
Rat       : TGGCCCTGCAAAGAGGTCAACACGTTTATCCATGGCAACAAGGGCAGCATCAAGGCCATC : 240
Mouse     : TCACCCTGCAAAGATGTCAACACGTTTATCCATGGCAACAAGAGCAACATCAGGCCATC   240
Chicken   : TGGCCTTGCAAAGATGTCAACACCTTTATCCATGGCACCAAGAAAAACATCAGGCCATC : 237
```

FIGURE 4

```
Cow      : TGTGAGGACAGAAATGGACAGCCTTACAGAGGCGATCTCAGAATAAGCAAGTCTGAATTC   300
Human      TGTGAAAACAAGAATGGAAACCCTCACAGAGAAAACCTAAGAATAAGCAAGTCTTGTTTC   300
Gorilla    TGTGAAAACAAGAATGGAAACCCTCACAGAGAAAACCTAAGAATAAGCAAGTCTTGTTTC : 300
Chimp      TGTGAAAACAAGAATGGAAACCCTCACAGAGAAAACCTAAGAATAAGCAAGTCTTGTTTC   300
Monkey     TGTGGAGATGAGAATGGAAACCCTTACGGAGAAAACCTAAGAATAAGCAAGTCTGCTTTC   300
Horse      TGTGGAAATAAGAATGGAAACCCTTACGGAGAAAACTTTAAGAATAAGCAAGCTCGTTTC :.300
Pig        TGTAATGATAAGAATGGAGAGCCTTACAA---CAATTTCAGAAGAAGCAAGTCTGCTTTC   297
Rat        TGTGGCGC---GAATGGAAGCCCTTACGGAGAAAACTTAAGAATAAGCAGTCTGCCTTC   297
Mouse    : TGTGGAGC---GAATGGAAGCCCTTACGGAGAAAACTTAAGAATGAGCAAGTCTGCCTTC   297
Chicken  : TGCGGAAA---GAAAGGAAGCCCTTATGGAGAAAACTTCAGAATAAGCAATTCTGCCTTC   294

Cow        CAGATCACCATCTGCAAGCATAAAGGAGGTTCCTCCGGCCTCCATGCCGGTACGGAGCC   360
Human      CAGGTCACCACTTGCAAGCTACATGGAGGTTCCGCCTGGCCTCCATGCCAGTACGGAGCC . 360
Gorilla    CAGGTCACCACTTGCAAGCTACATGGAGGGTCCGCCTGGCCTCCATGCCAGTACGGAGCC : 360
Chimp      CAGGTCACCACTTGCAAGCTACATGGAGGGTCCGCCTGGCCTCCATGCCAGTACGGAGCC : 360
Monkey     CAGGTCACCACTTGCAACCTACGTGGAGGATCCTCCGGCCTCCATGCCGGTACCGAGCC   360
Horse      CAGGTCACCACTTGCAAGCATGCAGGAGGGTCCCCCGGCCTCCATGCCGATACAGAGCC   360
Pig        CAAATTACCACTTGCAAGCATAAGGGAGGGTCAACCGGCCTCCATGTGGGTACAGGGCC   357
Rat        CAGATCACCACCTGCAAGCATACAGGAGGGTCTCCCGGCCCCCTTGCCGGTACCGAGCC   357
Mouse      CAGGTCACCACTTGCAAGCACACAGGAGGGTCTCCCGGCCTCCATGCCAGTACCGAGCC   357
Chicken    CAGATCACCACTTGTTACGCACTCAGGAGCCGTCTCCCAGGCCTCCATGTGGGTACCGAGCC   354

Cow      : ACAGAAGACTCCAGAGTCATTGTTGTCGGCTGTGAAAATGGCTTGCCCGTCCACTTTGAT : 420
Human      ACAGCGGGGTTCAGAAACGTTGTTGTTGCTTGTGAAAATGGCTTACCTGTCCACTTGGAT : 420
Gorilla    ACAGCGGGGTTCAGAAACGTTGTTGTTGCTTGTGAAAATGGCTTACCTGTCCACTTGGAT : 420
Chimp      ACAGCGGGGTTCAGAAACGTTGTTGTTGCTTGTGAAAATGGCTTACCTGTCCACTTGGAT   420
Monkey     ACAGCAGGGTTCAGAAACATTGTTGTTGCTTGTGAAAATGACCTGCCTGTCCACTTGGAT   420
Horse      ACACCAGGGTTCAGAAGCATTGTCATTGCTTGTGAAAACGGCTTGCCTGTCCACTTTGAT   420
Pig        ACAGCAGGGTTCAGAACCATAGCTGTTGCTTGTGAAAATGGCTTGCCTGTCCACTTTGAT   417
Rat        TGTGCAGGGTTCAGACATGTTGTTATTGCCTGTGAAAATGGCTTGCCTGTCCACTTTGAT   417
Mouse      TGTGCAGGGTTCAGACATGTTGTTATTGCCTGTGAGAATGGCTTGCCCGTCCACTTCGAT   417
Chicken    TTTAAAGATTTCAGATATATTGTTATTGCCTGTGAAGATGGCTGCCCTGTCCACTTCGAT   414

Cow        GAGTCCTTTATCACTGCA-CGCCACTAG   447
Human      CAGTCAATTTTCCGTGGTCCGTAA----   444
Gorilla    CAGTCAATTTTCCGTGGTCCGTAA----   444
Chimp      CAGTCAATTTTCCGTGGTCCGTAA---- : 444
Monkey     CAGTCAATTTTCCGTC---CGTAA----   441
Horse      GAGTCCTTTTTCCGTC---GATAA----   441
Pig        GAGTCCTTTATCATTACA-AGCCAGTA-   443
Rat        GAGTCTTTTATCAGTCTCTAC-------   438
Mouse    : GAGTCATTTTTCAGTCTATAC-------   438
Chicken  : GAGTCTTTTATCAGTCCGTAG-------   435
```

FIGURE 4 (cont.)

```
Cow      : MVMVLSPLFLVFILGLGLTPVAPAQDDYRYIHFLTQHYDAKPKGRNDEYCFNMMKNRRLT :  60
Human    : MVMGLGVLLLVFVLGLGLTPPTLAQDNSRYTHFLTQHYDAKPQGRDDRYCESIMRRRGLT :  60
Chimp    : MVMGLGVLLLVFVLGLGLTPPTLAQDNSRYTHFLTQHYDAKPQGRDHRYCESIMRRRGLT :  60
Gorilla  : MVMGLGVLLLVFVLGLGLTPPTLAQDNSRYTHFLTQHYDAKPQGRDDRYCESIMRRRGLT :  60
Monkey   : MVMGLGLFLLVFMLGLGLTPPTLAQDNSRYRDFLTKHYDATPQGRNDRYCESMMRRRGLT :  60
Horse    : MAMSLCPLLLVFVLGLGLTPPSLAQDDSRYRQFLTKHYDANPRGRNDRYCESMMVRRHLT :  60
Pig      : MVILLGPLLLVFMLGLGLAPLSLAKDEDRYTHFLTQHYDAKPKGRDGRYCESIMKQRGLT :  60
Rat      : MEMSLRPLLLVFVLGLVSTPSTLAQDDPRYTKFLTQHYDAKPKGRDARYCESMMRRRGLT :  60
Mouse    : MAISPGPLFLIFVLGLVVIPPTLAQDDSRYTKFLTQHHDAKPKGRDDRYCERMMKRRSLT :  60
Chicken  : MTMSPCPLLLVFVLGLVVIPPTLAQNEG-YEKFLRQHYDAKPKGRDDRYCESMMKERKLT :  59

Cow      : RPCKDRNTFIHGNKNDIKAICEDRNGQPYRGDLRISKSEFQITICKHKGGSSRPPCRYGA   120
Human    : SPCKDINTFIHGNKRSIKAICENKNGNPHRENLRISKSSFQVTTCKLHGGSPWPPCQYRA   120
Chimp    : SPCKDINTFIHGNKRSIKAICENKNGNPHRENLRISKSSFQVTTCKLHGGSPWPPCQYRA : 120
Gorilla  : SPCKDINTFIHGNKRSIKAICENKNGNPHRENLRISKSSFQVTTCKLHGGSPWPPCQYRA : 120
Monkey   : SPCKDINTFIHGNSRHIKAICGDENGNPYGENLRISKSPFQVTTCNLRGGSSRPPCRYRA : 120
Horse    : TPCKDTNTFIHGSKSSIKAICGNKGNPYGETLRISKTRFQVTTCKHAGGSPRPPCRYRA  : 120
Pig      : RPCKEVNTFIHGTRNDIKAICNDKNGEPYN-NFRRSKSPFQITTCKHKGGSNRPPCGYRA : 119
Rat      : SPCKEVNTFIHGNKGSIKAICG-ANGSPYGENLRITSQSPFQITTCKHTGGSPRPPCRYRA: 119
Mouse    : SPCKDVNTFIHGNKSNIKAICG-ANGSPYRENLRMSKSPFQVTTCKHTGGSPRPPCQYRA : 119
Chicken  : SPCKDVNTFIHGTKKNIRAICG-KKGSPYGENFRISNSPFQITTCTHSGASPRPPCGYRA : 118

Cow      :  TEDSRVIVVGCENGLPVHRDESFITPRH   148
Human    :  TAGFRNVVVACENGLPVHLDQSIFRRP-   147
Chimp    : TAGFRNVVVACENGLPVHLDQSIFRRP-   147
Gorilla  : TAGFRNVVVACENGLPVHLDQSIFRRP-   147
Monkey   : TAGFRNIVVACENDLPVHLDQSIFRP--   146
Horse    : TPGFRSIVIACENGLPVHRDESFERP--   146
Pig      : TAGFRTIAVACENGLPVHRDESFIITSQ   147
Rat      : SAGFRHVVIACENGLPVHRDESFISL--   145
Mouse    : SAGFRHVVIACENGLPVHRDESFFSL--   145
Chicken  : FKDFRYIVIACEDGWPVHRDESFISP-- : 144
```

FIGURE 5

```
ATGCAGGACGACTACCGCTACATCCACTTTCTCACCCAGCACTACGACGCCAAGCCAAAGGGCCGCAACGACGAGTACTG
CTTCAACATGATGAAGAACCGCCGCCTCACCCGCCCATGCAAGGACCGCAACACCTTCATCCACGGCAACAAGAACGACA
TCAAGGCCATCTGCGAGGACCGCAACGGCCAGCCATACAGGGGCGACCTCCGCATCTCCAAGTCCGAGTTCCAGATCACC
ATCTGCAAGCACAAGGGCGGCTCCTCCCGCCCACCATGCAGGTACGGCGCCACCGAGGACTCCCGCGTGATCGTGGTGGG
CTGCGAGAACGGCCTCCCAGTGCACTTCGACGAGTCCTTCATCACCCCACGCCACTGA
```

FIGURE 6

```
ATGCAGGACGACTACCGTTACATCCATTTCTTGACTCAGCACTACGACGCTAAGCCTAAGGGAAGAAACGATGAGTACTG
CTTCAACATGATGAAGAACAGAAGGCTTACCAGGCCTTGCAAGGATAGAAACACTTTCATCCACGGAAACAAGAACGACA
TCAAGGCTATCTGCGAGGATAGAAACGGACAACCTTACAGAGGTGATCTCAGGATCTCTAAGTCTGAGTTCCAGATCACT
ATCTGCAAGCACAAGGGTGGAAGCTCTAGACCTCCTTGTAGATACGGTGCTACTGAGGATTCTAGAGTTATCGTTGTTGG
ATGCGAGAACGGACTTCCTGTTCATTTCGATGAGTCTTTCATCACCCCTAGGCACTAA
```

FIGURE 7

```
              *        20         *        40         *        60
monocot   ATGCAGGACGACTACCGCTACATCCACTTTCTCACCCAGCACTACGACGCCAAGCCAAAG  :  60
dicot     ATGCAGGACGACTACCGTTACATCCATTTCTTGACTCAGCACTACGACGCTAAGCCTAAG  :  60

*        80         *        100        *        120
monocot   GGCCGCAACGACGAGTACTGCTTCAACATGATGAAGAACCGCCGCCTCACCCGCCCATGC  :  120
dicot     GGAAGAAACGATGAGTACTGCTTCAACATGATGAAGAACAGAAGGCTTACCAGGCCTTGC  :  120

*        140        *        160        *        180
monocot   AAGGACCGCAACACCTTCATCCACGGCAACAAGAACGACATCAAGGCCATCTGCGAGGAC     180
dicot     AAGGATAGAAACACTTTCATCCACGGAAACAAGAACGACATCAAGGCTATCTGCGAGGAT     180

*        200        *        220        *        240
monocot   CGCAACGGCCAGCCATACAGGGGCGACCTCCGCATCTCCAAGTCCGAGTTCCAGATCACC     240
dicot   : AGAAACGGACAACCTTACAGAGGTGATCTCAGGATCTCTAAGTCTGAGTTCCAGATCACT     240

*        260        *        280        *        300
monocot : ATCTGCAAGCACAAGGGCGGCTCCTCCGCCCACCATGCAGGTACGGCGCCACCGAGGAC     300
dicot     ATCTGCAAGCACAAGGGTGGAAGCTCTAGACCTCCTTGTAGATACGGTGCTACTGAGGAT     300

*        320        *        340        *        360
monocot : TCCCGCGTGATCGTGGTGGGCTGCGAGAACGGCCTCCCAGTGCACTTCGACGAGTCCTTC     360
dicot     TCTAGAGTTATCGTTGTTGGATGCGAGAACGGACTTCCTGTTCATTTCGATGAGTCTTTC     360

*
monocot : ATCACCCCACGCCACTGA :  378
dicot     ATCACCCCTAGGCACTAA    378
```

FIGURE 8

ATGGCGGATACAGCTAGAGGAACCCATCACGATATCATCGGCAGAGACCAGTACCCGATGATGGGCCGAGACCGAGACCA
GTACCAGATGTCCGGACGAGGATCTGACTACTCCAAGTCTAGGCAGATTGCTAAAGCTGCAACTGCTGTCACAGCTGGTG
GTTCCCTCCTTGTTCTCTCCAGCCTTACCCTTGTTGGAACTGTCATAGCTTTGACTGTTGCAACACCTCTGCTCGTTATC
TTCAGCCCAATCCTTGTCCCGGCTCTCATCACAGTTGCACTCCTCATCACCGGTTTTCTTTCCTCTGGAGGGTTTGGCAT
TGCCGCTATAACCGTTTTCTCTTGGATTTACAAGTACGCAACGGGAGAGCACCCACAGGGATCAGACAAGTTGGACAGTG
CAAGGATGAAGTTGGGAAGCAAAGCTCAGGATCTGAAAGACAGAGCTCAGTACTACGGACAGCAACATACTGGTGGGGAA
CATGACCGTGACCGTACTCGTGGTGGCCAGCACACTACTCTTGTTCCTCGTGGATCTCAGGACGACTACCGTTACATCCA
TTTCTTGACTCAGCACTACGACGCTAAGCCTAAGGGAAGAAACGATGAGTACTGCTTCAACATGATGAAGAACAGAAGGC
TTACCAGGCCTTGCAAGGATAGAAACACTTTCATCCACGGAAACAAGAACGACATCAAGGCTATCTGCGAGGATAGAAAC
GGACAACCTTACAGAGGTGATCTCAGGATCTCTAAGTCTGAGTTCCAGATCACTATCTGCAAGCACAAGGGTGGAAGCTC
TAGACCTCCTTGTAGATACGGTGCTACTGAGGATTCTAGAGTTATCGTTGTTGGATGCGAGAACGGACTTCCTGTTCATT
TCGATGAGTCTTTCATCACCCCTAGGCACTAA

FIGURE 9

MADTARGTHHDIIGRDQYPMMGRDRDQYQMSGRGSDYSKSRQIAKAATAVTAGGSLLVLSSLTLVGTVIALTVATPLLVI
FSPILVPALITVALLITGFLSSGGFGIAAITVFSWIYKYATGEHPQGSDKLDSARMKLGSKAQDLKDRAQYYGQQHTGGE
HDRDRTRGGQHTTLVPRGSQDDYRYIHFLTQHYDAKPKGRNDEYCFNMMKNRRLTRPCKDRNTFIHGNKNDIKAICEDRN
GQPYRGDLRISKSEFQITICKHKGGSSRPPCRYGATEDSRVIVVGCENGLPVHFDESFITPRH

FIGURE 10

```
GAATTCAAATTTATTATGTGTTTTTTTTCCGTGGTCGAGATTGTGTATTATTCTTTAGTTATTACAAGACTTTTAGCTAA
AATTTGAAAGAATTTACTTTAAGAAAATCTTAACATCTGAGATAATTTCAGCAATAGATTATATTTTTCATTACTCTAGC
AGTATTTTTGCAGATCAATCGCAACATATATGGTTGTTAGAAAAAATGCACTATATATATATATATTATTTTTTCAATTA
AAAGAGCATGATATATAATATATATATATATATATATGTGTGTGTATATGGTCAAAGAAATTCTTATACAAATATA
CACGAACACATATATTTGACAAAATCAAAGTATTACACTAAACAATGAGTTGGTGCATGGCCAAAACAAATATGTAGATT
AAAAATTCCAGCCTCCAAAAAAAAATCCAAGTGTTGTAAAGCATTATATATATATAGTAGATCCCAAATTTTTGTACAAT
TCCACACTGATCGAATTTTTAAAGTTGAATATCTGACGTAGGATTTTTTAATGTCTTACCTGACCATTTACTAATAACA
TTCATACGTTTTCATTTGAAATATCCTCTATAATTATATTGAATTTGGCACATAATAAGAAACCTAATTGGTGATTTATT
TTACTAGTAAATTTCTGGTGATGGGCTTTCTACTAGAAAGCTCTCGGAAAATCTTGGACCAAATCCATATTCCATGACTT
CGATTGTTAACCCTATTAGTTTTCACAAACATACTATCAATATCATTGCAACGGAAAAGGTACAAGTAAAACATTCAATC
CGATAGGGAAGTGATGTAGGAGGTTGGGAAGACAGGCCCAGAAAGAGATTTATCTGACTTGTTTTGTGTATAGTTTTCAA
TGTTCATAAAGGAAGATGGAGACTTGAGAAGTTTTTTTGGACTTTGTTTAGCTTTGTTGGGCGTTTTTTTTTTTGATC
AATAACTTTGTTGGGCTTATGATTTGTAATATTTTCGTGGACTCTTTAGTTTATTTAGACGTGCTAACTTTGTTGGGCTT
ATGACTTGTTGTAACATATTGTAACAGATGACTTGATGTGCGACTAATCTTTACACATTAAACATAGTTCTGTTTTTTGA
AAGTTCTTATTTTCATTTTTATTTGAATGTTATATATTTTTCTATATTTATAATTCTAGTAAAAGGCAAATTTTGCTTTT
AAATGAAAAAAATATATATTCCACAGTTTCACCTAATCTTATGCATTTAGCAGTACAAATTCAAAAATTTCCCATTTTA
TTCATGAATCATACCATTATATATTAACTAAATCCAAGGTAAAAAAAAGGTATGAAAGCTCTATAGTAAGTAAAATATAA
ATTCCCCATAAGGAAAGGGCCAAGTCCACCAGGCAAGTAAAATGAGCAAGCACCACTCCACCATCACACAATTTCACTCA
TAGATAACGATAAGATTCATGGAATTATCTTCCACGTGGCATTATTCCAGCGGTTCAAGCCGATAAGGGTCTCAACACCT
CTCCTTAGGCCTTTGTGGCCGTTACCAAGTAAAATTAACCTCACACATATCCACACTCAAAATCCAACGGTGTAGATCCT
AGTCCACTTGAATCTCATGTATCCTAGACCCTCCGATCACTCCAAAGCTTGTTCTCATTGTTGTTATCATTATATATAGA
TGACCAAAGCACTAGACCAAACCTCAGTCACACAAAGAGTAAAGAAGAACAATGCAGGACGACTACCGTTACATCCATTT
CTTGACTCAGCACTACGACGCTAAGCCTAAGGGAAGAAACGATGAGTACTGCTTCAACATGATGAAGAACAGAAGGCTTA
CCAGGCCTTGCAAGGATAGAAACACTTTCATCCACGGAAACAAGAACGACATCAAGGCTATCTGCGAGGATAGAAACGGA
CAACCTTACAGAGGTGATCTCAGGATCTCTAAGTCTGAGTTCCAGATCACTATCTGCAAGCACAAGGGTGGAAGCTCTAG
ACCTCCTTGTAGATACGGTGCTACTGAGGATTCTAGAGTTATCGTTGTTGGATGCGAGAACGGACTTCCTGTTCATTTCG
ATGAGTCTTTCATCACCCCTAGGCACAAGGATGAGCTCTAAagaaggagtgcgtcgaagcagatcgttcaaacatttggc
aataaagtttcttaagattgaatcctgttgccggtcttgcgatgattatcatataatttctgttgaattacgttaagcat
gtaataattaacatgtaatgcatgacgttatttatgagatgggtttttatgattagagtcccgcaattatacatttaata
cgcgatagaaaacaaaatatagcgcgcaaactaggataaattatcgcgcggtgtcatctatgttactagatcga
```

FIGURE 11

```
GGATCCACGGGCTCACTGGCGGATATAGAGGGCTGGAAAGCTTTCAATAGTTGCCTTGCGAGAGGGGAAAGAACTTGTTC
TGCGTGTGGACGGTTACTATGCTAGTTCAATTAATTGTACCAACAAAACATATATTTTATTTTGAGAAACGGTGTACAAA
TGTAGACGTTCACATACACACATGTACAACAACCCCTATAAATGCACACACGCACACTCTACGCCTATGGGCATACTTTC
GAGAGAGTGAGCCATCAGATCTTATGATAAAATGTAAAATATTTTGCCCGCACCACTCAAGTCGCATCTCAGAAAATTTG
TACTCAAGAAACTTTTGGCTTTAAATGAAACCAAAAACAAGAAAAGCTGGAAAAAGGTTGTGTGGCAGCCAGCCAATGAC
ATGAAGGACTGAAATTTCCAGCACACACAACGCATCCGACGGCCATGCTTCTTCCACTGATCCGGAGAAGATAAGGAAAC
GAGGCAACCAGAGAACGTCAGCCACCCCAACCACATCTGTACCAAAGAAACGACGCTAAGTGTCTGGCTATATATACCGT
AGTGACCCGGCAATGGTGGCCTCACCTGTAGCCGGCATCCTCCTCTCCTCCGATAATACAATACCATGCAGGACGACTAC
CGCTACATCCACTTTCTCACCCAGCACTACGACGCCAAGCCAAAGGGCCGCAACGACGAGTACTGCTTCAACATGATGAA
GAACCGCCGCCTCACCCGCCCATGCAAGGACCGCAACACCTTCATCCACGGCAACAAGAACGACATCAAGGCCATCTGCG
AGGACCGCAACGGCCAGCCATACAGGGGCGACCTCCGCATCTCCAAGTCCGAGTTCCAGATCACCATCTGCAAGCACAAG
GGCGGCTCCTCCCGCCACCATGCAGGTACGGCGCCACCGAGGACTCCCGCGTGATCGTGGTGGGCTGCGAGAACGGCCT
CCCAGTGCACTTCGACGAGTCCTTCATCACCCCACGCCACAAGGATGAGCTCTGAagaaggagtgcgtcgaagcagatcg
ttcaaacatttggcaataaagtttcttaagattgaatcctgttgccggtcttgcgatgattatcatataatttctgttga
attacgttaagcatgtaataattaacatgtaatgcatgacgttatttatgagatgggtttttatgattagagtcccgcaa
ttatacatttaatacgcgatagaaaacaaaatatagcgcgcaaactaggataaattatcgcgcgcggtgtcatctatgtt
actagatcga
```

FIGURE 14

```
CCGTGGTCGAGATTGTGTATTATTCTTTAGTTATTACAAGACTTTTAGCTAAAATTTGAAAGAATTTACTTTAAGAAAAT
CTTAACATCTGAGATAATTTCAGCAATAGATTATATTTTTCATTACTCTAGCAGTATTTTTGCAGATCAATCGCAACATA
TATGGTTGTTAGAAAAAATGCACTATATATATATATATTATTTTTTCAATTAAAAGTGCATGATATATAATATATATATA
TATATATATATGTGTGTGTATATGGTCAAAGAAATTCTTATACAAATATACACGAACACATATATTTGACAAAATCAA
AGTATTACACTAAACAATGAGTTGGTGCATGGCCAAAACAAATATGTAGATTAAAAATTCCAGCCTCCAAAAAAAAATCC
AAGTGTTGTAAAGCATTATATATATATAGTAGATCCCAAATTTTTGTACAATTCCACACTGATCGAATTTTTAAAGTTGA
ATATCTGACGTAGGATTTTTTTAATGTCTTACCTGACCATTTACTAATAACATTCATACGTTTTCATTTGAAATATCCTC
TATAATTATATTGAATTTGGCACATAATAAGAAACCTAATTGGTGATTTATTTTACTAGTAAATTTCTGGTGATGGGCTT
TCTACTAGAAAGCTCTCGGAAAATCTTGGACCAAATCCATATTCCATGACTTCGATTGTTAACCCTATTAGTTTTCACAA
ACATACTATCAATATCATTGCAACGGAAAAGGTACAAGTAAAACATTCAATCCGATAGGGAAGTGATGTAGGAGGTTGGG
AAGACAGGCCCAGAAAGAGATTTATCTGACTTGTTTTGTGTATAGTTTTCAATGTTCATAAAGGAAGATGGAGACTTGAG
AAGTTTTTTTTGGACTTTGTTTAGCTTTGTTGGGCGTTTTTTTTTTTGATCAATAACTTTGTTGGGCTTATGATTTGTA
ATATTTTCGTGGACTCTTTAGTTTATTTAGACGTGCTAACTTTGTTGGGCTTATGACTTGTTGTAACATATTGTAACAGA
TGACTTGATGTGCGACTAATCTTTACACATTAAACATAGTTCTGTTTTTTGAAAGTTCTTATTTTCATTTTTATTTGAAT
GTTATATATTTTTCTATATTTATAATTCTAGTAAAAGGCAAATTTTGCTTTTAAATGAAAAAAATATATATTCCACAGTT
TCACCTAATCTTATGCATTTAGCAGTACAAATTCAAAAATTTCCCATTTTTATTCATGAATCATACCATTATATATTAAC
TAAATCCAAGGTAAAAAAAGGTATGAAAGCTCTATAGTAAGTAAAATATAAATTCCCCATAAGGAAAGGGCCAAGTCCA
CCAGGCAAGTAAAATGAGCAAGCACCACTCCACCATCACACAATTTCACTCATAGATAACGATAAGATTCATGGAATTAT
CTTCCACGTGGCATTATTCCAGCGGTTCAAGCCGATAAGGGTCTCAACACCTCTCCTTAGGCCTTTGTGGCCGTTACCAA
GTAAAATTAACCTCACACATATCCACACTCAAAATCCAACGGTGTAGATCCTAGTCCACTTGAATCTCATGTATCCTAGA
CCCTCCGATCACTCCAAAGCTTGTTCTCATTGTTGTTATCATTATATATAGATGACCAAAGCACTAGACCAAACCTCAGT
CACACAAAGAGTAAGAAGGATCCTCTAGAATGCAAGATGACTACAGATACATCCACTTCCTGACCCAGCACTACGATGC
CAAACCAAAGGGCCGGAACGACGAGTACTGCTTCAACATGATGAAGAACCGACGCCTGACCAGACCTTGCAAAGACCGCA
ACACCTTCATCCACGGCAACAAGAACGACATCAAGGCCATCTGTGAGGACAGAAATGGACAGCCTTACAGAGGCGATCTC
AGAATCAGCAAGTCTGAGTTCCAGATCACCATCTGCAAGCATAAAGGAGGTTCCTCCCGGCCTCCATGCCGGTACGGAGC
CACAGAAGACTCCAGAGTCATTGTTGTCGGCTGTGAGAATGGCTTGCCCGTCCACTTTGATGAGTCCTTTATCACTCCAC
GCCACAAGGATGAGCTCTAGctgcaggcatgcccgctgaaatcaccagtctctctctacaaatctatctctctctataat
aatgtgtgagtagttcccagataagggaattagggttcttatagggtttcgctcatgtgttgagcatataagaaaccctt
agtatgtatttgtatttgtaaaatacttctatcaataaaatttctaattcctaaaaccaaaatccaggggtaccgagctc
```

FIGURE 17

```
CCGTGGTCGAGATTGTGTATTATTCTTTAGTTATTACAAGACTTTTAGCTAAAATTTGAAAGAATTTACTTTAAGAAAAT
CTTAACATCTGAGATAATTTCAGCAATAGATTATATTTTTCATTACTCTAGCAGTATTTTTGCAGATCAATCGCAACATA
TATGGTTGTTAGAAAAAATGCACTATATATATATATATTATTTTTTCAATTAAAAGTGCATGATATATAATATATATATA
TATATATATATGTGTGTGTATATGGTCAAAGAAATTCTTATACAAATATACACGAACACATATATTTGACAAAATCAA
AGTATTACACTAAACAATGAGTTGGTGCATGGCCAAAACAAATATGTAGATTAAAAATTCCAGCCTCCAAAAAAAAATCC
AAGTGTTGTAAAGCATTATATATATATAGTAGATCCCAAATTTTGTACAATTCCACACTGATCGAATTTTTAAAGTTGA
ATATCTGACGTAGGATTTTTTTAATGTCTTACCTGACCATTTACTAATAACATTCATACGTTTTCATTTGAAATATCCTC
TATAATTATATTGAATTTGGCACATAATAAGAAACCTAATTGGTGATTTATTTTACTAGTAAATTTCTGGTGATGGGCTT
TCTACTAGAAAGCTCTCGGAAAATCTTGGACCAAATCCATATTCCATGACTTCGATTGTTAACCCTATTAGTTTTCACAA
ACATACTATCAATATCATTGCAACGGAAAAGGTACAAGTAAAACATTCAATCCGATAGGGAAGTGATGTAGGAGGTTGGG
AAGACAGGCCCAGAAAGAGATTTATCTGACTTGTTTTGTGTATAGTTTTCAATGTTCATAAAGGAAGATGGAGACTTGAG
AAGTTTTTTTGGACTTTGTTTAGCTTTGTTGGGCGTTTTTTTTTTGATCAATAACTTTGTTGGGCTTATGATTTGTA
ATATTTCGTGGACTCTTTAGTTTATTTAGACGTGCTAACTTTGTTGGGCTTATGACTTGTTGTAACATATTGTAACAGA
TGACTTGATGTGCGACTAATCTTTACACATTAAACATAGTTCTGTTTTTTGAAAGTTCTTATTTTCATTTTTATTTGAAT
GTTATATATTTTTCTATATTTATAATTCTAGTAAAAGGCAAATTTTGCTTTTAAATGAAAAAAATATATATTCCACAGTT
TCACCTAATCTTATGCATTTAGCAGTACAAATTCAAAAATTTCCCATTTTTATTCATGAATCATACCATTATATATTAAC
TAAATCCAAGGTAAAAAAAGGTATGAAAGCTCTATAGTAAGTAAAATATAAATTCCCCATAAGGAAAGGGCCAAGTCCA
CCAGGCAAGTAAAATGAGCAAGCACCACTCCACCATCACACAATTTCACTCATAGATAACGATAAGATTCATGGAATTAT
CTTCCACGTGGCATTATTCCAGCGGTTCAAGCCGATAAGGGTCTCAACACCTCTCCTTAGGCCTTTGTGGCCGTTACCAA
GTAAAATTAACCTCACACATATCCACACTCAAAATCCAACGGTGTAGATCCTAGTCCACTTGAATCTCATGTATCCTAGA
CCCTCCGATCACTCCAAAGCTTGTTCTCATTGTTGTTATCATTATATATAGATGACCAAAGCACTAGACCAAACCTCAGT
CACACAAAGAGTAAAGAAGGATCCTCTAGAATGCAGGACGACTACCGCTACATCCACTTTCTCACCCAGCACTACGACGC
CAAGCCAAAGGGCCGCAACGACGAGTACTGCTTCAACATGATGAAGAACCGCCGCCTCACCCGCCCATGCAAGGACCGCA
ACACCTTCATCCACGGCAACAAGAACGACATCAAGGCCATCTGCGAGGACCGCAACGGCCAGCCATACAGGGGCGACCTC
CGCATCTCCAAGTCCGAGTTCCAGATCACCATCTGCAAGCACAAGGGCGGCTCCTCCCGCCCACCATGCAGGTACGGCGC
CACCGAGGACTCCCGCGTGATCGTGGTGGGCTGCGAGAACGGCCTCCCAGTGCACTTCGACGAGTCCTTCATCACCCCAC
GCCACAAGGATGAGCTCTGActgcaggcatgcccgctgaaatcaccagtctctctctacaaatctatctctctctataat
aatgtgtgagtagttcccagataagggaattagggttcttataggtttcgctcatgtgttgagcatataagaaaccctt
agtatgtatttgtatttgtaaaatacttctatcaataaaatttctaattcctaaaaccaaaatccaggggtaccgagctc
```

FIGURE 19

```
ATCTGTTCATCTACCTTACTAGTCTGCATGATTAGTTTATTCGTTATTTTCGTAGTCATGATTTATCAATTACTCGTACG
GATTATTTCATATGGATATTTGCTTATATTTCCAACAATTTACACTGTCGAGTTTTGGCGCGGCTGCTGGAGTTACTCTT
AGAGTAGTTGGACTTGAGACAAAAGCTAGAATATCAATTATATATAGGAGTGAGGAGTTATTCTTTCGAAAGAACTTTAA
ACGGTAGCTGCACTTAGTCGTCGCAATGAAATACTTGTCGTACTACCATGATAATTGGTAATATGAGAGGGAATATTAAT
TCCTCAGTGATTTGAATTTTGTGTGCTCATGTGCAGTCACCCACGCCATGCATCCGACGACGGGCGGCTATACCAACTCT
TGCACTGATCCGGAGGGATAAGGCGCCATGCAACCAGGGAACGTCGTCCACCCCTTCCACATCCTGTATCAAATTAAGGA
ACGGGCGCTGAGCCTATGCCGAGACATATATAATGCGGCGACTCGGACATGGAGGGGCCTCAGGCATAGCCCAGCTAGTT
ATCTCATTCTCTCCTTAGCAATAATACTTAGCACCATGGCCCCCGCGGTGGAATTCATGCAGGACGACTACCGCTACATC
CACTTTCTCACCCAGCACTACGACGCCAAGCCAAAGGGCCGCAACGACGAGTACTGCTTCAACATGATGAAGAACCGCCG
CCTCACCCGCCCATGCAAGGACCGCAACACCTTCATCCACGGCAACAAGAACGACATCAAGGCCATCTGCGAGGACCGCA
ACGGCCAGCCATACAGGGGCGACCTCCGCATCTCCAAGTCCGAGTTCCAGATCACCATCTGCAAGCACAAGGGCGGCTCC
TCCCGCCCACCATGCAGGTACGGCGCCACCGAGGACTCCCGCGTGATCGTGGTGGGCTGCGAGAACGGCCTCCCAGTGCA
CTTCGACGAGTCCTTCATCACCCCACGCCACAAGGATGAGCTCTGAgaattcaacaataattttctgagcctagtatcca
tgatcatgatatagtaagggaaaaatcatatctataagtttccgaacttagtgaaaaaaaacctgtaaaagatatgcagt
catatacacatgtgaaattaggtaggaaaatatgataatctcgtagatgaggaaaaaatattgtacaccaaactattgta
agttacagtaatgtaatgtaaaaaaagttttttaagttacagaaggtacataccgcaaataatcatattattttaccaaga
tatttttttctggagtattcctttcaagtatcttttatctctagaatcttctccaatcatgagtggcaaccgaaatggag
ctcctgtgttgctcccgtgtctcaccccttcggccccactgtcatgggtggacctattctcacggcggctgtcctga
gaaacaaaaatagcagctgaaatgaagacacggcgacacgcaagccagcatctctcattgaacctgcggagtgagatagc
tctcgtggcgctgctctacttgacgcgtttgtctcatacaacagcgcatggctccttcatgtcaggtccatgatccacag
atggtatgattgggtttggaacatttttggggtttgtgatatgtcgtagatacaaagggaaatgtctgaagcatgcatgg
atgggttccctgctcatgtactcaatgt
```

FIGURE 21

ATTGGGAAGCTTTCTTCATCGGTGATTGATTCCTTCAAAGACTTATGTTTCTTATCTTGCTTCTGAGGCAAGTATTCAGT
TACCAGTTACCACTTATATTCTGGACTTTCTGACTGCATCCTCATTTTTCCAACATTTTAAATTTCACTATTGGCTGAAT
GCTTCTTCTTTGAGGAAGAAACAATTCAGGTGGCAGAAATGTATCAACCAATGCATATATGCAAATGTACCTCTTGTTCT
CAAAACATCTATCGGATGGTTCCATTTGCTTTGTCATCCAATTAGTGACTACTTTATATTATTCACTCCTCTTTATTACT
ATTTTCATGCGAGGTTGCCATGTACATTATATTTGTAAGGATTGACGCTATTGAGCGTTTTTCTTCAATTTTCTTTATTT
TAGACATGGGTATGAAATGTGTGTTAGAGTTGGGTTGAATGAGATATACGTTCAAGTGAATGGCATACCGTTCTGAGTA
AGGATGACCTACCCATTCTTGAGACAAATGTTACATTTTAGTATCAGAGTAAAATGTGTACCTATAACTCAAATTCGATT
GACATGTATCCATTCAACATAAAATTAAACCAGCCTGCACCTGCATCCACATTTCAAGTATTTTCAAACCGTTCGGCTCC
TATCCACCGGGTGTAACAAGACGGATTCCGAATTTGGAAGATTTTGACTCAAATTCCCAATTTATATTGACCGTGACTAA
ATCAACTTTAACTTCTATAATTCTGATTAAGCTCCCAATTTGTATTCCCAACGGCATTACCTCCAAAATTTATAGACTCT
CATCCCCTTTTAAACCAACTTAGTAAACGTTTTTTTTTTTAATTTTATGAAGTTAAGTTTTTACCTTGTTTTTAAAAAGA
ATCGTTCATAAGATGCCATGCCAGAACATTAGCTACACGTTACACATAGCATGCAGCCGCGGAGAATTGTTTTTCTTCGC
CACTTGTCACTCCCTTCAAACACCTAAGAGCTTCTCTCTCACAGCACACACATACAATCACATGCGTGCATGCATTATTA
CACGTGATCGCCATGCAAATCTCCTTTATAGCCTATAAATTAACTCATCCGCTTCACTCTTTACTCAAACCAAAACTCAT
CAATACAAACAAGATTAAAAACATACACCATGGGCGAATATGCAGGACGACTACCGTTACATCCATTTCTTGACTCAGCA
CTACGACGCTAAGCCTAAGGGAAGAAACGATGAGTACTGCTTCAACATGATGAAGAACAGAAGGCTTACCAGGCCTTGCA
AGGATAGAAACACTTTCATCCACGGAAACAAGAACGACATCAAGGCTATCTGCGAGGATAGAAACGGACAACCTTACAGA
GGTGATCTCAGGATCTCTAAGTCTGAGTTCCAGATCACTATCTGCAAGCACAAGGGTGGAAGCTCTAGACCTCCTTGTAG
ATACGGTGCTACTGAGGATTCTAGAGTTATCGTTGTTGGATGCGAGAACGGACTTCCTGTTCATTTCGATGAGTCTTTCA
TCACCCCTAGGCACAAGGATGAGCTCTAActgcaggcatgcccgctgaaatcaccagtctctctctacaaatctatctct
ctctataatgtgtgagtagttcccagataagggaattagggttcttatagggtttcgctcatgtgttgagcatataa
gaaacccttagtatgtatttgtatttgtaaaatacttctatcaataaaatttctaattcctaaaaccaaaatccaggggt
accgagctc

FIGURE 22

AAGCTTTCTTCATCGGTGATTGATTCCTTTAAAGACTTATGTTTCTTATCTTGCTTCTGAGGCAAGTATTCAGTTACCAG
TTACCACTTATATTCTGGACTTTCTGACTGCATCCTCATTTTTCCAACATTTTAAATTTCACTATTGGCTGAATGCTTCT
TCTTTGAGGAAGAAACAATTCAGATGGCAGAAATGTATCAACCAATGCATATATACAAATGTACCTCTTGTTCTCAAAAC
ATCTATCGGATGGTTCCATTTGCTTTGTCATCCAATTAGTGACTACTTTATATTATTCACTCCTCTTTATTACTATTTTC
ATGCGAGGTTGCCATGTACATTATATTTGTAAGGATTGACGCTATTGAGCGTTTTTCTTCAATTTTCTTTATTTTAGACA
TGGGTATGAAATGTGTGTTAGAGTTGGGTTGAATGAGATATACGTTCAAGTGAAGTGGCATACCGTTCTCGAGTAAGGAT
GACCTACCCATTCTTGAGACAAATGTTACATTTTAGTATCAGAGTAAAATGTGTACCTATAACTCAAATTCGATTGACAT
GTATCCATTCAACATAAAATTAAACCAGCCTGCACCTGCATCCACATTTCAAGTATTTTCAAACCGTTCGGCTCCTATCC
ACCGGGTGTAACAAGACGGATTCCGAATTTGGAAGATTTTGACTCAAATTCCCAATTTATATTGACCGTGACTAAATCAA
CTTTAACTTCTATAATTCTGATTAAGCTCCCAATTTATATTCCCAACGGCACTACCTCCAAAATTTATAGACTCTCATCC
CCTTTTAAACCAACTTAGTAAACGTTTTTTTTTTAATTTTATGAAGTTAAGTTTTTACCTTGTTTTTAAAAAGAATCGT
TCATAAGATGCCATGCCAGAACATTAGCTACACGTTACACATAGCATGCAGCCGCGGAGAATTGTTTTTCTTCGCCACTT
GTCACTCCCTTCAAACACCTAAGAGCTTCTCTCTCACAGCACACACATACAATCACATGCGTGCATGCATTATTACACGT
GATCGCCATGCAAATCTCCTTTATAGCCTATAAATTAACTCATCCGCTTCACTCTTTACTCAAACCAAAACTCATCAATA
CAAACAAGATTAAAAACATACACGAATGCAGGACGACTACCGTTACATCCATTTCTTGACTCAGCACTACGACGCTAAGC
CTAAGGGAAGAAACGATGAGTACTGCTTCAACATGATGAAGAACAGAAGGCTTACCAGGCCTTGCAAGGATAGAAACACT
TTCATCCACGGAAACAAGAACGACATCAAGGCTATCTGCGAGGATAGAAACGGACAACCTTACAGAGGTGATCTCAGGAT
CTCTAAGTCTGAGTTCCAGATCACTATCTGCAAGCACAAGGGTGGAAGCTCTAGACCTCCTTGTAGATACGGTGCTACTG
AGGATTCTAGAGTTATCGTTGTTGGATGCGAGAACGGACTTCCTGTTCATTTCGATGAGTCTTTCATCACCCCTAGGCAC
AAGGATGAGCTCTAAagaaggagtgcgtcgaagcagatcgttcaaacatttggcaataaagtttcttaagattgaatcct
gttgccggtcttgcgatgattatcatataatttctgttgaattacgttaagcatgtaataattaacatgtaatgcatgac
gttatttatgagatgggttttttatgattagagtcccgcaattatacatttaatacgcgatagaaaacaaaatatagcgcg
caaactaggataaattatcgcgcgcggtgtcatctatgttactagatcga
```

FIGURE 23

```
GAATTCTTGACAAACTAGTTAGTCCATGTGTTTGTGTTGTTCGTCAACCACCAAAATTAATTATAGGAAATGGTTAACCC
TATTTCCCTTTCACAACTCAACTGTCGTGGTACTCCATTACAGCACTTACGTACACGAGTTCTATGAGAGCAGACCTCCA
AAATGAATATCTGCTAAGTGTTTATCTACTTAGATGAAGGACGACAATCACTTTCTTGGGAAATATTAGCGACACAACTC
CTTACTTCCTCCTCTTCTTCCTAGTGTTTTTTGTTGTGATTGAGTCGACACAACAACAACACTGCACTATTACAACCAGT
ACGACTATATCAACTAGCAATGTCTTCCTTATATGTTACTATTTATTTTGCTAATATTCATTATGTTTAAATCACATGTG
CACCTTTCTATTGACATCAAAAAATTAGTATCAACTTTCTAGATTAAAATGCAACTAAAAGTACATAAATTTCTATCGGT
GGGGATCGAGTGATTCTTTAAACCGATTATTACACAAGTTAACCACACTAAAATTAACATTGGTGAATCGTGCCATGATT
TTTTTCTAGTGCAAAATAGCCAAACCAAGCAAAACATATGTGGCTATCGTTACACATGTGTAAAGGTATTGCATCACACC
ATTGTCACCCATGTATTTGGACAATACCGAGAGGAAAAACCACTTATTTATTGTATTTTATCAAGTTTATCTTGCTTACG
TATAAATTATAACCCAACAAAGTAATCACTAAATGTCAAAACCAACTAGATACCATGTCATCTCTACCTTATCTTACTAA
TATTCTTTTTGCAAAATCGAAAATTAATCTTGCACAAGCACAAGGACTGAGATGTGTATAAATATCTCTTAGATTAGCTA
GCTAATATATCGCACATATTATTGAGACCAACTAGCAATATAGAAAGCACAATATTGTACCAATAATGCAGGACGACTAC
CGCTACATCCACTTTCTCACCCAGCACTACGACGCCAAGCCAAAGGGCCGCAACGACGAGTACTGCTTCAACATGATGAA
GAACCGCCGCCTCACCCGCCCATGCAAGGACCGCAACACCTTCATCCACGGCAACAAGAACGACATCAAGGCCATCTGCG
AGGACCGCAACGGCCAGCCATACAGGGGCGACCTCCGCATCTCCAAGTCCGAGTTCCAGATCACCATCTGCAAGCACAAG
GGCGGCTCCTCCCGCCCACCATGCAGGTACGGCGCCACCGAGGACTCCCGCGTGATCGTGGGGCTGCGAGAACGGCCT
CCCAGTGCACTTCGACGAGTCCTTCATCACCCCACGCCACAAGGATGAGCTCTGActgcaggcatgcccgctgaaatcac
cagtctctctctacaaatctatctctctataataatgtgtgagtagttcccagataagggaattagggttcttatagg
gtttcgctcatgtgttgagcatataagaaacccttagtatgtatttgtatttgtaaaatacttctatcaataaaatttct
aattcctaaaccaaaatccaggggtaccgagctc
```

FIGURE 25

```
GAATTCTTGACAAACTAGTTAGTCCATGTGTTTGTGTTGTTCGTCAACCACCAAAATTAATTATAGGAAATGGTTAACCC
TATTTCCCTTTCACAACTCAACTGTCGTGGTACTCCATTACAGCACTTACGTACACGAGTTCTATGAGAGCAGACCTCCA
AAATGAATATCTGCTAAGTGTTTATCTACTTAGATGAAGGACGACAATCACTTTCTTGGGAAATATTAGCGACACAACTC
CTTACTTCCTCCTCTTCTTCCTAGTGTTTTTTGTTGTGATTGAGTCGACACAACAACAACACTGCACTATTACAACCAGT
ACGACTATATCAACTAGCAATGTCTTCCTTATATGTTACTATTTATTTTGCTAATATTCATTATGTTTAAATCACATGTG
CACCTTTCTATTGACATCAAAAAATTAGTATCAACTTTCTAGATTAAAATGCAACTAAAAGTACATAAATTTCTATCGGT
GGGGATCGAGTGATTCTTTAAACCGATTATTACACAAGTTAACCACACTAAAATTAACATTGGTGAATCGTGCCATGATT
TTTTTCTAGTGCAAAATAGCCAAACCAAGCAAAACATATGTGGCTATCGTTACACATGTGTAAAGGTATTGCATCACACC
ATTGTCACCCATGTATTTGGACAATACCGAGAGGAAAAACCACTTATTTATTGTATTTTATCAAGTTTATCTTGCTTACG
TATAAATTATAACCCAACAAAGTAATCACTAAATGTCAAAACCAACTAGATACCATGTCATCTCTACCTTATCTTACTAA
TATTCTTTTTGCAAAATCGAAAATTAATCTTGCACAAGCACAAGGACTGAGATGTGTATAAATATCTCTTAGATTAGCTA
GCTAATATATCGCACATATTATTGAGACCAACTAGCAATATAGAAAGCACAATATTGTACCAATAATGCAGGACGACTAC
CGCTACATCCACTTTCTCACCCAGCACTACGACGCCAAGCCAAAGGGCCGCAACGACGAGTACTGCTTCAACATGATGAA
GAACCGCCGCCTCACCCGCCCATGCAAGGACCGCAACACCTTCATCCACGGCAACAAGAACGACATCAAGGCCATCTGCG
AGGACCGCAACGGCCAGCCATACAGGGGCGACCTCCGCATCTCCAAGTCCGAGTTCCAGATCACCATCTGCAAGCACAAG
GGCGGCTCCTCCCGCCCACCATGCAGGTACGGCGCCACCGAGGACTCCCGCGTGATCGTGGTGGGCTGCGAGAACGGCCT
CCCAGTGCACTTCGACGAGTCCTTCATCACCCCACGCCACAAGGATGAGCTCTGAagaaggagtgcgtcgaagcagatcg
ttcaaacatttggcaataaagtttcttaagattgaatcctgttgccggtcttgcgatgattatcatataatttctgttga
attacgttaagcatgtaataattaacatgtaatgcatgacgttatttatgagatgggtttttatgattagagtcccgcaa
ttatacatttaatacgcgatagaaaacaaaatatagcgcgcaaactaggataaattatcgcgcgcggtgtcatctatgtt
actagatcga
```

FIGURE 26

```
CACTCAAAACGAGAAAACTCATTGACACGTGATTAATTAAGTATTAATCTCTATATCTTCTCTACTATTATAAAAACTGA
AGAAGTATTTGTCAGTAATTTGGTACATCATCCGTGTATGAGTTGGTTTTTAAATTCGTTCGCTTTTTGAAATACAGAAG
GTGTCGTATAAGAAATATATTTAAAAAACTCGCATGCTAACTTGAGACGATCGGACTTCTAACTGCAGCTTATGATTTTC
TAAAAAAAAATATGTTCTTTTTTTGCGAGGAAAAAGATATATGTTCAAGTGAATTCTCAGGGAGAATTTCACTTTAGCTA
AACCATATAACAATAATAATATTAAAATAGTCTTTACCCGTTACAACGCACGGGCATTTTTCTAGTCATTTGAAAATTTT
AAAAATATGTTTATTCAAATAGATCTAAGAACTTCTAAAACATATTTGGACATGCAAACAATCTCAAGTGAAAGGTCATT
AACTTCAAAGTTGTAGATTTCGTCGAGCTCTACAATTTTGATATAAAGTTGGTTTTCATCCAACAACCTCATATGAGAAA
GTGGTTTCTAAAAAAATATGCACATATGATATGTAGGTCCATTTCTAAAGGCACACCCTCTCAAAATAAAATTTTAGAG
GTGATCGCTTAAGGCAACCGCCTCTAGAATTGAGGAGGCAATTAAGACGATCGCCTCTAAAAATCTATTTTATAGGTGAT
TTTCTAATGCAGTTACATAGACCATTCATCACTAGAAATCAGGCTATTTTTAAAGTTGATCTGTTTATATGGCTGCCTCT
AAAAATCAATGTCTAGTGGTTGTCCATGACTGCGGGTCCATTATATACGTTGGTTTTCTTATAAACTATATGTACAGTAA
CAATCACGATAATTTAATATATGTGGTCTCTTAGTTTATGTGTGTGTACGGTGTGTGTATTTATTTGTTTCTTTGCATCT
CCATAATCATGGTTATTTTGAATGGTTTGTTTTTCAGGCTACCGTGTTCCTGCTTCCCTCGCTTAATGCTTATGTGTCCT
GCCAGTTGCATTATCACGGATAACTGATCATATGCCATTTTATGGCTTCAGTCATAATATATTGTTTTACTAAGTTTGTC
TACATGATAAAGAGATACACATGGATCTCTCCTAAATAAAGTCATCATTGATGTCCACATGCATTATTATGTATGTTAAT
TTACAAGTGATAAAACACATACTACTACTACACCCAAGATGTGGTATAGCTCAAACACACCCCAACGTAGTAATTTTTCT
AGTGAGAGAACAATCATATATAGCAAAATATCCTATTGAGCCTGGCGATAATAACTCATAGTAATAATTTTATTATGTAA
GAAGTTTGTTTTTAGTTATCACACACACTGGGTGCATCTTAATGCTATATATTTATTTGGCCACACAAAAGTAGTTCTTC
CTCTAATGCCTTTCATTCTCAACTTTCATCATTTATTTGTCCTTTTGTTAGGTTCCGTCAACCTAATATGGGTGAAAAG
ACAGTTTTCTATTAATATGTTTTAATGCAAGATCTGTGATTTTTATATTTTCTTTTGAGTTACAATTTTATACTAGCTT
ATTATGCATGATGGTCGAATATCTCTCATGAACCATAATATTATTTTAGTAATCAAGTGTGATGCAAAATCCTTTAAATT
TAGTATATTACATAAAAAAATAATTCTCAATTTCTACTTCTTAGCTTATAGGCTGTGCGCATATAGAATTTGAATTTTAG
AAGTTTTAAAGTTGATTTTGGTTTTTTATCATATTTATTTTAGCACTGACTTTTGAATAGCTAAAATTGAAAAACTTAT
CGTAAAAAATATTATTATTGGTTGCTTCGTTTATTCTGGATGCATCTTAACATTTACTGTAAAAATATAACCTATGGTTT
ACTTATATTTAATCAACAATATTTATTGTTAAAAAGTAATAGACAAGAGAAAAACAATCTTTTCTTCCATCTATTAACAT
TATGTTAATGGACAACTAACGGAAAGGGCAAATAAGATATCAAATTTAAGAATAAGTGTATAAGAGGGGAAGCCAATTTT
GTGAGAATAAATAAGGAACCGATCAAGTCTAGAGGACACATAAAGAATTTTCTCATCATGGTGTTCATATAACTAGCCCG
TTGAACTGTGAGATTGAATACTTTTGGGATAGTGAAAGAATATTTGACTTAATATTTTCTTGAACACTACAATCTGCTA
TTTGTTTCACATATAAAAAAGTGAATATTGCATCCTCAATAAATGATCTAACATAAGGTACATAAATATCTAAATCTTTC
TCTATTAATGTGTCATACATGGATGCATATATCTTAGTAAATATCTAAATCTTTCTCTATTAATGTGTGGATTCATACAT
GGATGCATATATCTTCAATAAGTGAGTAGTAAATATCTAAATCTTTCTCTATTAATGTGTGGATTCATACATGGATGCAT
ATATCTTCAATAAATGAGTAGCAAATGTTTAAATCTTTTCTTTATTAATGTGTGGGTTCAACATGCATGGATGCATATAT
CTTTAATAAATGAGCCAATTAAATATGAGGTGCACAAATATCCAAATCTTTGCATGCATAGGCTCTCTCTTCACCATTGA
TTTTACATCCAATGGATACAATTCGAGCAACATGTCAACTTTTCCCCTCGATGGCCTTATATAAACCCAACTATCCCCAA
CTAGAAGATACACACCACAACAATATAGCCACTGTATGATATCAAGAAAAAGGTCTATCCTAGCTGCTTTATACTAAAGC
AATAGCCATGCAGGACGACTACCGCTACATCCACTTTCTCACCCAGCACTACGACGCCAAGCCAAAGGGCCGCAACGACG
AGTACTGCTTCAACATGATGAAGAACCGCCGCCTCACCCGCCCATGCAAGGACCGCAACACCTTCATCCACGGCAACAAG
AACGACATCAAGGCCATCTGCGAGGACCGCAACGGCCAGCCATACAGGGGCGACCTCCGCATCTCCAAGTCCGAGTTCCA
GATCACCATCTGCAAGCACAAGGGCGGCTCCTCCCGCCCACCATGCAGGTACGGCGCCACCGAGGACTCCCGCGTGATCG
TGGTGGGCTGCGAGAACGGCCTCCCAGTGCACTTCGACGAGTCCTTCATCACCCACGCCACAAGGATGAGCTCTGAaga
aggagtgcgtcgaagcagatcgttcaaacatttggcaataaagtttcttaagattgaatcctgttgccggtcttgcgatg
attatcatataatttctgttgaattacgttaagcatgtaataattaacatgtaatgcatgacgttatttatgagatgggt
ttttatgattagagtcccgcaattatacatttaatacgcgatagaaaacaaaatatagcgcgcaaactaggataaattat
cgcgcgcggtgtcatctatgttactagatcga
```

FIGURE 28

GCATGCAAATATGCAACATAATTTCCTTTTTACTTGGCTAATTATATTTGATAAATATTTCACAGATATACAATAATCAA
ACACAATAAATCATATGTGTTTTAGTTTTAGTTCTCATATCCAAATATACAATAGCTAACCAAATCTCATCGGGAAGTT
AGCCATGCCGAGGTAGGTTGTTGCCGGAATGTTTTTAGTTTTAGTTCTCATACAACCAAATCTCATTCAAATATATAAAA
CATTCCGGCAACAACTTGTGGCGTACATCTAGTTACAAGGGAATATTAGTGATGGCGTGAGCAAGCGATAAGGCCAAGGA
GAGAAGAAGTGCATCGTCTACGGAGGCCAGGGAAAGACAATGGACATGCAGAGAGGCAGGGCGGGGAAGAAACACTTGG
AGATCATAGAAGAAGATAAGAGGTTAAACATAGGAGGAGGATATAATGGACAATTAAATCTGCGTTAGTTGAACTCATTT
GGGAAGTAAACAAATTTTCTATTCTGTGTAAACCAAACTATTTGACGCGGATTTTCTCTGAAGATCCTATATTAATTTTA
GACATGGTTTGGCTAGTTCATTTGTCGTGAAAAGGTGTTTCCATAAGTCCAAAATTCTACCAACTTTTTGTATGGCACG
TCATAGCATAGATAGATGTTGTGAGTCACTGGATAGATATTGTGAGTCATAGCATGGATTCGTGTTGCTGGAAATCCAAC
TACATGACAAGCAACAAAACCTGAAATGGGCTTTAGGAGTTAACAATTTACTTGTTCCATGCAGGCTACCTTCCACTACT
CGACATGCTTAGAAGCTTTGAGTGGCCGTAGATTTGCAAAAGCAATGGCTAACAGACACATATTCTGCCAAACCCCAAGA
AGGATAATCACTTTTCTTAGATAAAAAAGAACAGACCAATATACAAACATCCACACTTCTGCAAACAATACATCAGAACT
AGGATTACGCCGATTACGTGGCTTTAGCAGACTGTCCAAAAATCTGTTTTGCAAAGCTCCAATTGCTCCTTGCTTATCCA
GCTTCTTTTGTGTTGGCAAACTGCGCTTTTCCAACCGATTTGTTCTTCTCGCGCTTTCTTCTTAGGCTAAACAAACCTC
ACCGTGCACGCAGCCATGGTCCTGAACCTTCACCTCGTCCCTATAAAAGCCTAGCCAACCTTCACAATCTTATCATCACC
CACAACACCGAGCACCACAAACTAGAGATCAATTCACTGATAGTCCACCGAGATGCAGGACGACTACCGCTACATCCACT
TTCTCACCCAGCACTACGACGCCAAGCCAAAGGGCCGCAACGACGAGTACTGCTTCAACATGATGAAGAACCGCCGCTC
ACCCGCCCATGCAAGGACCGCAACACCTTCATCCACGGCAACAAGAACGACATCAAGGCCATCTGCGAGGACCGCAACGG
CCAGCCATACAGGGGCGACCTCCGCATCTCCAAGTCCGAGTTCCAGATCACCATCTGCAAGCACAAGGGCGGCTCCTCCC
GCCCACCATGCAGGTACGGCGCCACCGAGGACTCCCGCGTGATCGTGGTGGGCTGCGAGAACGGCCTCCCAGTGCACTTC
GACGAGTCCTTCATCACCCCACGCCACAAGGATGAGCTCTGAagaaggagtgcgtcgaagcagatcgttcaaacatttgg
caataaagtttcttaagattgaatcctgttgccggtcttgcgatgattatcatataatttctgttgaattacgttaagca
tgtaataattaacatgtaatgcatgacgttatttatgagatgggtttttatgattagagtcccgcaattatacatttaat
acgcgatagaaaacaaaatatagcgcgcaaactaggataaattatcgcgcggtgtcatctatgttactagatcga
```

FIGURE 30

```
TTATAGAGAGAGATAGATTTGTAGAGAGAGACTGGTGATTTCAGCGTGTCCTCTCCAAATGAAATGAACTTCCTTATATA
GAGGAAGGGTCTTGCGAAGGATAGTGGGATTGTGCGTCATCCCTTACGTCAGTGGAGATATCACATCAATCCACTTGCTT
TGAAGACGTGGTTGGAACGTCTTCTTTTTCCACGATGCTCCTCGTGGGTGGGGGTCCATCTTTGGGACCACTGTCGGCAG
AGGCATCTTGAACGATAGCCTTTCCTTTATCGCAATGATGGCATTTGTAGGTGCCACCTTCCTTTTCTACTGTCTTCATG
ATGAAGTGACAGATAGCTGGGCAATGGAATCCGAGGAGGTTTCCCGAAATTACCCTTTGTTGGAAAGTCTCAATTGCCCT
TTGGTCTTCTGAGACTGTATCCTTGATATTTTTGGAGTAGACCAGAGTGTCGTGCTCCACCATGTTGACGAAGATTTTCT
TCTTGTCATTGAGTCGTAAGAGACTCTGTATGAACTGTTCGCCAGTTTTCACGGCGAGTTCTGTTAGATCCTCGATTTGA
ATCTTTGACTCCATGGCCTTTGATTCAGTAGGAACTACTTTTTTAGAGACTCCAATCTCTATTACTTGCCTTGGTTTATG
AAGCAAGCCTTGAATCGTCCATACTGGAATAGTACTTCTGATCTTGAGAAATATATCTTTCTCTGTGTTCTTGATGCAGT
TAGTCCTGAATCTTTTGACTGCATCTTTAACCTTCTTGGGAAGGTATTTGATCTCCTGGAGATTATTACTCGGGTAGATC
GTCTTAATGAGACCTGCTGCGTAGGCCTCTCTAACCATCTGTGGGTTAGCGTTCTTTCTGAAATTGAAGAGGCTAATCTT
CTCATTATCAGTGGTGAACATAGTATCGTCACCTTCACCGTCGAACTTTCTTCCTAGATCGTAGAGATAGAGGAAGTCGT
CCATTGTAATCTCCGGGGCAAAGGAGATCCATGGCTACTCAACGAAGGGCAAACCCTAGCTCTCTCCATCTAATTACTGT
ATTCTCTCTGCTCGTCGCTGTCGTCTCCGCTCAGGACGACTACCGTTACATCCATTTCTTGACTCAGCACTACGACGCTA
AGCCTAAGGGAAGAAACGATGAGTACTGCTTCAACATGATGAAGAACAGAAGGCTTACCAGGCCTTGCAAGGATAGAAAC
ACTTTCATCCACGGAAACAAGAACGACATCAAGGCTATCTGCGAGGATAGAAACGGACAACCTTACAGAGGTGATCTCAG
GATCTCTAAGTCTGAGTTCCAGATCACTATCTGCAAGCACAAGGGTGGAAGCTCTAGACCTCCTTGTAGATACGGTGCTA
CTGAGGATTCTAGAGTTATCGTTGTTGGATGCGAGAACGGACTTCCTGTTCATTTCGATGAGTCTTTCATCACCCCTAGG
CACTAActgcaggcatgcccgctgaaatcaccagtctctctctacaaatctatctctctataataatgtgtgagtagt
tcccagataagggaattagggttcttatagggtttcgctcatgtgttgagcatataagaaacccttagtatgtatttgta
tttgtaaaatacttctatcaataaaatttctaattcctaaaaccaaatccaggggtaccgagctc
```

FIGURE 32

```
GAATTCCTACAATGTTGAATAAACGTAGGTAGTGGCTACTTAATTTCTTCGATTTCTTAAGTGCTTAGTACTTTTCAACA
TTAAAAATGTTGTTACCAAGTCTAAATTTTCTTCACAACTTGTAACTAAACTTTTCATTATGTGTAATCGTAAAGGATTA
GCGCTACAAATAGATGGTGATTCCCTTCTAATGGACGAGTTGACATTGACGCATTATGTCTCTGGTTAGCTAGTCCGACG
TTTGAACAAGTACTCTTACCGCTCTCGAAACAAAATTAAAACCAAAATTTTATAGATCTATTAGTAAAATCTACTATTGT
TAATTTTATCACATAGTCCATGTGTGTGTTAATATTAAGGATGAAGTCAATGTATATATATATATCAAATCTCTATTCCT
ACTAGATATGGGAATCACCTACTTGTATAAATGGCAAACTCATTCAACGAGCTACACACGACTTTTCCAACTTATTTCAG
TGTTTGAGATCATTTTAATGCAACAACTATATGTTAAAGGGAAATTGGTCTAGAAGCGGCTATTTCTTGGTCTTGAAATC
ATATTGTTCTTCTATAGTGTAGTGACATTTCCTATAATTAATTTGAAAAAAGGAAGAAATTGTGTTGGCAATGAAAACAT
CATATGTATGGTGTGAAGTATATACAAAAAAAAAATCCCATTCGTGAATGAAAACTACGGTGTATATATGTGAAAGACAT
ATATGGAGCCTTCACTATACGGTGTAGTTCATTTACATAAGAATGGTTGGAAATGGAGATGCCATATTTTTTTATTTTT
TTTTTCCACAATGGAGATGCCATATCTATAAAAAAAGAAAAGAGGTTGAACTAGTTGGGTCGGCGCGACGAAAAGAGAAA
ATACAACTTGCTGGGCTAAATCTAGAAATTTCCATTTCTGTAAATGCCTTAAATTAATGGCTCTTATTTATCAAATACGG
GACAAACCCTCTTTACACCTTACAAGTTACGGGTATAGGGTGTTTATTCTCCCGTACCCGTTCAAACTACACTATATAAT
AAACCATTGACATTGTAGACCTATTACACATCCTGCAGTTATTGGCTTATTGCGATCTTTATTAAATCCAAAGATACATA
CTATATCGAAGAAACAAAAAGTCAAGAAATAATAAAACGAAAATAAATGAAGGCATCAATAAAAGCTTACCGCTCACATG
TTTATTTTCTAATAACTAATTTTTATTTAAAAAGCAGTTTATACATCTACCAAATTTATTTCTTAGCATAAATATATATT
TGGGTTTTGACTTTTAAGTTCTTTCTGACTTCTGAGTGATAATCACCAGTTTGCAACTTATATTTGCCTAAACCGCATGC
CAATTGTCATGTATCGTATCTAGTAATGGTATTAATGACGAGGATCCCAAAATTTAAATTCCACTTTCCAAGCATTGAGC
TCTTTAAACAATTCATGGTCAACTTAATTACAAGGAAAAAAAGAACTTATTGTTATAGTGGAACAGCTATTTTTTGGA
TATTAAAAGAATAATAACAGCAAAACAGAATTATCGTGTCCTAATAATACCTAAGGTCCTAAACGAAGCAAAAAAGTTGG
TAAATAAGGAAGAGAAAACCTACAAGATATTAAAACGGTGTCGTTGTTCGGAAGAATATACCGAAGTAGCAAAAGGAATA
TCTCATTAGAGAGTCCCTTATAAATGACCGTTTTAATACACTTCAACTCTGTCCTTGTTCATAGGCAGCTTCAACGATCA
TTCCACTTCCTTCTTCCTCTCTCAACATTTTCCCCTGAAAATAAGGAAACTAAAGATTCTTCCTCTCTCTTTCTACAC
TCTTCTGACAATACTAAAACACTTTATCAGATCAGATGGCTACTCAACGAAGGGCAAACCCTAGCTCTCTCCATCTAATT
ACTGTATTCTCTCTGCTCGTCGCTGTCGTCTCCGCTCAGGACGACTACCGTTACATCCATTTCTTGACTCAGCACTACGA
CGCTAAGCCTAAGGGAAGAAACGATGAGTACTGCTTCAACATGATGAAGAACAGAAGGCTTACCAGGCCTTGCAAGGATA
GAAACACTTTCATCCACGGAAACAAGAACGACATCAAGGCTATCTGCGAGGATAGAAACGGACAACCTTACAGAGGTGAT
CTCAGGATCTCTAAGTCTGAGTTCCAGATCACTATCTGCAAGCACAAGGGTGGAAGCTCTAGACCTCCTTGTAGATACGG
TGCTACTGAGGATTCTAGAGTTATCGTTGTTGGATGCGAGAACGGACTTCCTGTTCATTTCGATGAGTCTTTCATCACCC
CTAGGCACTAActgcaggcatgcccgctgaaatcaccagtctctctctacaaatctatctctctataataatgtgtga
gtagttcccagataagggaattagggttcttatagggtttcgctcatgtgttgagcatataagaaacccttagtatgtat
ttgtatttgtaaaatacttctatcaataaaatttctaattcctaaaaccaaaatccaggggtaccgagctc
```

FIGURE 33

```
ATTGTTTTCATAGAAGTTTGTCGAAAACATCGTTTTTCAGTAAAAAAATCATAAAGCACTGAAATATCGATTGACATACT
TTTAACAAGAAAACTAACAATAGGGCCCGGTCGTCAGGCCTACGTGGCACCAGGTGACAGCCCGCAGAGACAATGTTTGT
CTGGTCCATTAAAAAGAAAAGAAGGCCCACCTGTCAGCTGCCCAGCCCACTAGCAGTCATCTTCAACCTTCTGCCAGAAG
GAAAAAGTTGAGTCGCGTGCACAGAGAAGCTGCCACCTCCGGCCTGCCTGGATCCCAAGCCTCATTCCCTTCGCCAGTGA
TGCTGCATAAACCTGCTCCGCCAATCCCCGTCGCTCACAGATTCCCTCTCACAGTCTTACTCTCCTGCTCGAATCCCCAT
CTTAGTCCACAGCATGCCGTCGGCGTCTTCCTTCGCCCGTGCGACTACTAGCCTCCCCTCCCCCGTGAGCATCCCCCACC
AGAGGATTTGGATCGAGGCATCCTGTAGGAAGCGCAAGTCGTTATGGTGCTCGCCTCTGACCATCGGTCCCTCGCTCCGA
TTCATCGATGTTGCTAATCCACGACGCCTCCTCTCGCTATCACACACAACGCGTTGGCCTTGCCAAGCCTCTGATGTCGT
GCGTGACAAGCCTCGCAACTCCATGCTTTGTCGCCAACACCGTCTGCTCCGGCCACCGCCGTCAACATAAAGGACGACAC
TCCCAGGCATCCCCGGCTGGCCCGACCAGACGAACGTGCTCAAGGTGAGCAGCCGGTTCTTCCCTCTCTACTTCCTTCTC
CATTTGCACCCTCCGGAGAGCCTCCGATGACGACCGTGCCTCGGCCGCCACTCTGCTCCGCCACGAGCTCGATGTGGGCA
TGGCTACTCAACGAAGGGCAAACCCTAGCTCTCTCCATCTAATTACTGTATTCTCTCTGCTCGTCGCTGTCGTCTCCGCT
CAGGACGACTACCGCTACATCCACTTTCTCACCCAGCACTACGACGCCAAGCCAAAGGGCCGCAACGACGAGTACTGCTT
CAACATGATGAAGAACCGCCGCCTCACCCGCCCATGCAAGGACCGCAACACCTTCATCCACGGCAACAAGAACGACATCA
AGGCCATCTGCGAGGACCGCAACGGCCAGCCATACAGGGGCGACCTCCGCATCTCCAAGTCCGAGTTCCAGATCACCATC
TGCAAGCACAAGGGCGGCTCCTCCCGCCCACCATGCAGGTACGGCGCCACCGAGGACTCCCGCGTGATCGTGGTGGGCTG
CGAGAACGGCCTCCCAGTGCACTTCGACGAGTCCTTCATCACCCCACGCCACTGActgcaggcatgcccgctgaaatcac
cagtctctctctacaaatctatctctctctataataatgtgtgagtagttcccagataagggaattagggttcttatagg
gtttcgctcatgtgttgagcatataagaaacccttagtatgtatttgtatttgtaaaatacttctatcaataaaatttct
aattcctaaaaccaaaatccaggggtaccgagctc
```

FIGURE 34

```
CCCAACCTCGGTCTTGGTCACACCAGGAACTCTCTGGTAAGCTAGCTCCACTCCCCAGAAACAACCGGCGCCAAATTGCG
CGAATTGCTGACCTGAAGACGGAACATCATCGTCGGGTCCTTGGGCGATTGCGGCGGAAGATGGGTCAGCTTGGGCTTGA
GGACGAGACCCGAATCCGAGTCTGTTGAAAAGGTTGTTCATTGGGGATTTGTATACGGAGATTGGTCGTCGAGAGGTTTG
AGGGAAAGGACAAATGGGTTTGGCTCTGGAGAAAGAGAGTGCGGCTTTAGAGAGAGAATTGAGAGGTTTAGAGAGAGATG
CGGCGGCGATGAGCGGAGGAGAGACGACGAGGACCTGCATTATCAAAGCAGTGACGTGGTGAAATTTGGAACTTTTAAGA
GGCAGATAGATTTATTATTTGTATCCATTTTCTTCATTGTTCTAGAATGTCGCGGAACAAATTTTAAAACTAAATCCTAA
ATTTTTCTAATTTTGTTGCCAATAGTGGATATGTGGGCGTATAGAAGGAATCTATTGAAGGCCCAAACCCATACTGACG
AGCCCAAAGGTTCGTTTTGCGTTTTATGTTTCGGTTCGATGCCAACGCCACATTCTGAGCTAGGCAAAAAACAAACGTGT
CTTTGAATAGACTCCTCTCGTTAACACATGCAGCGGCTGCATGGTGACGCCATTAACACGTGGCCTACAATTGCATGATG
TCTCCATTGACACGTGACTTCTCGTCTCCTTTCTTAATATATCTAACAAACACTCCTACCTCTTCCAAAATATATACACA
TCTTTTTGATCAATCTCTCATTCAAAATCTCATTCTCTCTAGTAAACAAGAACAAAAAAATGGCGGATACAGCTAGAGGA
ACCCATCACGATATCATCGGCAGAGACCAGTACCCGATGATGGGCCGAGACCGAGACCTACCAGATGTCCGGACGAGG
ATCTGACTACTCCAAGTCTAGGCAGATTGCTAAAGCTGCAACTGCTGTCACAGCTGGTGGTTCCCTCCTTGTTCTCTCCA
GCCTTACCCTTGTTGGAACTGTCATAGCTTTGACTGTTGCAACACCTCTGCTCGTTATCTTCAGCCCAATCCTTGTCCCG
GCTCTCATCACAGTTGCACTCCTCATCACCGGTTTTCTTTCCTCTGGAGGGTTTGGCATTGCCGCTATAACCGTTTTCTC
TTGGATTTACAAGTACGCAACGGGAGAGCACCCACAGGGATCAGACAAGTTGGACAGTGCAAGGATGAAGTTGGGAAGCA
AAGCTCAGGATCTGAAAGACAGAGCTCAGTACTACGGACAGCAACATACTGGTGGGAACATGACCGTGACCGTACTCGT
GGTGGCCAGCACACTACTCTTGTTCCTCGTGGATCTCAGGACGACTACCGTTACATCCATTTCTTGACTCAGCACTACGA
CGCTAAGCCTAAGGGAAGAAACGATGAGTACTGCTTCAACATGATGAAGAACAGAAGGCTTACCAGGCCTTGCAAGGATA
GAAACACTTTCATCCACGGAAACAAGAACGACATCAAGGCTATCTGCGAGGATAGAAACGGACAACCTTACAGAGGTGAT
CTCAGGATCTCTAAGTCTGAGTTCCAGATCACTATCTGCAAGCACAAGGGTGGAAGCTCTAGACCTCCTTGTAGATACGG
TGCTACTGAGGATTCTAGAGTTATCGTTGTTGGATGCGGAGAACGGACTTCCTGTTCATTTCGATGAGTCTTTCATCACCC
CTAGGCACTAActgcaggcatgcccgctgaaatcaccagtctctctctacaaatctatctctctctataatgtgtga
gtagttcccagataagggaattagggttcttatagggtttcgctcatgtgttgagcatataagaaacccttagtatgtat
ttgtatttgtaaaatacttctatcaataaaatttctaattcctaaaaccaaaatccaggggtaccgagctc
```

FIGURE 35

GCTCCCCCGCCGTCGTTCAATGAGAATGGATAAGAGGCTCGTGGGATTGACGTGAGGGGGCAGGGATGGCTATATTTCTG
GGAGCGAACTCCGGGCGAATACGAAGCGCTTGGATACAATGCAGGACGACTACCGTTACATCCATTTCTTGACTCAGCAC
TACGACGCTAAGCCTAAGGGAAGAAACGATGAGTACTGCTTCAACATGATGAAGAACAGAAGGCTTACCAGGCCTTGCAA
GGATAGAAACACTTTCATCCACGGAAACAAGAACGACATCAAGGCTATCTGCGAGGATAGAAACGGACAACCTTACAGAG
GTGATCTCAGGATCTCTAAGTCTGAGTTCCAGATCACTATCTGCAAGCACAAGGGTGGAAGCTCTAGACCTCCTTGTAGA
TACGGTGCTACTGAGGATTCTAGAGTTATCGTTGTTGGATGCGAGAACGGACTTCCTGTTCATTTCGATGAGTCTTTCAT
CACCCCTAGGCACTAAgatcctggcctagtctataggaggttttgaaaagaaaggagcaataatcatttcttgttctat
caagagggtgctattgctcctttctttttttcttttattattactagtattttacttacatagacttttttgtttac
attatagaaaaagaaggagaggttattttcttgcatttattcatgattgagtattctatttgatttgtatttgtttaa
aattgtagaaatagaacttgtttctcttcttgctaatgttactatatcttttgatttttttttccaaaaaaaaaatca
aattttgacttcttcttatctcttatctttgaatatctcttatctttgaataataatatcattgaaataagaagaaga
gctatattcga
```

FIGURE 36

A.
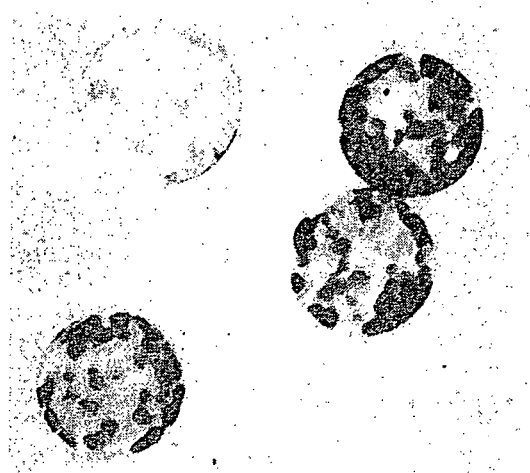
B.
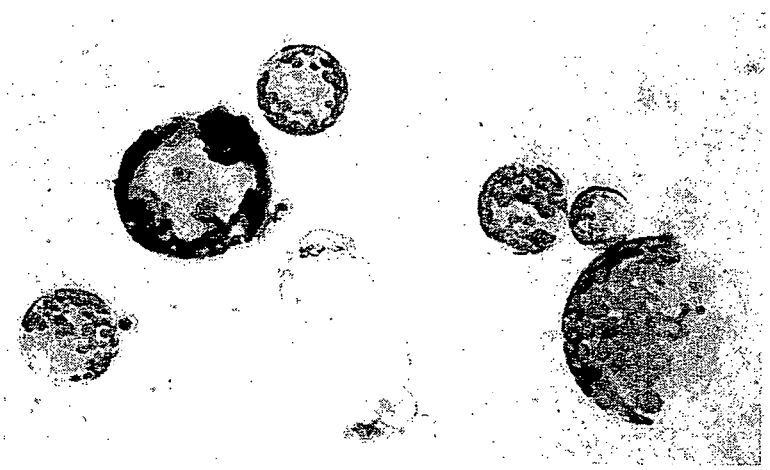
C.
FIGURE 37

A.
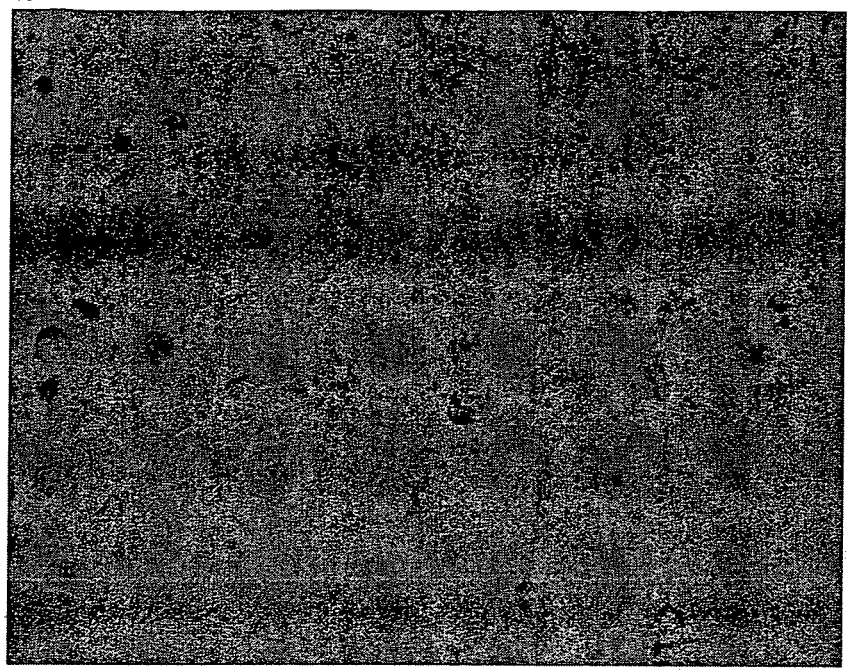
B.
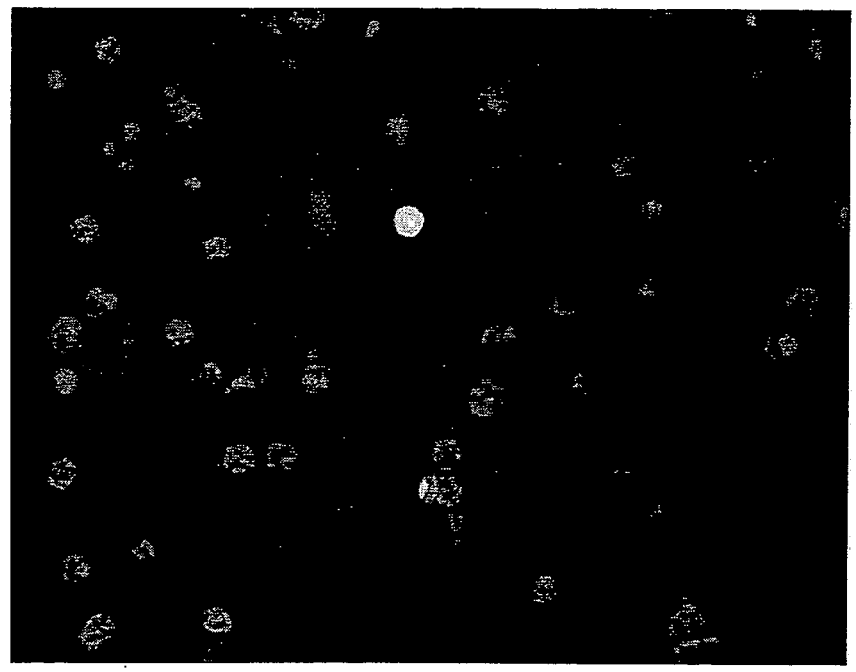
FIGURE 38

A.
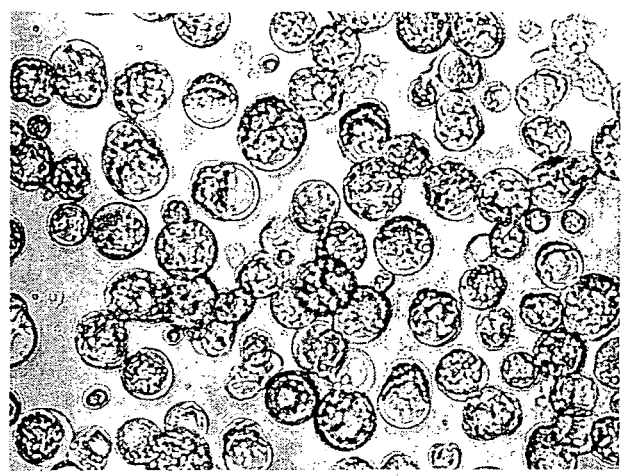
B.
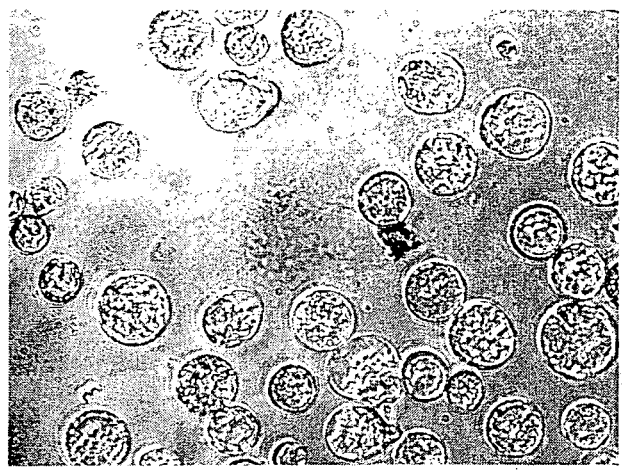
C.
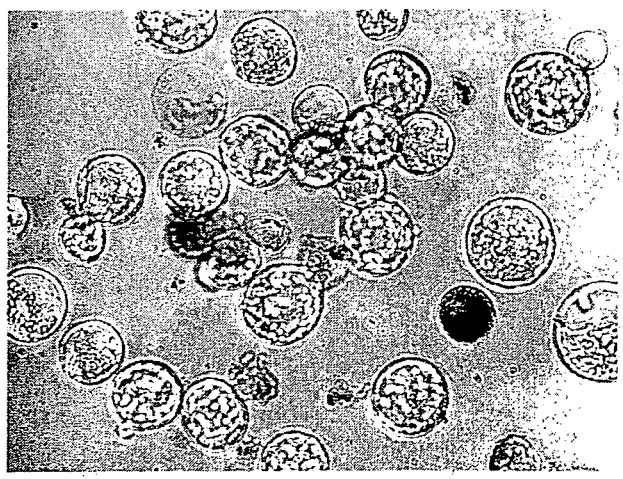
FIGURE 40

A.
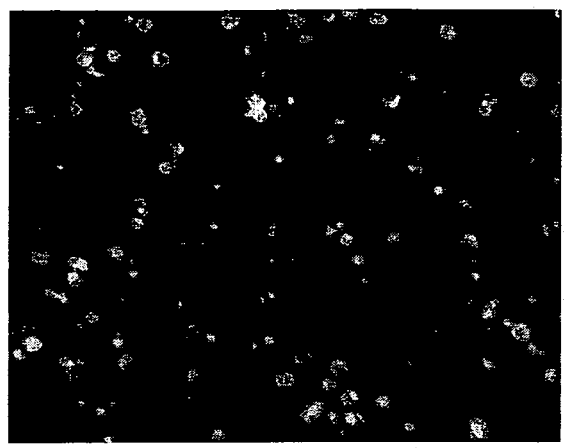
B.
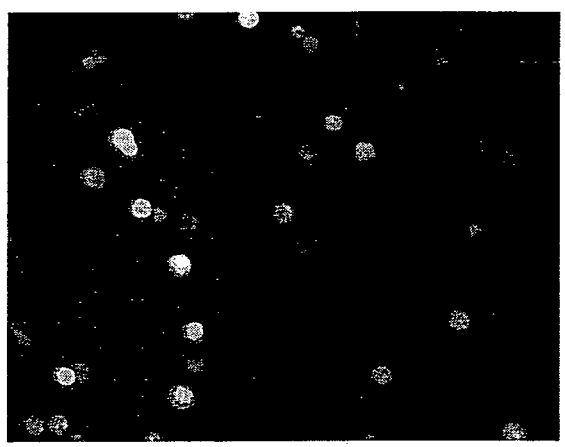
FIGURE 41

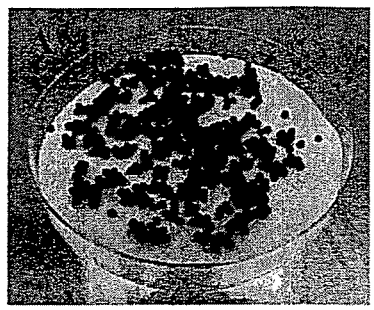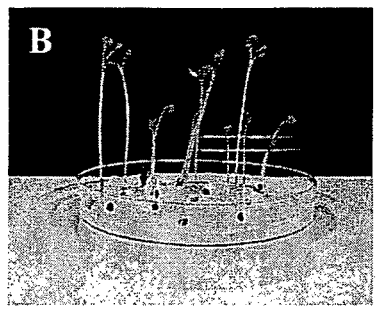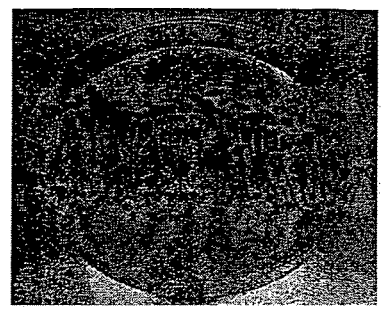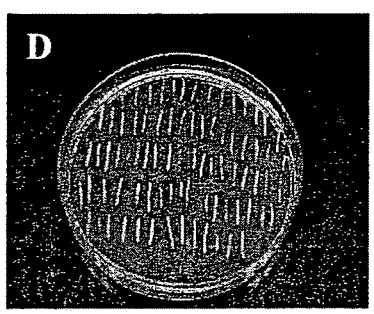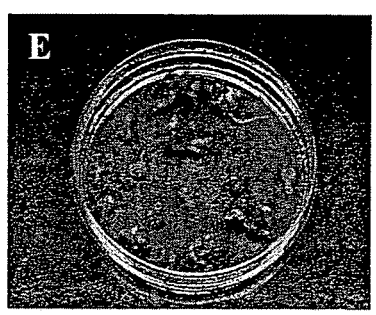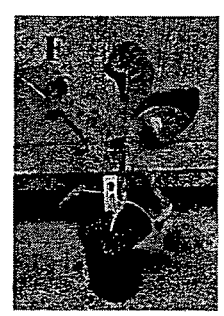
FIGURE 43

AQDDYRYIHFLTQHYDAKPKGRNDEYCFNMMKNRRLTRPCKDRNTFIHGNKNDIKAICEDRNGQPYRGDLRISKSEFQIT
ICKHKGGSSRPPCRYGATEDSRVIVVGCENGLPVHFDESFITPRH

FIGURE 50

… # ANGIOGENIN EXPRESSION IN PLANTS

FIELD OF THE INVENTION

The present invention relates to plant-produced angiogenins, to related plant cells, plant calli, plants, seeds and other plant parts and products derived therefrom and to uses of plant-produced angiogenins.

The present invention also relates to expression of angiogenin genes in plants and to related nucleic acids, constructs and methods.

BACKGROUND OF THE INVENTION

Angiogenin, encoded by the ANG gene, is a member of the ribonuclease (RNase) superfamily. Angiogenin (also known as RNase5) is a 14 kDa, non-glycosylated secreted ribonuclease polypeptide. Angiogenin is known to regulate the formation of new blood vessels through a process called angiogenesis and is known to regulate neuron survival with functional mutations in the protein a cause of the neuromuscular disorder amyotrophic lateral sclerosis (ALS).

During angiogenisis, the angiogenin protein binds to receptors on the surface of endothelial cells and smooth muscle cells and undergoes nuclear translocation where it stimulates the production of ribosomal RNA (rRNA) which is required for the growth and division of cells for capillary formation. Angiogenesis associated with exercise causes capillary growth that allows for greater nutrient and oxygen delivery to muscle tissue.

In our co-pending application PCT/AU2009/000603 we demonstrated that angiogenin increases muscle cell growth and differentiation in vitro, and significantly alleviates the potent inhibitory effects of myostatin on myoblasts. Angiogenin is enriched in colostrum and milk, secretions which evolved to promote health, growth and development of suckling mammals. When added to the feed of mice, angiogenin purified from bovine milk increased exercising muscle growth by 50% over a 4 week period. We demonstrated that angiogenin is bioavailable when administered orally in our co-pending application PCT/AU2009/000602.

Angiogenin has also been shown to possess a number of other activities. These include the ability to remove skin defects such as pigmented spots, modulation of immune responses, protection of polymorphonuclear leukocytes from spontaneous degradation, and microbicidal activity against systemic bacterial and fungal pathogens. Angiogenin also appears to be required for effective activity of growth factors such as VEGF, EGF and FGF. In addition, functional mutations in the angiogenin protein cause the neuromuscular disorder amyotrophic lateral sclerosis (ALS).

Angiogenin may have numerous applications, including applications in medicine, dietary foodstuff supplements and cosmetics. However, the use of angiogenin in such applications requires an efficient process for the preparation of the protein on a commercial scale from an appropriate source.

Angiogenin is readily available in bovine milk, however its use as a source of angiogenin is not favoured as angiogenin is only present in bovine milk at a low level. Also, certain proteins, such as caseins, and milk whey proteins such as immunoglobulin, lactoferrin and lactoperoxidase present in milk mask angiogenin, hindering its purification.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

It is an object of the present invention to overcome, or at least alleviate, one or more of the difficulties or deficiencies associated with the prior art.

SUMMARY OF THE INVENTION

In a first aspect, the present invention provides a plant cell, plant callus, plant, seed or other plant part including an angiogenin gene or a functionally active fragment or variant thereof and/or an angiogenin polypeptide.

In a second aspect, the present invention provides methods of using plant cells, plant calli, plants, seeds or other plant parts including an angiogenin, for example as feed stock or for human consumption.

In a further aspect, the present invention provides a plant-produced angiogenin.

In a further aspect, the present invention provides a feedstock, food supplement or veterinary product including a plant-produced angiogenin.

In a further aspect, the present invention provides a food, beverage, food supplement, nutraceutical or pharmaceutical including a plant-produced angiogenin.

In a further aspect the present invention provides a method for producing a transformed plant cell expressing an angiogenin gene.

In a further aspect, the present invention provides methods of isolating angiogenin from transformed plant cells.

In a further aspect, the present invention provides methods of regenerating transformed plant calli, plants, seeds or other plant parts from transformed plant cells.

In a still further aspect, the present invention provides methods of isolating angiogenin from transformed plant calli, plants, seeds or other plant parts.

In a still further aspect, the present invention provides methods of enhancing expression, activity or isolation of angiogenin in plants, said methods comprising co-expressing angiogenin with a mediator or modulator of angiogenin activity.

In a still further aspect, the present invention provides an artificial construct including an angiogenin gene, said construct enabling expression of said angiogenin gene in a plant cell.

In a still further aspect, the present invention provides artificial constructs or chimeric sequences comprising an angiogenin gene and a gene encoding a mediator or modulator of angiogenin activity.

In a still further aspect, the present invention provides a chimeric sequence comprising an angiogenin gene and a plant signal peptide.

In a still further aspect, the present invention provides an angiogenin gene with codon usage adapted for plants to enable expression of said angiogenin gene in a plant cell.

As used herein, except where the context requires otherwise, the term "comprise" and variations of the term, such as "comprising", "comprises" and "comprised", are not intended to exclude further additives, components, integers or steps.

As used herein, except where the context requires otherwise, the singular forms "a", "an" and "the" include plural aspects.

BRIEF DESCRIPTION OF THE DRAWINGS/FIGURES

FIG. 1. Nucleotide sequence of the *Bos taurus* angiogenin, ribonuclease, RNase A family, 5 (ANG) (SEQ ID NO:

1). NCBI Accession NM_001078144. The 72 bp signal peptide sequence identified by NCBI is in bold and underlined.

FIG. 2. Amino acid sequence of the *Bos taurus* angiogenin, ribonuclease, RNase A family, 5 (ANG) (SEQ ID NO: 2). NCBI Accession NP_001071612. The 24 aa signal sequence identified by NCBI is in bold and underlined. The angiogenin receptor binding domain is highlighted in black and the active site residues are highlighted in grey. The Asp (D) amino acid highlighted in bold and underlined is a possible site for mutation to enhance angiogenin activity.

FIG. 3. Nucleotide sequence of the *Bos taurus* angiogenin, ribonuclease, RNase A family, 5 (ANG) (SEQ ID NO: 3) modified for plant codon bias as defined by Murray et al., (1989). No changes in amino acid sequence to that outlined in FIG. 2 were observed.

FIG. 4. Nucleotide sequence alignment of representative angiogenin genes from different organisms (SEQ ID NOS: 4-12).

FIG. 5. Amino acid sequence alignment of representative angiogenin genes from different organisms (SEQ ID NOS: 13-21).

FIG. 6. Nucleotide sequence of the *Bos taurus* angiogenin, ribonuclease, RNase A family, 5 (ANG), minus its signal peptide sequence, modified for monocot plant codon bias (SEQ ID NO: 22).

FIG. 7. Nucleotide sequence of the *Bos taurus* angiogenin, ribonuclease, RNase A family, 5 (ANG), minus its signal peptide sequence, modified for dicot plant codon bias (SEQ ID NO: 23).

FIG. 8. Nucleotide sequence alignment, indicating 80.7% similarity, between ANG modified for monocot (SEQ ID NO: 22) and dicot (SEQ ID NO: 23) plant codon bias. No changes in amino acid sequence to that outlined in FIG. 2 were observed.

FIG. 9. Nucleotide sequence of *Arabidopsis* oleosin_ANG fusion gene (SEQ ID NO: 24). The *Arabidopsis* olesin gene is indicated in plain UPPERCASE. The thrombin protease recognition site is highlighted in black followed by the ANG gene in underlined UPPERCASE font. The start and stop codons are highlighted in grey.

FIG. 10. Amino acid sequence of the *Arabidopsis* oleosin_ANG fusion protein (SEQ ID NO: 25). The *Arabidopsis* olesin protein is indicated in plain UPPERCASE. The thrombin protease recognition site is highlighted in black italics followed by the ANG protein in underlined UPPERCASE font.

FIG. 11. Nucleotide sequence of an expression cassette containing the ANG gene with an ER signal retention peptide regulated by the AtRbcS light regulated promoter and nopaline synthase (nos) terminator for accumulation in dicot plant tissue (SEQ ID NO: 26). The expression cassette contains the dicot optimised ANG gene sequence outlined in FIG. 7. The AtRbcS promoter is indicated in UPPERCASE italics, the ANG gene is in plain UPPERCASE with the ER signal retention peptide UNDERLINED and the start and stop codon highlighted in grey. The nos terminator is presented in lowercase.

FIG. 12. Vector map of sequence outlined in FIG. 11 containing the ANG gene with an ER signal retention peptide regulated by the AtRbcS light regulated promoter and nos terminator for transfection and accumulation in dicot plant tissue.

Figure 13:
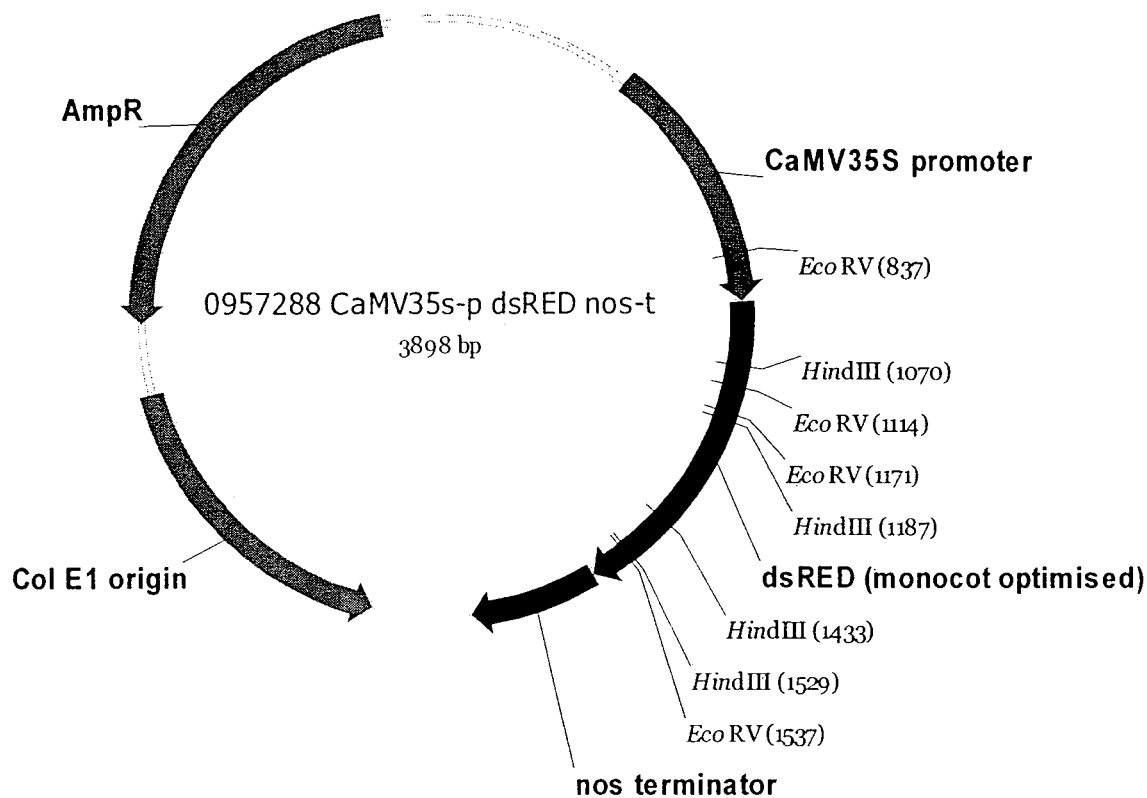

FIG. 13. Vector map of a control expression cassette designed to express the fluorescent reporter (turboGFP) under control of the constitutive CaMV35s promoter from the plant Cauliflower Mosaic virus (CaMV) for confirmation of expression in dicot plant tissue.

FIG. 14. Nucleotide sequence of an expression cassette containing the ANG gene with an ER signal retention peptide regulated by the TaRbcS light regulated promoter and nopaline synthase (nos) terminator for accumulation in monocot plant tissue (SEQ ID NO: 27). The expression cassette contains the monocot optimised ANG gene sequence outlined in FIG. 6. The TaRbcS promoter is indicated in UPPERCASE italics, the ANG gene is in plain UPPERCASE with the ER signal retention peptide UNDERLINED and the start and stop codon highlighted in grey. The nos terminator is presented in lowercase.

Figure 15:
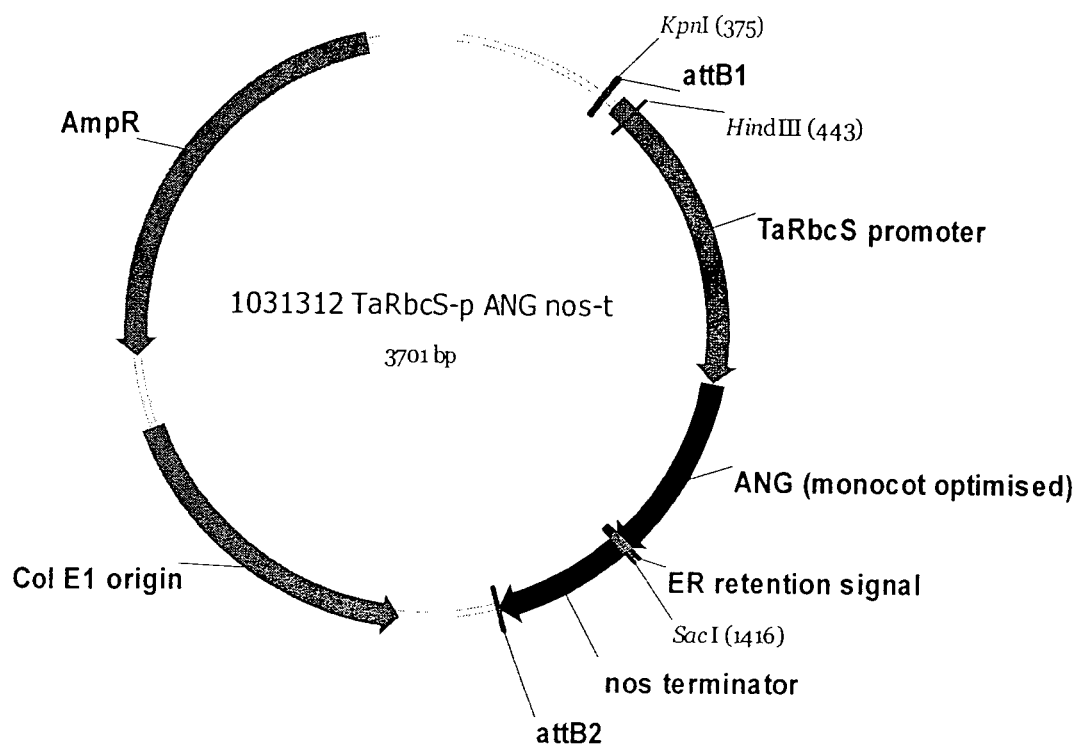

FIG. 15. Vector map of sequence outlined in FIG. 14 containing the ANG gene with an ER signal retention peptide regulated by the TaRbcS light regulated promoter and nos terminator for accumulation in monocot plant tissue.

Figure 16:
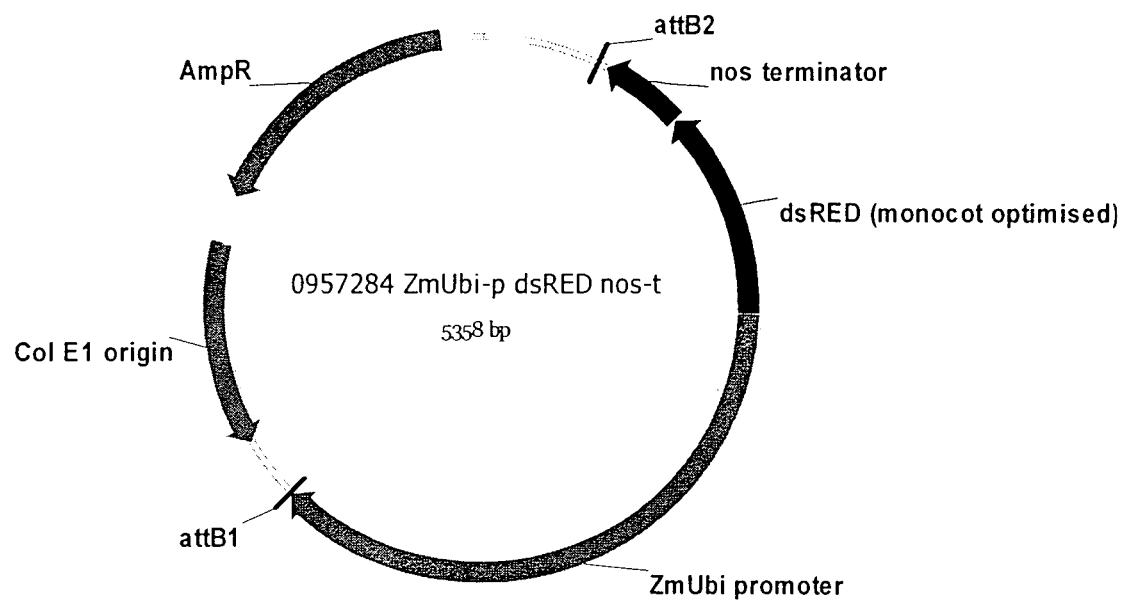

FIG. 16. Vector map of a control expression cassette designed to express the fluorescent reporter (dsRED) under control of the constitutive ubiquitin promoter from *Zea mays* (ZmUbi) for confirmation of expression in monocot plant tissue.

FIG. 17. Nucleotide sequence of an expression cassette containing the ANG gene with an ER signal retention peptide regulated by the AtRbcS light regulated promoter and CaMV35S terminator for transformation and accumulation in dicot plant tissue (SEQ ID NO: 28). The expression cassette contains the ANG gene sequence outlined in FIG. 3. The AtRbcS promoter is indicated in UPPERCASE ITALICS, the ANG gene is in plain UPPERCASE with the ER signal retention peptide UNDERLINED and the start and stop codon highlighted in grey. The CaMV35S terminator is presented in lowercase.

Figure 18:
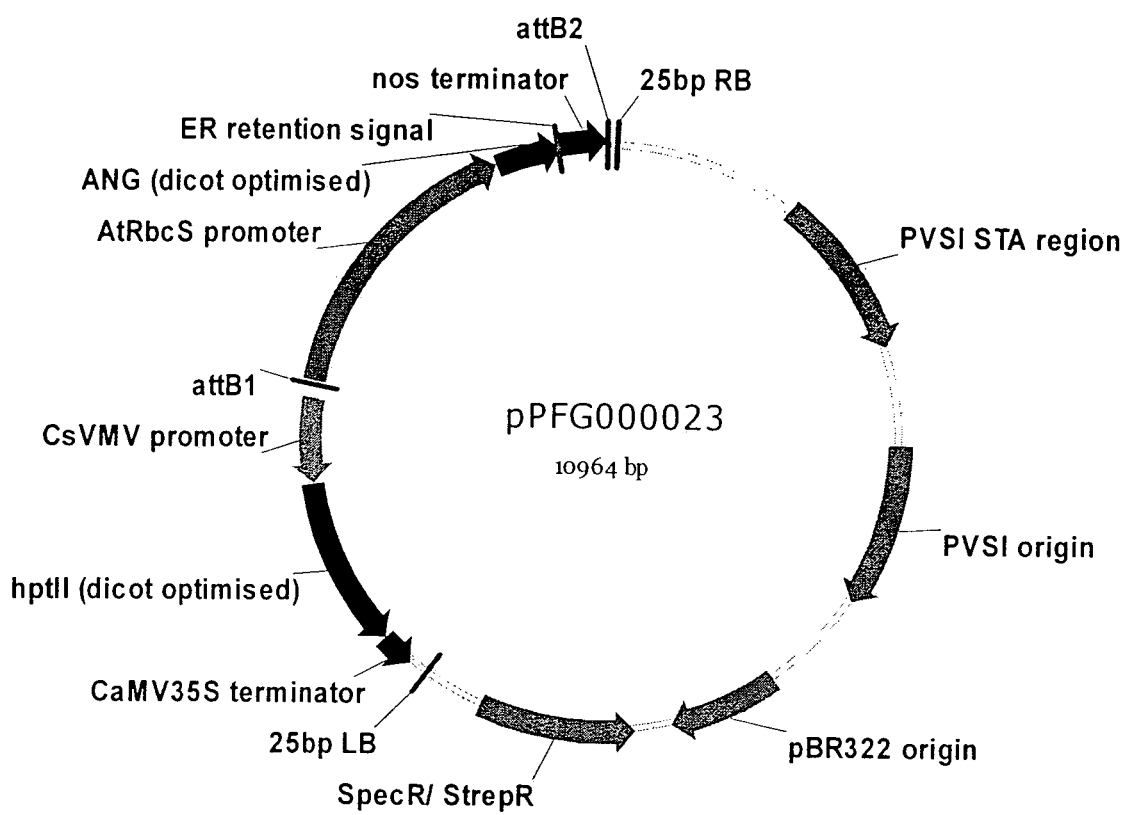

FIG. 18. Vector map of sequence outlined in FIG. 11 containing the ANG gene with an ER signal retention peptide regulated by the AtRbcS light regulated promoter and nos terminator for transformation and accumulation in monocot plant tissue. The base vector sequence contains the necessary elements for *Agrobacterium*-mediated transformation and regeneration under appropriate selection.

FIG. 19. Representative nucleotide sequence of an expression cassette containing the ANG gene with an ER signal retention peptide regulated by the TaRbcS light regulated promoter and terminator for accumulation in monocot plant tissue (SEQ ID NO: 29). The expression cassette contains the ANG gene sequence outlined in FIG. 6. The TaRbcS promoter is indicated in UPPERCASE italics, the ANG gene is in plain UPPERCASE with the ER signal retention peptide UNDERLINED and the start and stop codon highlighted in grey. The TaRbcS terminator is presented in lowercase.

Figure 20:
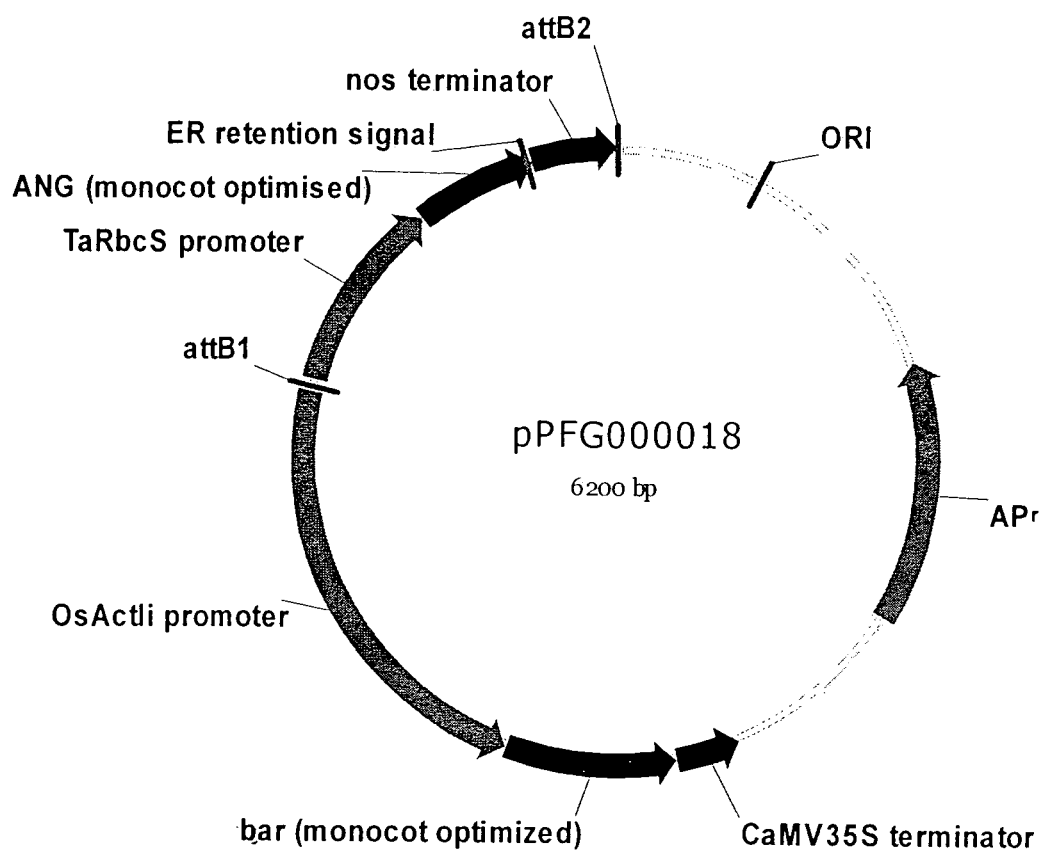

FIG. 20. Vector map of sequence outlined in FIG. 14 containing the ANG gene with an ER signal retention peptide regulated by the TaRbcS light regulated promoter and nos terminator for transformation and accumulation in dicot plant tissue. The base vector sequence contains the necessary elements for regeneration under appropriate selection.

FIG. 21. Representative nucleotide sequence of an expression cassette containing the ANG gene with an ER signal retention peptide regulated by the LpRbcS light regulated promoter and LpFT4 terminator for accumulation in monocot plant tissue (SEQ ID NO: 30). The expression cassette contains the ANG gene sequence outlined in FIG. 6. The LpRbcS promoter is indicated in UPPERCASE italics, the ANG gene is in plain UPPERCASE with the ER signal retention peptide UNDERLINED and the start and stop codon highlighted in grey. The LpFT4 terminator is presented in lowercase.

FIG. 22. Representative nucleotide sequence of an expression cassette containing the ANG gene with an ER signal retention peptide regulated by the *Brassica napus* napin gene seed specific promoter and CaMV35S terminator for accumulation in dicot seeds (SEQ ID NO: 31). The expression cassette contains the ANG gene sequence outlined in FIG. 7. The napin gene promoter is indicated in UPPERCASE italics, the ANG gene is in plain UPPERCASE with the ER signal retention peptide UNDERLINED and the start and stop codons highlighted in grey. The CaMV35S terminator is presented in lowercase.

FIG. 23. Nucleotide sequence of an expression cassette containing the ANG gene with an ER signal retention peptide regulated by the *Brassica napus* napin gene seed specific promoter and nos terminator for accumulation in dicot seeds (SEQ ID NO: 32). The expression cassette contains the ANG gene sequence outlined in FIG. 7. The Bn_napin gene promoter is indicated in UPPERCASE italics, the ANG gene is in plain UPPERCASE with the ER signal retention peptide UNDERLINED and the start and stop codons highlighted in grey. The nos terminator is presented in lowercase.

Figure 24:
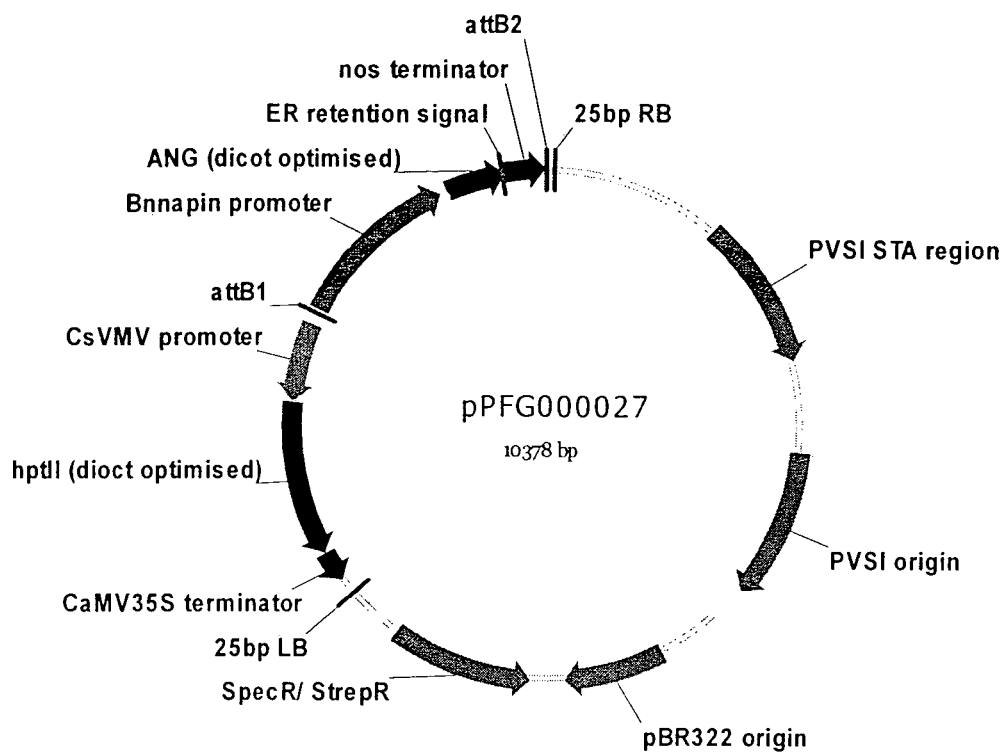

FIG. 24. Vector map of sequence outlined in FIG. 23 containing the ANG gene with an ER signal retention peptide regulated by the *Brassica napus* napin promoter and nos terminator for transformation and accumulation in dicot seed tissue. The base vector sequence contains the necessary elements for *Agrobacterium*-mediated transformation and regeneration under appropriate selection.

FIG. 25. Representative nucleotide sequence of an expression cassette containing the ANG gene with an ER signal retention peptide regulated by the *Zea mays* zein 4 gene seed specific promoter and CaMV35S terminator for accumulation in monocot seeds (SEQ ID NO: 33). The expression cassette contains the ANG gene sequence outlined in FIG. 6. The Zm zein promoter is indicated in UPPERCASE italics, the ANG gene is in plain UPPERCASE with the ER signal retention peptide UNDERLINED and the start and stop codons highlighted in grey. The CaMV35S terminator is presented in lowercase.

FIG. 26. Nucleotide sequence of an expression cassette containing the ANG gene with an ER signal retention peptide regulated by the *Zea mays* zein 4 gene seed specific promoter and nos terminator for accumulation in monocot seeds (SEQ ID NO: 34). The expression cassette contains the ANG gene sequence outlined in FIG. 6. The Zm_zein 4 gene promoter is indicated in UPPERCASE italics, the ANG gene is in plain UPPERCASE with the ER signal retention peptide UNDERLINED and the start and stop codons highlighted in grey. The nos terminator is presented in lowercase.

Figure 27:
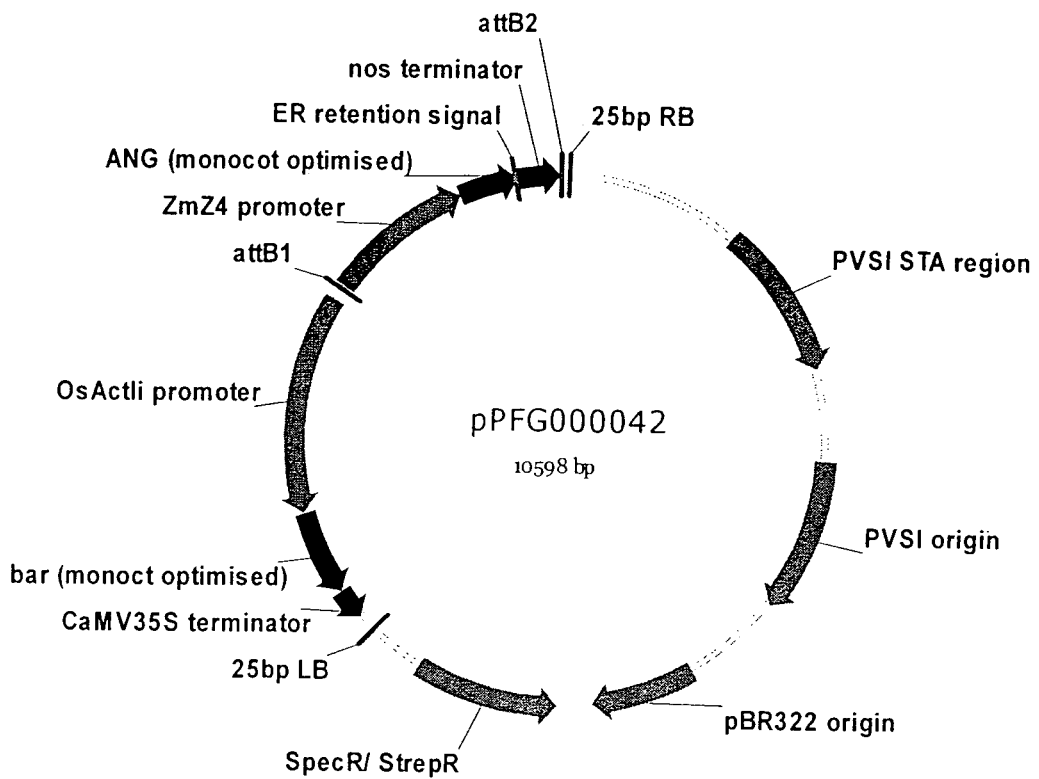

FIG. 27. Vector map of sequence outlined in FIG. 26 containing the ANG gene with an ER signal retention peptide regulated by the *Zea mays* zein 4 promoter and nos terminator for transformation and accumulation in monocot seed tissue. The base vector sequence contains the necessary elements for *Agrobacterium*-mediated transformation and regeneration under appropriate selection.

FIG. 28. Nucleotide sequence of an expression cassette containing the ANG gene with an ER signal retention peptide regulated by the *Orysa sativa* PR602 gene seed specific promoter and nos terminator for accumulation in monocot seeds (SEQ ID NO: 35). The expression cassette contains the ANG gene sequence outlined in FIG. 6. The PR602 gene promoter is indicated in UPPERCASE italics, the ANG gene is in plain UPPERCASE with the ER signal retention peptide UNDERLINED and the start and stop codons highlighted in grey. The nos terminator is presented in lowercase.

Figure 29:
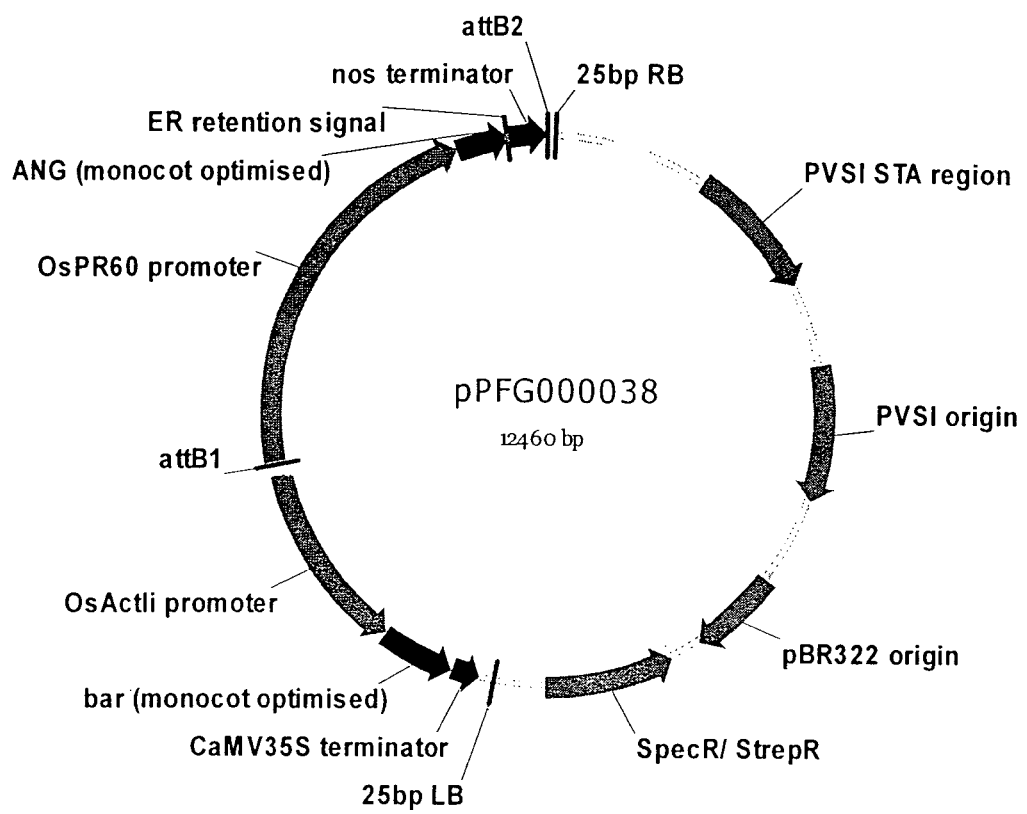

FIG. 29. Vector map of sequence outlined in FIG. 28 containing the ANG gene with an ER signal retention peptide regulated by the *Orysa sativa* PR602 promoter and nos terminator for transformation and accumulation in monocot seed tissue. The base vector sequence contains the necessary elements for *Agrobacterium*-mediated transformation and regeneration under appropriate selection.

FIG. 30. Nucleotide sequence of an expression cassette containing the ANG gene with an ER signal retention peptide regulated by the *Triticum aestivum* glutelin gene seed specific promoter and nos terminator for accumulation in monocot seeds (SEQ ID NO: 36). The expression cassette contains the ANG gene sequence outlined in FIG. 6. The glutelin gene promoter is indicated in UPPERCASE italics, the ANG gene is in plain UPPERCASE with the ER signal retention peptide UNDERLINED and the start and stop codons highlighted in grey. The nos terminator is presented in lowercase.

Figure 31:
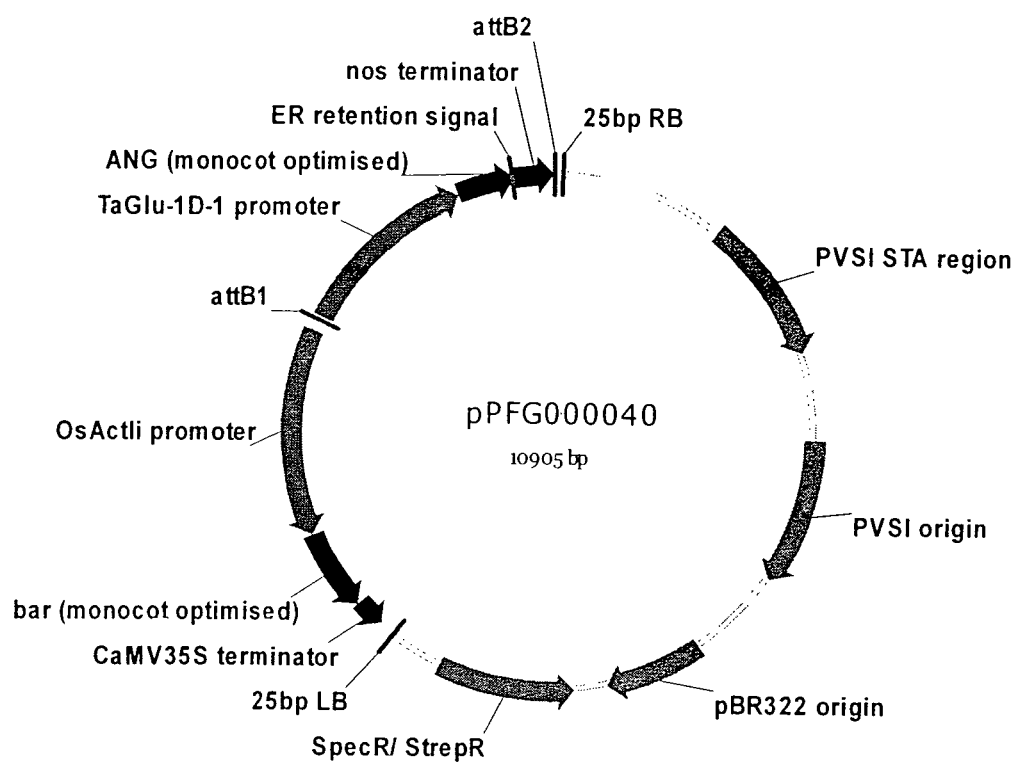

FIG. 31. Vector map of sequence outlined in FIG. 30 containing the ANG gene with an ER signal retention peptide regulated by the *Triticum aestivum* glutelin promoter and nos terminator for transformation and accumulation in monocot seed tissue. The base vector sequence contains the necessary elements for *Agrobacterium*-mediated transformation and regeneration under appropriate selection.

FIG. 32. Representative nucleotide sequence of an expression cassette containing the ANG gene with the tobacco calreticulin apoplast signal peptide regulated by the constitutive CaMV35S promoter and terminator for guttation secretion in plants (SEQ ID NO: 37). The expression cassette contains the ANG gene sequence outlined in FIG. 7. The CaMV35S promoter is indicated in UPPERCASE italics, the ANG gene is in plain UPPERCASE with the apoplast signal peptide UNDERLINED and the start and stop codons highlighted in grey. The CaMV35S terminator is presented in lowercase.

FIG. 33. Representative nucleotide sequence of an expression cassette containing the ANG gene with the tobacco calreticulin apoplast signal peptide regulated by the *Arabidopsis* phosphate transporter (AtPHT1) gene root-specific promoter and CaMV35S terminator for secretion in dicot roots (SEQ ID NO: 38). The expression cassette contains the ANG gene sequence outlined in FIG. 7. The AtPHT1 promoter is indicated in UPPERCASE italics, the ANG gene is in plain UPPERCASE with the apoplast signal peptide UNDERLINED and the start and stop codons highlighted in grey. The CaMV35S terminator is presented in lowercase.

FIG. 34. Representative nucleotide sequence of an expression cassette containing the ANG gene with the tobacco calreticulin apoplast signal peptide regulated by the *Hordeum vulgare* phosphate transporter (HvPHT1) gene root-specific promoter and CaMV35S terminator for secretion in monocot roots (SEQ ID NO: 39). The expression cassette contains the ANG gene sequence outlined in FIG. 6. The HvPHT1 promoter is indicated in UPPERCASE italics, the ANG gene is in plain UPPERCASE with the apoplast signal peptide UNDERLINED and the start and stop codons highlighted in grey. The CaMV35S terminator is presented in lowercase.

FIG. 35. Representative nucleotide sequence of an expression cassette containing an oleosin_ANG gene fusion regulated by the *Arabidopsis* oleosin gene promoter and CaMV35S terminator for targeting to the oilbody in dicots (SEQ ID NO: 40). The expression cassette contains the ANG gene sequence outlined in FIG. 7. The *Arabidopsis* oleosin gene promoter is indicated in UPPERCASE italics. The *Arabidopsis* olesin gene is indicated in plain UPPERCASE and the ANG gene in underlined UPPERCASE with the thrombin protease recognition site highlighted in black and the start and stop codons highlighted in grey. The CaMV35S terminator is presented in lowercase.

FIG. 36. Representative nucleotide sequence of an expression cassette containing the tobacco 16sRNA operon (Prrn) promoter and terminator regulatory sequences (Zoubenko, et al., 1994) to express the angiogenin gene in chloroplasts (SEQ ID NO: 41). The 16sRNA operon (Prrn) promoter is indicated in UPPERCASE italics, the ANG gene is in plain UPPERCASE and the start and stop codons highlighted in grey. The 16sRNA operon (Prrn) terminator is presented in lowercase.

FIG. 37. A. Mesophyll-derived protoplasts of *Nicotiana tabacum* recovered from in-vitro grown leaves approximately 4-6 weeks old; 0 days post transfection; B. Assessment of protoplasts vigour, with dead cells indicated by dark staining, showing greater than 95 percent viability using Evan's Blue Stain; pre-transfection; C. Assessment of protoplast vigour, with dead cells indicated by dark staining, showing greater than 95 percent viability using Evan's Blue Stain; 36 hours post-transfection.

FIG. 38. Assessment of transient expression 36 hours post transfection with plasmid DNA containing the turboGFP gene encoding the green fluorescent protein. Protoplasts visualised under A. bright field and B. fluorescent light. The green fluorescent protein is observed as a bright spot under fluorescent light.

Figure 39:
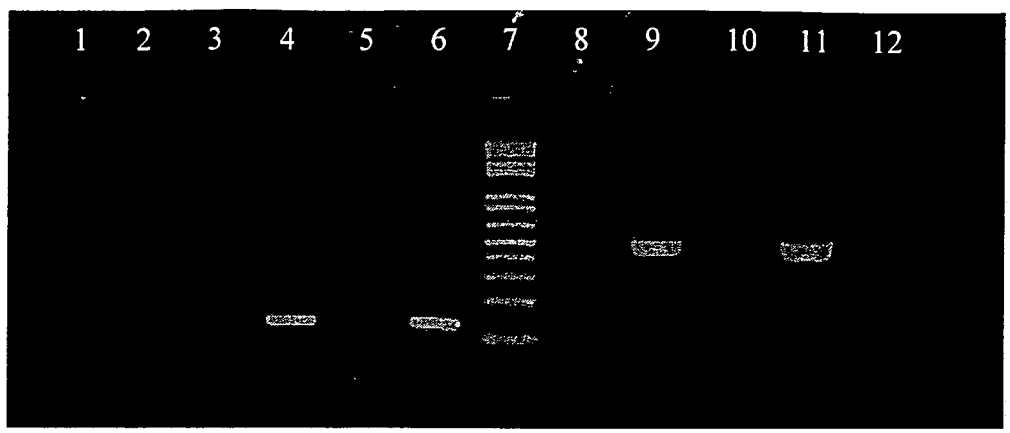

FIG. 39. Electrophoresis of Reverse-transcriptase PCR samples and controls. Lane 1: NO-RT control reaction performed with ANG (F and R) primers on tobacco mesophyll protoplasts transfected with 0957286 CaMV35S-p_turboGFP_nos-t. Lane 2: cDNA from tobacco mesophyll protoplasts transfected with 0957286 CaMV35S-p_turboGFP_nos-t amplified with ANG (F and R) primers. Lane3: NO-RT control reaction performed with ANG (F and R) primers on tobacco mesophyll protoplasts transfected with 1031308 AtRbcS-p_ANG_nos-t. Lane 4: cDNA from tobacco mesophyll protoplasts transfected with 1031308 AtRbcS-p_ANG_nos-t amplified with ANG (F and R) primers. Lane 5: Negative control reaction performed without template (ANG F and R primers). Lane 6: Positive control reaction performed with plasmid template (ANG F and R primers). Lane 7: 1 kb plus DNA Ladder (Invitrogen) Lane 8: NO-RT control reaction performed with Actin (F and R) primers on tobacco mesophyll protoplasts transfected with 0957286 CaMV35S-p_turboGFP_nos-t. Lane 9: cDNA from tobacco mesophyll protoplasts transfected with 0957286 CaMV35S-p_turboGFP_nos-t amplified with Actin (F and R) primers. Lane 10: NO-RT control reaction performed with Actin (F and R) primers on tobacco mesophyll protoplasts transfected with 1031308 AtRbcS-p_ANG_nos-t. Lane 11: cDNA from tobacco mesophyll protoplasts transfected with 1031308 AtRbcS-p_ANG_nos-t amplified with Actin (F and R) primers. Lane 12: Negative control reaction performed without template (Actin F and R primers).

FIG. 40. A. Mesophyll-derived protoplasts recovered from mature leaves of *T. aestium;* 0 days post transfection; B. Assessment of protoplast vigour, with dead cells indicated by dark staining, showing greater than 95 percent viability using Evan's Blue Stain; pre-transfection; C. Assessment of protoplast vigour, with dead cells indicated by dark staining, showing greater than 81 percent viability using Evan's Blue Stain; 24 hours post-transfection.

FIG. 41. Assessment of transient expression 36 hours post transfection with plasmid DNA containing the dsRED gene encoding the dsRED protein. Protoplasts visualised under A. bright field and B. fluorescent light. The dsRED protein is observed as a bright spot under fluorescent light.

Figure 42:
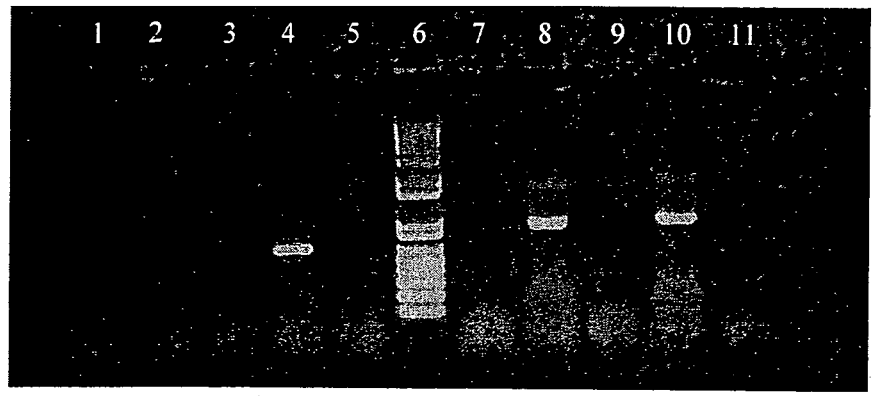

FIG. 42. Electrophoresis of Reverse-transcriptase PCR samples and controls. Lane 1: NO-RT control reaction performed with ANG_F and polyT_R primers on wheat mesophyll protoplasts. Lane 2: cDNA generated by reverse transcription with oligo-dT from total RNA of wheat mesophyll protoplasts amplified with ANG_F and polyT_R primers. Lane3: NO-RT control reaction performed with ANG_F and polyT_R primers on wheat mesophyll protoplasts transfected with 1031312_TaRbcS-p_ANG_nos-t. Lane 4: cDNA from wheat mesophyll protoplasts transfected with 1031312_TaRbcS-p_ANG_nos-t amplified with ANG_F and polyT_R primers. Lane 5: Negative control reaction performed without template (ANG_F and polyT_R primers). Lane 6: 1 kb plus DNA Ladder (Invitrogen). Lane 7: NO-RT control reaction performed with Actin_F and polyT_R primers on wheat mesophyll protoplasts. Lane 8: cDNA from wheat mesophyll protoplasts amplified with Actin_F and polyT_R primers. Lane 9: NO-RT control reaction performed with Actin_F and polyT_R primers on tobacco mesophyll protoplasts transfected with 1031308 AtRbcS-p_ANG_nos-t. Lane 10: cDNA from wheat mesophyll protoplasts transfected with 1031312_TaRbcS-p_ANG_nos-t amplified with Actin_F and polyT_R primers. Lane 11: Negative control reaction performed without template (Actin_F and polyT_R primers).

FIG. 43. *Agrobacterium*-mediated transformation of Canola (*Brassica napus*): A. seed imbibed on filter paper support; B. synchronous germination of seed; C. pre-processing of germinated shoots; D, processing of cotyledons for use as explants; E. regeneration of shoots following cocultivation with *Agrobacterium*; and F. mature plant in glasshouse.

Figure 44:
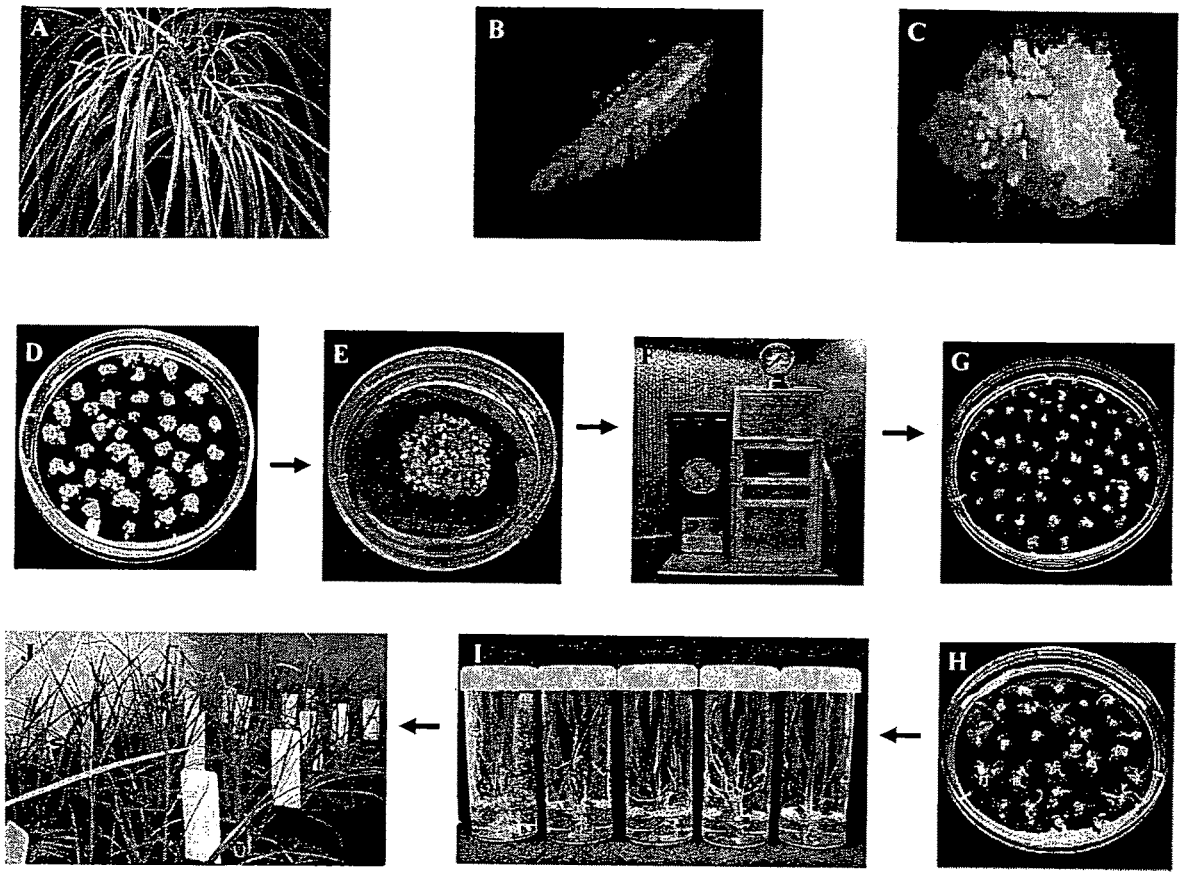

FIG. 44. Preparation of embryogenic callus and biolistic transformation of perennial ryegrass: A. tillers of flowering glasshouse-grown plants prior to surface-sterilisation; B. an immature inflorescence isolated for culture in vitro; C. embryogenic callus after culturing of immature inflorescence tissue in vitro for 4-6 weeks; D-E. isolation of 3-5 mm explants of friable embryogenic callus prior to particle bombardment; F. biolistic bombardment of callus with gold particles coated with a transformation construct; G-H. an antibiotic-resistant shoot on selective medium; I. antibiotic-resistant shoots in vessels of root-inducing medium; J. putative transgenic plantlets in soil.

Figure 45:
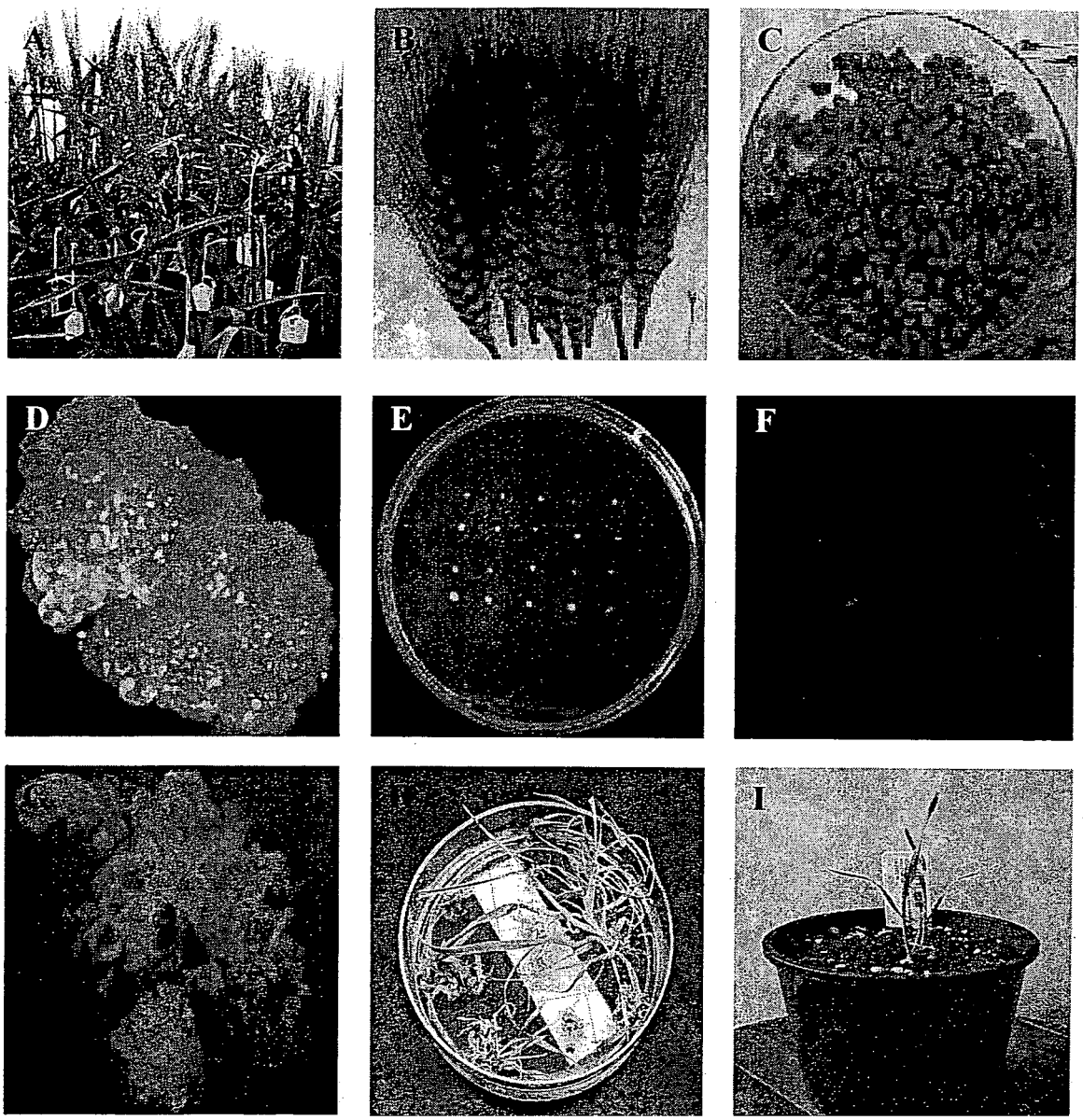

FIG. 45. *Agrobacterium*-mediated transformation of bread wheat: A. donor plants ready for harvest; B&C. harvested material for use as source of embryo explants; D. callus material; E. pre-regeneration material on tissue culture medium; F. callus material illustrating reporter gene expression; G. regenerating shoots from callus; H. rooting shoots on selection media; and I. rooted plant in soil.

Figure 46:
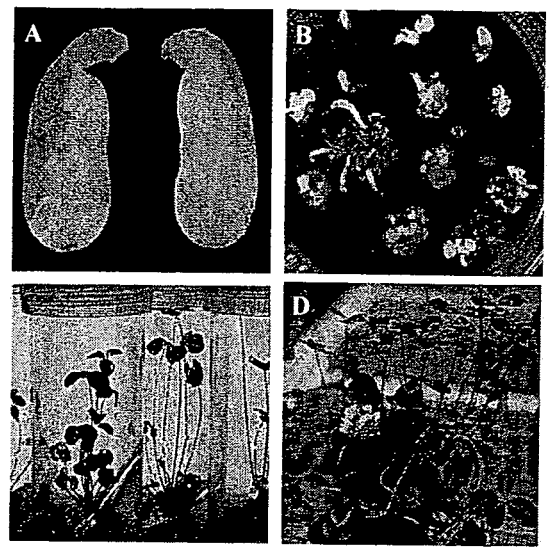

FIG. 46. *Agrobacterium*-mediated transformation of white clover: A. isolation of cotyledonary explants from a mature seed; B. selection of antibiotic-resistant shoots on regeneration medium, C. antibiotic-resistant shoots in vessels of root-inducing medium and D. a putative transgenic plantlet in soil.

Figure 47:
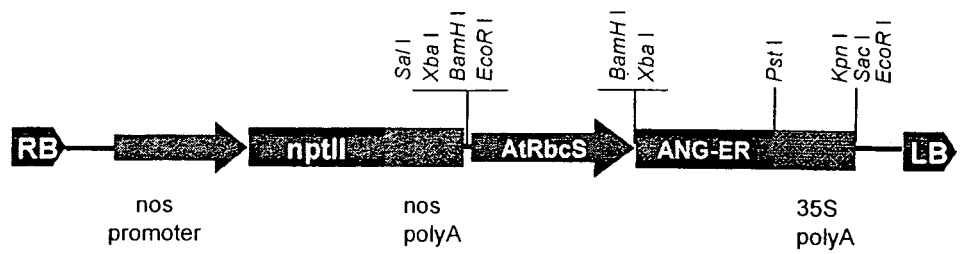

FIG. 47. Map of transformation vector containing nos_nptII_nos selectable marker cassette and the AtRbcS_ANG_CamV35S (FIG. 17) expression cassette used in *Agrobacterium* mediated transformation of white clover.

Figure 48:

FIG. 48. RT-PCR of positive and negative control (lanes 5 and 6) and putative transgenic angiogenin white clover plants (lanes 1 to 4). Primers used were specific to the angiogenin gene.

Figure 49:
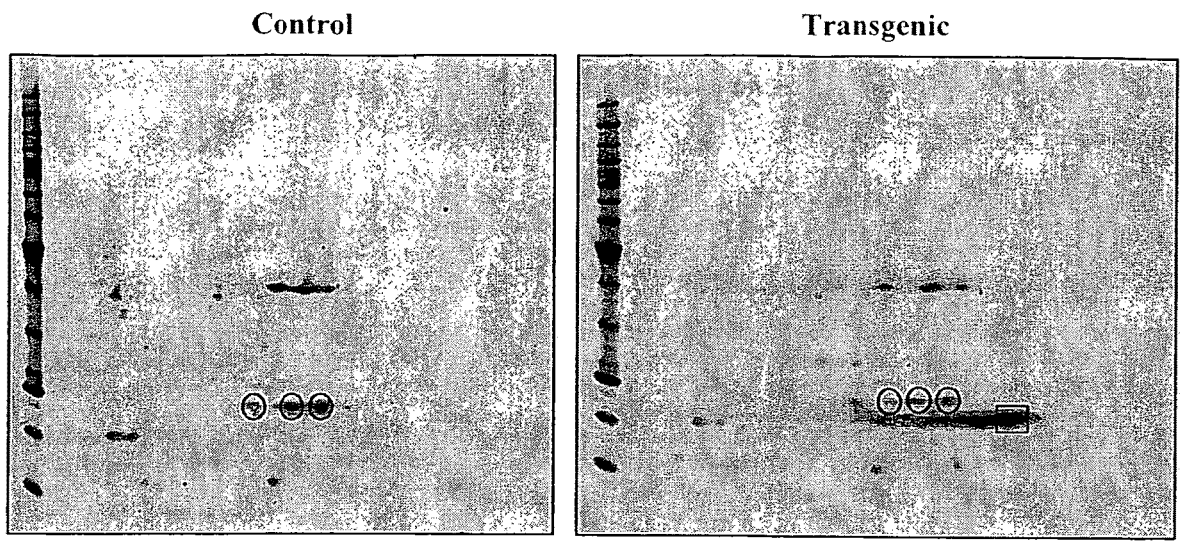

FIG. 49. 2de gel protein analysis of non-transgenic control and transgenic white clover plants. The three circles represent the ribulose bisphosphate carboxylase small subunit. The angiogenin protein is represented by the square.

FIG. 50. 2DE gel protein sequence analysis (SEQ ID NO: 42). Sixty seven percent sequence coverage (indicated in bold and underlined) was obtained of the protein extracted from the gel.

Figure 51:
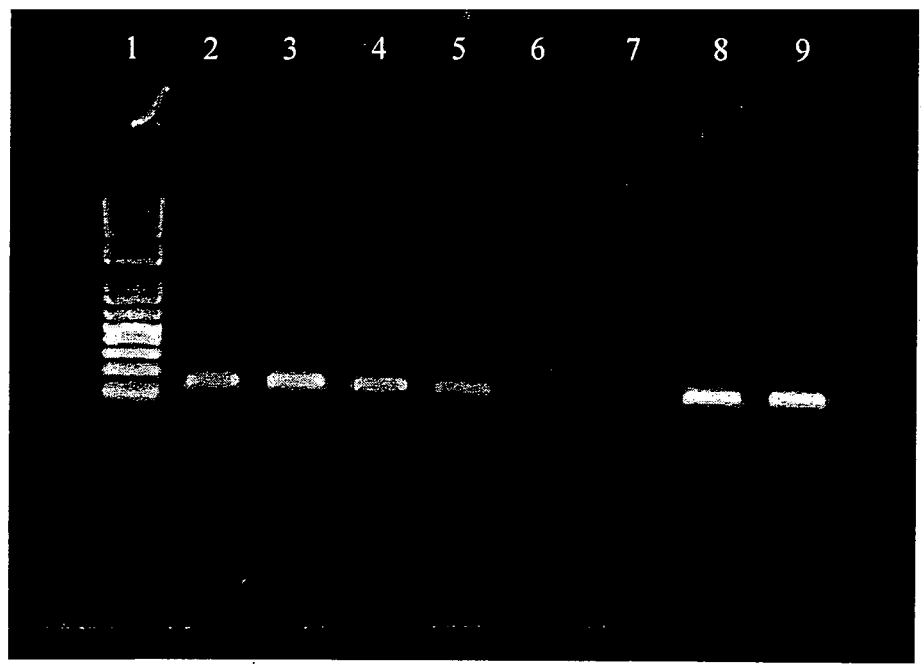

FIG. 51. Electrophoresis of PCR samples and controls. Lane 1: 1 kb plus DNA Ladder (Invitrogen) Lane 2 and 3: PCR of DNA from *Arabidopsis* transgenic line 1, transformed with pPFG000023 AtRbcS-ANG_nos-t, amplified with ANG (F and R) primers. Lane 4 and 5: PCR of DNA from *Arabidopsis* transgenic line 2, transformed with pPFG000023 AtRbcS-ANG_nos-t, amplified with ANG (F and R) primers. Lane 6 and 7: PCR of DNA from wild-type untransformed *Arabidopsis* amplified with ANG (F and R) primers. Lane 8 and 9: Positive control reaction performed with pPFG000023 plasmid template (ANG F and R primers).

DETAILED DESCRIPTION OF THE EMBODIMENTS

In a first aspect, the present invention provides a plant cell, plant callus, plant, seed or other plant part including an angiogenin gene or a functionally active fragment or variant thereof and/or an angiogenin polypeptide. Preferably, said plant cell, plant callus, plant, seed or other plant part is produced by a method as described herein.

In a preferred aspect, the angiogenin gene or functionally active fragment or variant thereof may be co-expressed with a modular or mediator of angiogenin activity.

By 'plant cell' is meant any self-propagating cell bounded by a semi-permeable membrane and containing a plastid. Such a cell also requires a cell wall if further propagation is desired. Plant cell, as used herein includes, without limitation, algae, cyanobacteria, seeds suspension cultures, embryos, meristematic regions, callus tissue, leaves, roots, shoots, gametophytes, sporophytes, pollen and microspores.

In a second aspect, the present invention provides methods of using the plant cells, plant calli, plants, seeds or other plant parts including an angiogenin as a composition such as a feed stock, food supplement or veterinary product for animals or a food, food supplement, nutraceutical or pharmaceutical suitable for human consumption. For example, the value added plant material, including the angiogenin protein, may be used as an enhanced feedstock for a variety of applications.

Accordingly, the present invention provides a method of using a plant cell, plant callus, plant, seed or other plant part including an angiogenin as feed stock for animals or as a composition suitable for human consumption, said method comprising producing the angiogenin in the plant cell, plant callus, plant, seed or other plant part and preparing it in a form suitable for use as a feed stock for animals or a composition suitable for human consumption.

Animals to which the invention may be applied include pigs, chickens (broilers and layers), beef, dairy, goats, sheep are livestock, that can benefit from abundant sources of angiogenin provided by plants, as would companion animals and performance animals eg horses, dogs.

It may be desirable to administer plant derived angiogenin encapsulated or otherwise protected to passage the rumen or stomach more effectively. Less digestible tissues such as seed coat and roots (as opposed to fruit and leaves) may extend gut passage and digestive tract protein release for intestinal binding and uptake.

Co-administration with other supplements and treatments, eg growth hormone such as bovine somatotrophin, antibiotics, nutrient supplements for animals, is also contemplated.

In a third aspect, the present invention provides a plant-produced angiogenin. Preferably said angiogenin is produced by a method as described herein.

In a further aspect, the present invention provides a feedstock, food supplement or veterinary product including a plant-produced angiogenin. Preferably said angiogenin is produced by a method as described herein.

In a further aspect, the present invention provides a food, beverage, food supplement, nutraceutical or pharmaceutical including a plant-produced angiogenin. Preferably said angiogenin is produced by a method as described herein.

In a further aspect, the present invention provides a method of producing a transformed plant cell expressing an angiogenin gene, said method comprising
  providing a gene encoding angiogenin or a functionally active fragment or variant thereof, and a plant cell;
  introducing the angiogenin gene into the plant cell to produce a transformed plant cell; and
  culturing the transformed plant cell to produce a transformed plant cell expressing the angiogenin gene.

By a 'transformed plant cell' is meant a plant cell which has undergone transformation.

By 'transformation' is meant the transfer of nucleic acid into a plant cell.

By a 'gene encoding angiogenin" or 'angiogenin gene' is meant a nucleic acid encoding a polypeptide having one or more of the biological properties of angiogenin. The gene encoding angiogenin may be a transgene. The gene encoding angiogenin may include an angiogenin coding sequence optionally operatively linked to a sequence encoding one or more of a promoter, signal peptide, terminator, and mediator or modulator of angiogenin activity.

By a 'transgene' is meant a nucleic acid suitable for transforming a plant cell.

By a 'functionally active' fragment or variant of an angiogenin gene is meant that the fragment or variant (such as an analogue, derivative or mutant) encodes a polypeptide having one or more of the biological properties of angiogenin. Such variants include naturally occurring allelic variants and non-naturally occurring variants. Additions, deletions, substitutions and derivatizations of one or more of the nucleotides are contemplated so long as the modifications do not result in loss of functional activity of the fragment or variant.

Preferably the functionally active fragment or variant has at least approximately 80% identity to the relevant part of the specified sequence to which the fragment or variant corresponds, more preferably at least approximately 90% identity, even more preferably at least approximately 95% identity, most preferably at least approximately 98% identity.

Preferably the fragment has a size of at least 20 nucleotides, more preferably at least 50 nucleotides, more preferably at least 100 nucleotides, more preferably at least 200 nucleotides, more preferably at least 300 nucleotides.

Such functionally active variants and fragments include, for example, those having conservative nucleic acid changes, those having codon usage adapted for plants, and those in which the signal peptide is removed and optionally replaced by another signal peptide.

By 'conservative nucleic acid changes' is meant nucleic acid substitutions that result in conservation of the amino acid in the encoded protein, due to the degeneracy of the genetic code. Such functionally active variants and fragments also include, for example, those having nucleic acid changes which result in conservative amino acid substitutions of one or more residues in the corresponding amino acid sequence.

By 'conservative amino acid substitutions' is meant the substitution of an amino acid by another one of the same class, the classes being as follows:

Nonpolar: Ala, Val, Leu, Ile, Pro, Met Phe, Trp
Uncharged polar: Gly, Ser, Thr, Cys, Tyr, Asn, Gln
Acidic: Asp, Glu
Basic: Lys, Arg, His Other conservative amino acid substitutions may also be made as follows:

Aromatic: Phe, Tyr, His
Proton Donor: Asn, Gln, Lys, Arg, His, Trp
Proton Acceptor: Glu, Asp, Thr, Ser, Tyr, Asn, Gln Particularly preferred fragments and variants include one or more conserved binding domains such as sequences encoding a catalytic core or a cell binding site. Examples of such domains are shown in FIG. 2 and preferably include the sequence Arg, Asn, Gly, Gln, Pro, Tyr, Arg, Gly, Asp (SEQ ID NO: 43).

Particularly preferred fragments and variants include a catalytic core. By a "catalytic core" is meant an internal region of the polypeptide excluding signal peptide and N- and C-terminal variable regions including catalytic amino acids. Examples of catalytic amino acids are shown in FIG. 2.

Two distinct regions of angiogenin are required for its angiogenic activity including a catalytic site containing His-13, Lys-41, and His-115 that is capable of cleaving RNA and a noncatalytic, cell binding site encompassing minimally residues 60-68. RNase activity and receptor binding capacity, while required, are not sufficient for angiogenic activity: endocytosis and nuclear translocation are required as well.

Catalytic residues in angiogenin include His-13, Lys-40, Gln-12 and Thr-44, for example. These residues may be conserved to retain RNase and/or cellular activity.

Activity may be increased or decreased by changing key amino acids at or near the active site with improved activity substituting Asp-116 to His being an example (Acharva, Shapiro et al). Arg-5 and Arg-33 may also be important for activity.

Cellular uptake of angiogenin in proliferating endothelial cells is mediated by domains and is not dependent upon RNase activity as enzymatically inactive mutants can be internalized. K41Q and H13A mutants for example are enzymatically inactive but are translocated. Improved versions of angiogenin more readily internalised by cells and more potent are within the scope of the present invention, and such variants can be tested for by conducting in vitro uptake and activity tests on epithelial and muscle cells in culture.

Particularly preferred fragments and variants include those lacking a signal peptide. By a "signal peptide" is meant an N-terminal signal sequence. An example of a signal peptide is shown in FIG. 2 and includes the sequence Met, Val, Met, Val, Leu, Ser, Pro, Leu, Phe, Leu, Val, Phe, Ile, Leu, Gly, Leu, Gly, Leu Thr, Pro, Val, Ala, Pro, Ala (SEQ ID NO: 44).

Particularly preferred fragments and variants have codon usage adapted for plants, including the start of translation for monocots and dicots. Thus, the fragment or variant encodes a polypeptide having one or more of the biological properties of angiogenin, but one or more codons, particularly in the third position, may be changed so that the gene is more readily expressed in plants compared with the corresponding animal gene. Changes to one or more of the nucleotides are contemplated so long as the modifications do not result in loss of functional activity of the fragment or variant. Preferably the fragment or variant has at least approximately 60% identity to the relevant part of the original animal sequence to which the modified gene corresponds, more preferably at least approximately 80% identity, even more preferably at least approximately 95% identity, most preferably at least approximately 98% identity. Particularly preferred fragments and variants have cryptic splice sites and/or RNA destabilizing sequence elements inactivated or removed.

It may also be desirable to remove A+T—rich sequences that may cause mRNA instability. This may increase mRNA stability or aberrant splicing and improve efficiency of transcription in plant cell nuclei. This may also eliminate a potential premature poly(A).

Preferably, the angiogenin gene is isolated from or corresponds to an angiogenin gene from an animal, more preferably from a cow, human, gorilla, chimp, monkey, horse, pig, rat, mouse, fish or chicken, even more preferably from *Bos taurus* (cow).

In a particularly preferred embodiment the angiogenin gene encodes a polypeptide comprising the sequence shown in FIG. 2.

In another particularly preferred embodiment, the angiogenin gene comprises a sequence selected from the group consisting of the sequences shown in FIG. 4; and functionally active fragments and variants thereof.

To reduce the possibility of aberrant developmental phenotypes the angiogenin gene may be modified to alter its targeting signal sequence to direct the angiogenin gene to a target sub-cellular component or plant tissue, such as ER, apoplast, peroxisome or vacuole.

More particularly, a chimeric sequence may be created, whereby the signal peptide of the angiogenin gene may be removed and optionally replaced by another signal peptide, for example a plant signal peptide, said plant signal peptide optionally driving angiogenin accumulation to a selected sub-cellular component or plant tissue.

Accordingly, in a still further aspect, the present invention provides a chimeric sequence comprising an angiogenin gene, or a functionally active fragment or variant thereof, and a plant signal peptide.

In a preferred embodiment, the plant signal peptide may be from or correspond to a signal peptide from an ER-derived protein, such as a protein containing a C-terminus 4-amino-acid retention sequence, KDEL (lys-asp-glu-leu) (SEQ ID No.: 51).

The angiogenin gene may be introduced into the plant cell by any suitable technique. Techniques for incorporating the angiogenin gene into plant cells (for example by transduction, transfection, transformation or gene targeting) are well known to those skilled in the art. Such techniques include *Agrobacterium*-mediated introduction, *Rhizobium*-mediated introduction, electroporation to tissues, cells and protoplasts, protoplast fusion, injection into reproductive organs, injection into immature embryos and high velocity projectile introduction to cells, tissues, calli, immature and mature embryos, biolistic transformation, Whiskers transformation, and combinations thereof. The choice of technique will depend largely on the type of plant cell to be transformed, and may be readily determined by an appropriately skilled person.

The present invention may be applied to a variety of plants, including monocotyledons [such as grasses (e.g. forage grasses including perennial ryegrass, tall fescue, Italian ryegrass, *brachiaria, paspalum*), sorghum, sugarcane, corn, oat, wheat, rice and barley)], dicotyledons [such as forage legumes (e.g. white clover, red clover, subterranean clover, alfalfa), soybean, lupin, peas, lentils, chickpeas, canola, vegetable brassicas, lettuce, spinach, fruiting plants (e.g. bananas, citrus, strawberries, apples), oil palm, linseed, cottonseed, safflower, tobacco] and gymnosperms.

In a further aspect the present invention provides a method of producing an angiogenin in a plant, said method comprising providing a gene encoding angiogenin or a functionally active fragment or variant thereof, and a plant cell;
introducing the angiogenin gene into the plant cell to produce a transformed plant cell;
culturing the transformed plant cell to produce a transformed plant cell expressing the angiogenin gene; and
isolating the angiogenin produced by the plant cell.

The angiogenin may be isolated by techniques known to those skilled in the art. For example, cation exchange purification (or enrichment), or size selection may be used.

The term "isolated" means that the angiogenin is removed from its original environment, and preferably separated from some or all of the coexisting materials in the transformation system. Preferably, the angiogenin is at least approximately 90% pure, more preferably at least approximately 95% pure, even more preferably at least approximately 98% pure.

In a further aspect, the present invention provides a method of producing transformed plant calli, plants, seeds or other plant parts including angiogenin, said method comprising providing a gene encoding angiogenin or a functionally active fragment or variant thereof, and a plant cell;
introducing the angiogenin gene into the plant cell to produce a transformed plant cell;
culturing the transformed plant cell to produce transformed plant calli, plants, seeds or other plant parts including angiogenin.

Cells incorporating the angiogenin gene may be selected, as described below, and then cultured in an appropriate medium to regenerate transformed plant calli, plants, seeds or other plant parts, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

In a further aspect, the method further includes isolating angiogenin from the transformed plant calli, plants, seeds or other plant parts.

The angiogenin may be isolated by techniques known to those skilled in the art, for example by extraction. For example, angiogenin may be isolated from ultrafiltrate (Fedorova et al., 2002), including precipitation with ammonium sulfate, followed by cation exchange purification, or using a placental ribonuclease inhibitor binding assay (Bond and Vallee, 1988). More purification may be required for human applications and processed food ingredients and construction.

In a still further aspect, the present invention provides methods of enhancing expression, activity or isolation of angiogenin in plants. The angiogenin gene may be modified to improve its function in animals, particularly mammals. Plant expression may be tailored for enhanced active protein preparation, digestive uptake and biological activity in humans and other animals. For example, the angiogenin gene may be modified to improve a function selected from the group consisting of cellular delivery, myogenic activity, RNase enzyme activity, rRNA transcriptional activity and/or DNA binding activity, rRNA processing and/or splicing activity and receptor binding and/or endocytosis. For example, protease stability, heat stability and/or pH resistance may be improved, which may in turn assist in processing and/or purification of plant-produced angiogenin.

Post-harvest treatment and/or processing may also enhance heat stability, protease stability and/or, cellulase treatment compatibility.

The present invention also contemplates silage compatible expression in plants. Antimicrobial co-expression may be used to stabilize native protein by protecting from or reducing bacterial and/or fungal degradation. Examples include antimicrobial peptides made by bacteria (bacteriocins) or plants (eg thionines, plant defensins) or fungi (AFP and PAF from filamentous fungi) or animals (cathelicidins, defensins, lysozymes). Angiogenin may be complexed with RNase inhibitor to enhance angiogenin expression when co-expressed to reduce toxicity in plants.

The present invention also contemplates co-expressing an angiogenin gene or functionally active fragment or variant thereof with a gene encoding a mediator or modulator of angiogenin activity.

By a 'mediator or modulator of angiogenin activity' is meant a molecule that enhances or otherwise modifies expression, activity or isolation of angiogenin in a plant cell, plant callus, plant, seed or other plant part. For example, the mediator or modulator of angiogenin activity may improve protein accumulation, enhance protein action or activity, or make isolation of the protein more effective. Other examples include enhancement of post-harvest treatment, silage compatibility or processing, improvement of protease stability or heat stability and improvement of treatment compatibility.

For example, the angiogenin gene may be co-expressed with a gene encoding one or more of antimicrobials, protease inhibitors, RNase inhibitors, follistatin, and delayed plant organ senescence gene or genes.

The present invention also contemplates artificial constructs or chimeric sequences comprising an angiogenin gene or functionally active fragment or variant thereof and a gene encoding a mediator or modulator of angiogenin activity.

By a 'chimeric sequence' is meant a hybrid produced recombinantly by expressing a fusion gene including two or more linked nucleic acids which originally encoded separate proteins, or functionally active fragments or variants thereof.

By a 'fusion gene' is meant that two or more nucleic acids are linked in such a way as to permit expression of the fusion protein, preferably as a translational fusion. This typically involves removing the stop codon from a nucleic acid sequence coding for a first protein, then appending the nucleic acid sequence of a second protein in frame. The fusion gene is then expressed by a cell as a single protein.

The protein may be engineered to include the full sequence of both original proteins, or a functionally active fragment or variant of either or both.

The present invention also provides an angiogenin gene with codon usage adapted for plants, said angiogenin gene being capable of being expressed in a plant cell which has been transformed with said gene.

Preferably, the angiogenin gene is isolated from or corresponds to an angiogenin gene from an animal, more preferably *Bos taurus* (cow).

In a particularly preferred embodiment the angiogenin gene encodes a polypeptide comprising the sequence shown in FIG. 2.

In another particularly preferred embodiment, the angiogenin gene comprises a sequence selected from the group consisting of the sequences shown in FIG. 4; and functionally active fragments and variants thereof.

By an 'angiogenin gene with codon usage adapted for plants' is meant that the angiogenin gene encodes a polypeptide having one or more of the biological properties of angiogenin, but that one or more codons, particularly in the third position, have been changed so that the gene is more readily expressed in plants compared with the corresponding animal gene. Changes to one or more of the nucleotides are contemplated so long as the modifications do not result in loss of functional activity of the fragment or variant. Preferably the angiogenin gene with codon usage adapted for plants has at least approximately 60% identity to the relevant part of the original animal sequence to which the modified gene corresponds, more preferably at least approximately 80% identity, even more preferably at least approximately 95% identity, most preferably at least approximately 98% identity.

In a further aspect of the present invention, there is provided an artificial construct capable of enabling expression of an angiogenin gene in a plant cell, said artificial construct including a promoter, operatively linked to an angiogenin gene, or a functionally active fragment or variant thereof.

By 'artificial construct' is meant a recombinant nucleic acid molecule.

By a 'promoter' is meant a nucleic acid sequence sufficient to direct transcription of an operatively linked nucleic acid sequence.

By 'operatively linked' is meant that the nucleic acid(s) and a regulatory sequence, such as a promoter, are linked in such a way as to permit expression of said nucleic acid under appropriate conditions, for example when appropriate molecules such as transcriptional activator proteins are bound to the regulatory sequence. Preferably an operatively linked promoter is upstream of the associated nucleic acid.

By 'upstream' is meant in the 3'→5' direction along the nucleic acid.

By 'gene' is meant a chain of nucleotides capable of carrying genetic information. The term generally refers to genes or functionally active fragments or variants thereof and or other sequences in the genome of the organism that influence its phenotype. The term 'gene' includes DNA (such as cDNA or genomic DNA) and RNA (such as mRNA or microRNA) that is single- or double-stranded, optionally containing synthetic, non-natural or altered nucleotide bases, synthetic nucleic acids and combinations thereof.

In a preferred embodiment, the artificial construct according to the present invention may be a vector.

By a 'vector' is meant a genetic construct used to transfer genetic material to a target cell.

The vector may be of any suitable type and may be viral or non-viral. The vector may be an expression vector. Such vectors include chromosomal, non-chromosomal and synthetic nucleic acid sequences, eg. derivatives of plant viruses; bacterial plasmids; derivatives of the Ti plasmid from *Agrobacterium tumefaciens*; derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable or integrative or viable in the plant cell.

In a preferred embodiment of this aspect of the invention, the artificial construct may further include a terminator; said promoter, gene and terminator being operably linked.

The promoter, gene and terminator may be of any suitable type and may be endogenous to the target plant cell or may be exogenous, provided that they are functional in the target plant cell.

The promoter used in the constructs and methods of the present invention may be a constitutive, tissue specific or inducible promoter. For example, the promoter may be a constitutive cauliflower mosaic virus (CaMV35S) promoter for expression in many plant tissues, an inducible 'photosynthetic promoter' (eg. ribulose 1,5-bisphosphate), capable of mediating expression of a gene in photosynthetic tissue in plants under light conditions, or a tissue specific promoter such as a seed specific promoter, for example from a gene selected from the group consisting of *Brassica napus* napin gene, *Zea mays* zein 4 gene, *Orysa sativa* PR602 gene and *Triticum aestivum* glutelin gene.

A variety of terminators which may be employed in the artificial constructs of the present invention are also well known to those skilled in the art. The terminator may be from the same gene as the promoter sequence or a different gene. Particularly suitable terminators are polyadenylation signals, such as the CaMV35S polyA and other terminators from the nopaline synthase (nos) and the octopine synthase (ocs) genes.

The artificial construct, in addition to the promoter, the gene and the terminator, may include further elements necessary for expression of the gene, in different combinations, for example vector backbone, origin of replication (ori), multiple cloning sites, spacer sequences, enhancers, introns (such as the maize Ubiquitin Ubi intron), antibiotic resistance genes and other selectable marker genes [such as the neomycin phosphotransferase (nptII) gene, the hygromycin phosphotransferase (hph) gene, the phosphinothricin acetyltransferase (bar or pat) gene], and reporter genes (such as beta-glucuronidase (GUS) gene (gusA)]. The artificial construct may also contain a ribosome binding site for translation initiation. The artificial construct may also include appropriate sequences for amplifying expression.

Those skilled in the art will appreciate that the various components of the artificial construct are operably linked, so as to result in expression of the angiogenin gene. Techniques for operably linking the components of the artificial construct of the present invention are well known to those skilled in the art. Such techniques include the use of linkers, such as synthetic linkers, for example including one or more restriction enzyme sites.

Preferably, the artificial construct is substantially purified or isolated. By 'substantially purified' is meant that the artificial construct is free of the genes, which, in the naturally-occurring genome of the organism from which the nucleic acid or promoter of the invention is derived, flank the nucleic acid or promoter. The term therefore includes, for example, an artificial construct which is incorporated into a vector; into an autonomously replicating plasmid or virus; or into the genomic DNA of a prokaryote or eukaryote; or which exists as a separate molecule (eg. a cDNA or a genomic or cDNA fragment produced by PCR or restriction endonuclease digestion) independent of other sequences. It also includes an artificial construct which is part of a hybrid gene encoding additional polypeptide sequence. Preferably, the substantially purified artificial construct is at least approximately 90% pure, more preferably at least approximately 95% pure, even more preferably at least approximately 98% pure.

The term "isolated" means that the material is removed from its original environment (eg. the natural environment if it is naturally occurring). For example, a naturally occurring nucleic acid present in a living plant is not isolated, but the same nucleic acid separated from some or all of the coexisting materials in the natural system, is isolated. Such nucleic acids could be part of a vector and/or such nucleic acids could be part of a composition, and still be isolated in that such a vector or composition is not part of its natural environment.

As an alternative to use of a selectable marker gene to provide a phenotypic trait for selection of transformed host cells, the presence of the artificial construct in transformed cells may be determined by other techniques well known in the art, such as PCR (polymerase chain reaction), Southern blot hybridisation analysis, histochemical assays (e.g. GUS assays), thin layer chromatography (TLC), northern and western blot hybridisation analyses.

Applicant has surprisingly found that the methods of the present invention may result in enhanced yield of angiogenin in the transformed plant cell relative to yields of proteins typically produced in transgenic plant cells.

In a preferred embodiment the methods of the present invention provide a yield of between approximately 0.1% and 5%, more preferably between approximately 5% and 10%, more preferably between approximately 10% and 30%, of total soluble protein.

EXAMPLES

Example 1

Cloning of the Bovine Angiogenin Gene

The *Bos taurus* (cow) angiogenin, ribonuclease, RNase A family, 5 (ANG), mRNA sequence is available from the National Centre for Biotechnology Information (NCBI), accession number AM_0011078144. The predicted open reading frame (ORF) contains 444 base pairs (bp) (FIG. 1) encoding a 148 amino acid (aa) (FIG. 2) sequence. Using the SignalP 3.0 server to predict the presence and location of signal peptide cleavage sites in amino acid sequences a 24 aa (72 bp) signal peptide sequence was identified (FIGS. 1 and 2).

The angiogenin protein sequence has been analysed by comparison to a database of known allergens, the Food Allergy and Resource Research Program at the University of Nebraska allergen protein database (FARRP Allergen Online version 7.0). A BLASTp for every 80 amino acid peptides contained within the protein was searched against the FAARP Allergen Online database. None of the amino acid peptides contained 35% or higher identity to any of the known allergens of the database, a standard often used as a threshold for allergenicity concern. A BLASTp for the angiogenin protein in its entirety was also searched against the FARRP Allergen Online dataset. The angiogenin protein did not contain eight or more consecutive amino acids in common with any member of the database, a standard frequently used as a threshold for allergenicity concern.

Using the angiogenin NCBI sequence, primers were designed to amplify a modified ANG gene adapted for plant codon usage as defined by Murray et al. (1989) (FIG. 3). No changes in amino acid sequence to that outlined in FIG. 2 were observed.

The Angiogenin Gene from Divergent Organisms

Using the bovine angiogenin gene as a query sequence a range of different sequences have been identified and are available from NCBI. Nucleotide and amino acid sequence alignments of angiogenin from divergent organisms have been produced (FIGS. 4 and 5).

Codon Optimisation of Angiogenin Genes for Expression in Plants

Different ANG nucleotide sequences to those outlined in FIGS. 1 and 3, optimised by alternate methods for codon bias of both monocot and dicot plants have been produced to enhance protein expression in plants (FIGS. 6 and 7). Negative cis-acting sites which may negatively influence expression were eliminated wherever possible and GC content was adjusted to prolong mRNA half life. An alignment to indicate the difference in sequence homology between the monocot and dicot optimised sequences is presented in FIG. 8. The degree of sequence homology between the two sequences is 80.7%. The codon optimisation undertaken did not alter the amino acid sequence translation that is outlined in FIG. 2 (without the signal peptide sequence).

Example 2

Production of Fusion Proteins for Greater Accumulation, Enhanced Action, or Improved Extraction, of Angiogenin It is possible to create fusion proteins of angiogenin with mediators or modulators of its activity to assist in the improvement of protein accumulation, enhancement of protein action, or for effective extraction of the protein.

Fusion Proteins for Enhancing the Action of Angiogenin

Yeast two-hybrid technology has identified potential ANG-interacting molecules (Goa and Xu, 2008) such as alpha-actin 2 (ACTN-2) (Hu et al., 2005), regulatory proteins such as follistatin (FS) (Goa et al., 2007) and extracellular matrix proteins such as fibulin-1 (Zhang et al., 2008). It is hypothesised that through interacting with ACTN-2, ANG may regulate the movement or the cytokinesis of the cells, follistatin may act as a regulator on angiogenin's actions and interaction between ANG and fibulins may facilitate cell adhesion.

Follistatin is known to have a role in muscle growth and regulates muscle cell development through binding and blocking myostatin, a TGF family member and potent negative regulator of myoblast growth and differentiation. In partnership with RNase5, follistatin can act directly and synergistically as a positive regulator of muscle growth and differentiation. It has been demonstrated that RNase5 activation of muscle cell growth and differentiation in vitro is enhanced by follistatin (patent PCT/AU2009/000603). Creation of a translational fusion of these two genes, codon optimised for expression in plants, can be used to enhance the ability of angiogenin to control muscle development.

The activity of angiogenin may be blocked by ribonuclease inhibitors. Co-expression of angiogenin with ribonuclease inhibitor both codon optimised for expression in plants, may be used to regulate the intracellular activity of angiogenin and improve expression by reducing toxicity in plants.

Fusion Proteins for the Improved Extraction of Angiogenin

Oleosins provide an easy way of purifying proteins which have been produced recombinantly in plants. Oleosins are structural proteins found in a unique seed-oil storage organelle know as the oilbody. It is suggested that a central hydrophobic domain within the oleosin gene is most likely to play a role in localisation to the oil body. Therefore, through covalent fusions with oleosin a recombinant protein can be directed to the oil bodies allowing easy extraction. Abenes et al. (1997) showed that an *Arabidopsis* oleosin-GUS fusion protein could be expressed and targeted to oil bodies in at least five species of oilseeds. Consequently, the angiogenin protein may be directed to the oil body by the creation of an oleosin_angiogenin fusion sequence (FIGS. 9 and 10). Incorporating a protease recognition site between the two sequences allows the oleosin to be cleaved from the protein of interest.

Example 3

Identification of Promoter Sequences for Targeted Expression of Angiogenin

Promoters with tissue-specificity are required to drive expression of transgenes in crops to target accumulation in particular tissues/organs and to avoid unwanted expression elsewhere. Therefore highly expressing but yet tightly controlled promoters are desirable.

Tissue Specific or Regulated Promoters

The choice of promoters affects transgene expression concentration, as well as developmental, tissue and cell specificity. Examples of different promoters to drive transgene expression for different objectives are presented in Table 1.

TABLE 1

Examples of different promoters to drive transgene expression.

| Targeted expression | Gene promoter | Organism | Reference |
|---|---|---|---|
| Constitutive | | | |
| Constitutive | Ubiquitin, Ubi | *Zea mays* (maize) | Christensen et al. (1992) |
| | CaMV35S[2] | Cauliflower mosaic virus | Kay et al. (1987) |
| | Polyubiquitin, RUBQ2 | *Oryza sativa* (rice) | Liu et al. (2003) |
| | Actin 1, OsAct1 | *Oryza sativa* (rice) | McElroy et al. (1990) |
| Tissue Specific | | | |
| Tuber and stolon specific | Sucrose synthetase, Sus4 | *Solanum tuberosum* (potato) | Lin et al. (2008) |
| | Cathepsin D inhibitor gene, Cathinh | *Solanum tuberosum* (potato) | Herbers et al. (1994) |
| Root and shoot of sugar beet | Helicase-like genes, helA, helB and helC | *Pseudomonas* plasmid | Zhang et al. (2004) |
| Root specific | Phosphate Transporter AtPHT1 | *Arabidopsis thaliana* | Koyama et al., (2005) |
| | Phosphate Transporter HvPHT1 | *Hordeum vulgare* (barley) | Schunnman et al., (2004) |
| Seed specific | β-conglycinin, a soybean seed storage protein | *Glycine max* (soybean) | Chen et al. (1988) |
| | 11S seed storage protein gene | *Coffea Arabica* (coffee bean) | Marraccini et al. (1999) |
| | Napin gene | *Brassica napus* (canola) | Lee et al. (1991) |
| | Glutelin A | *Oryza staiva* (rice) | Hashizume et al. (2008) |
| | Glutelin | *Triticum aestivum* (wheat) | Lamacchia et al. (2001) |
| | Zein gene, ZmZ4 | *Zea mays* (maize) | Penderson et al. (1982) Schernthaner et al. (1988) |
| | Endoperm Specific, OsPR602 | *Oryza staiva* (rice) | Li et al., (2008) |
| Seed - Aluerone | Maize regulatory gene B-Peru | *Zea mays* (maize) | Selinger et al. (1998) |
| Fruit specific | Fruit specific E8 | Tomato | Ramierez et al. (2007) |
| Phloem | Sucrose synthase, Suc2 | *Zea mays* (maize) | Yang and Russell (1990) |
| Xylem | phenylalanine ammonialyase gene 2, PAL2 | *Nicotiana benthamiana* (tobacco) | Keller and Baumgartner (1991) |
| | 4-coumarate:coenzyme A ligase. 4CL | *Nicotiana benthamiana* (tobacco) | Hauffe et al. (1993) |

TABLE 1-continued

Examples of different promoters to drive transgene expression.

| Targeted expression | Gene promoter | Organism | Reference |
|---|---|---|---|
| Xylem - lignified cells | cinnamoyl coenzymeA reductase (OCR) and cinnamyl alcohol dehydrogenase (CAD2) | *Eucalyptus gunnii* (*Eucalyptus*) | Baghdady et al. (2006) |
| Inducible | | | |
| Cold, dehydration and salt stress responsive | Calcium dependent protein kinases, OsCPK6, OsCPK13, OsCPK25 | *Oryza sativa* (rice) | Wan et al. (2007) |
| Dehydration stress | early responsive to dehydration stress, ERD1 | *Arabidopsis thaliana* | Tran et al. (2004) |
| Stress responsive | Rd29A | *Arabidopsis thaliana* | Yamaguchi-Shinozaki and Shinozaki (1993) |
| Sucrose responsive | ADP-glucose pyrophosphorylase, IbAGP1 | *Ipomoea batatas* (sweet potato) | Kwak et al. (2005) |
| | ADP-glucose pyrophosphorylase, LeAgpS1 | *Lycopersicon esculentum* (tomato) | Li et al. (2001) |
| | 14-3-3 protein family, 16R | *Solanum tuberosum* (potato) | Szopa et al. (2003) |
| Ethylene responsive | ethelyene responsive binding elements, GhERF4 | *Gossypium hirsutum* (cotton) | Jin and Lui (2008) |
| Cold responsive | wcs120 | *Triticum aestivum* (wheat) | Ouellet et al. (1998) |
| Dessication responsive in leaves, flowers and green fruit | StDS2 | *Solanum tuberosum* (potato) | Doczi et al. (2005) |
| | LeDS2 | *Lycopersicon esculentum* | Doczi et al. (2005) |
| Oxidative stress induced by high light and ozone | Peptide methionine sulfoxide reductase A, PMRSA | *Arabidopsis thaliana* | Romero et al. (2006) |
| Wound | Wun1, proteinase inhibitor II genes of potato | *Solanum tuberosum* (potato) | Siebertz et al. (1989) |
| Starch | ADP Glucose Pyrophosphorylase, ADPGIc | *Arabidopsis thaliana* | Stark et al. 1992 |
| Light regulated | Ribulose-1,5-bisphosphate carboxylase/oxygenase Small subunit, TaRbcS, AtRbcS, and LpRbcS respectively | *Triticum aestivum* (wheat), *Arabidopsis thaliana*, and *Lolium perenne* respectively | Zeng, et al., (1995), Sasanuma, (2001) |
| | Chlorophyll a/b Binding Protein, LpCAB | *Lolium perenne* (ryegrass) | |

Representative examples of promoters for light regulated, seed and root specific linked to the angiogenin gene are presented in FIGS. 11-34.

Example 4

Identification of Signal Peptide Sequences for Targeted Expression of Angiogenin Signal peptides are short (3-60 amino acids long) peptide chains that direct the transport of a protein to different subcellular compartments such as the nucleus, mitochondrial matrix, endoplasmic reticulum (ER), chloroplast, apoplast, vacuole and peroxisome.

Most proteins that are transported to the ER have a sequence consisting of 5-10 hydrophobic amino acids on the N-terminus. The majority of these proteins are then transported from the ER to the Golgi apparatus unless these proteins have a C-terminus 4-amino-acid retention sequence, KDEL (lys-asp-glu-leu) (SEQ ID No.: 51), which holds them in the ER.

The nucleus and nucleolus can be targeted with either a nuclear localization signal (NLS) or a nucleolar localization signal (abbreviated NoLS or NOS), respectively. The signal peptide that directs to the mitochondrial matrix is usually called the mitochondrial targeting signal (MTS). There are two types (N- and C-terminus) peroxisomal targeting signals (PTS). PTS1, consists of three amino acids at the C-terminus while PTS2, is made of a 9-amino-acid sequence present on the N-terminus of the protein.

Constructs Containing Tissue Specific or Regulated Promoters

Signal peptides are desirable to target accumulation of recombinant proteins for extraction from plant secretions or plant tissue. Examples of different signal peptides to drive target protein accumulation in different sub-cellular compartments are presented in Table 2.

TABLE 2

Examples of different signal peptide sequences
for targeted transgene expression.

| Signal target | Gene signal peptide | Organism | Reference |
| --- | --- | --- | --- |
| ER | H/KDEL (C-terminal) (SEQ ID NO: 51) | Plant species | Hara-Nishimura et al., (2004) |
| apoplast | Proteinase inhibitor II | Tobacco | Denecke et al., (1990) |
| | Calreticulin | | Borisjuk et al., (1998) |
| peroxisome | SKL, SQL, -SML, -SSL, -SAL (all C-terminal) | Tobacco | Kragler et al., (1998) |
| vacuole | NTPP (N-terminal) (SEQ ID NO: 53) CTPP (C-terminal) | Plant species | Marty, (1999) |

Example 5

Generation of Vectors for Transfection of Dicot and Monocot Protoplasts

Generation of Vectors for Transfection of Dicot Protoplasts

An expression vector was generated for transient expression of Angiogenin in dicot protoplast cells. The nucleotide sequence of the expression cassette contains the ANG gene with an ER signal retention peptide regulated by the AtRbcS light regulated promoter and nopaline synthase (nos) terminator from *Agrobacterium tumefaciens* for accumulation in dicot plant tissue (1031312_AtRbcS-p_ANG_nos-t; FIGS. 11 and 12).

A control vector (0957286 CaMV35s-p_turboGFP_nos-t; FIG. 13) encoding a cassette for expressing a fluorescent marker (turboGFP) in dicot plant cells was also used to confirm protein expression. The cassette consists of the CaMV35S promoter, coding sequence for the turboGFP protein which was codon-optimised for expression in dicots and the nopaline synthase (nos) terminator.

Generation of Vectors for Transfection in Monocot Protoplasts

An expression vector was generated for transient expression of Angiogenin in monocot protoplast cells. The nucleotide sequence of the expression cassette contains the ANG gene with an ER signal retention peptide regulated by the TaRbcS light regulated promoter and nopaline synthase (nos) terminator from *Agrobacterium tumefaciens* for accumulation in monocot plant tissue (1031308_TaRbcS-p_ANG_nos-t; FIGS. 14 and 15).

A control vector (0957284 ZmUbi-p_dsRED_nos-t; FIG. 16) encoding a cassette for expressing a fluorescent marker (dsRED) in monocot plant cells was also used to confirm protein expression. The cassette consists of the Ubiquitin promoter from *Zea mays*, coding sequence for the dsRED protein which is codon-optimised for expression in wheat, and the nopaline synthase (nos) terminator.

Example 6

Generation of Vectors for Stable Transformation and Production of Transgenic Plants Expression of the recombinant protein in edible tissue for feed stock or human consumption offers a convenient and inexpensive source of delivery. However, an added value may also be obtained by the extraction of a recombinant protein as a by-product from the primary source. Accordingly, the combination of elements chosen to regulate the expression, and direct the angiogenin protein, is central to both these methods.

Production of Expression Vectors for Biolistic and *Agrobacterium*-Mediated Transformation Base transformation vectors are required to contain all the necessary elements for bilolistic and *Agrobacterium* mediated transformation of plants. To this end, various selectable marker cassettes, containing a selectable marker gene controlled by promoter and terminator regulatory sequences, are required for selection within different transformation process, and for distinct plant types.

Expression vectors are generated for biolistic and *Agrobacterium* mediated transformation by the introduction of expression cassettes, containing the ANG gene with a modified signal sequence driven by targeted expression promoters, into different base vectors. Expression cassette promoters and signal sequences will be optimised to a particular strategy such that the strength and targeted delivery of the protein will be suited to the final processing of the transgenic plant.

Expression Cassette Containing an ER Signal Peptide and Light Regulated Promoter for Accumulation in Dicot Plant Tissue To achieve high levels of protein accumulation in photosynthetic dicot plant tissue a light-regulated promoter (AtRbcS) was combined with the FIG. 3 modified ANG gene containing the KDEL ER retention signal (SEQ ID No.: 51), and the cauliflower mosaic virus CamV35S terminator sequence (FIG. 17).

An expression vector was generated for stable expression of Angiogenin in dicot cells. The nucleotide sequence of the expression cassette contains the ANG gene with an ER signal retention peptide regulated by the AtRbcS light regulated promoter and nopaline synthase (nos) terminator from *Agrobacterium tumefaciens* for accumulation in dicot plant tissue (pPFG000023 AtRbcS-p_ANG_nos-t; FIGS. 11 and 18).

Expression Cassette Containing an ER Signal Peptide and Light Regulated Promoter for Accumulation in Monocot Plant Tissue To achieve high levels of protein accumulation in photosynthetic monocot plant tissue light-regulated promoters (TaRbcS and LpRbcS) were combined with the FIG. 6 modified ANG gene containing the KDEL ER retention signal (SEQ ID No.: 51), and the cauliflower mosaic virus CamV35S terminator sequence (FIGS. 20 and 21 respectively).

Expression Cassette Containing a ER Signal Peptide and *Brassica napus* Napin Gene Promoter for Accumulation in Dicot Plant Seed Recombinant seed offers the possibility of direct use as edible plant tissue or is a promising target for extraction. To achieve high levels of protein accumulation in dicot plant seed, a seed specific promoter (*Brassica napus* napin gene) was combined with, the FIG. 7 modified ANG gene containing a KDEL ER retention signal (SEQ ID No.: 51), and the cauliflower mosaic virus CaMV35S or nos terminator sequences (FIGS. 22, 23 and 24).

Expression Cassette Containing a ER Signal Peptide and *Zea mays* Zein Gene Promoter for Accumulation in Monocot Plant Seed Recombinant seed offers the possibility of direct use as edible plant tissue or is a promising target for extraction. To achieve high levels of protein accumulation in plant monocot seed, a seed specific promoter (*Zea mays* zein gene) was combined with, the FIG. 6 modified ANG gene containing a KDEL ER retention signal (SEQ ID No.: 51), and the cauliflower mosaic virus CaMV35S or nos terminator sequences (FIGS. 25, 26 and 27).

Expression Cassette Containing an Apoplast Signal Peptide and Constitutive Promoter for Secretion in Guttation Fluid Targeted secretion has the potential of increasing the efficiency of recombinant protein production technology by increasing yield, abolishing extraction and simplifying its downstream process. For example, by using endoplasmic reticulum signal peptides fused to recombinant protein sequences plants may secrete the protein through the leaf intracellular space into guttation fluid. Guttation is liquid formation at the edges of plant leaves produced at night due to excess water potential. Guttation fluid can be collected throughout a plant's life, thus providing a continuous and non-destructive system for recombinant protein production.

To achieve high levels of protein secretion through guttation in both monocots and dicots, the cauliflower mosaic virus (CaMV35S) constitutive promoter and terminator sequences were combined with, the FIG. 7 modified ANG gene containing a tobacco calreticulin apoplast signal peptide (FIG. 32).

Expression Cassette Containing an Apoplast Signal Peptide and Root-Specific Promoter for Rhizosecretion in Dicots Targeted and directed expression can be also used to generate rhizosecretion, a method for the production and secretion of recombinant proteins from roots (Gleba, et al., 1998). Expression of ANG using an *Arabidopsis* root specific promoter (AtPHT1) and targeted by a tobacco calreticulin apoplast signal peptide the recombinant protein could be extracted from rhizosecretion of hydroponically grown transgenic monocot plants (FIG. 33).

Expression Cassette Containing an Apoplast Signal Peptide and Root-Specific Promoter for Rhizosecretion in Dicots Targeted and directed expression can be also used to generate rhizosecretion, a method for the production and secretion of recombinant proteins from roots (Gleba, et al., 1998). Expression of ANG using a *Hordeum vulgare* root specific promoter (HvPHT1) and targeted by a tobacco calreticulin apoplast signal peptide the recombinant protein could be extracted from rhizosecretion of hydroponically grown transgenic plants (FIG. 34).

Expression Cassette Containing an Oleosin Promoter and ANG_Oleosin Fusion Gene for Extraction from Oil Bodies To achieve high levels of protein in oil bodies, the *Arabidopsis* oleosin promoter and CaMV35S terminator were combined with, the oleosin_ANG fusion gene (FIG. 9) to produce an expression cassette (FIG. 35).

Expression Cassette for Transformation of the Plant Chloroplast Genome

Many biopharmaceutical transgenes have been stably integrated and expressed using the tobacco chloroplast genome to confer desired agronomic traits or express high levels of protein (Daniell et al., 2005). The FIG. 7 modified ANG gene has been paired with the tobacco 16sRNA operon (Prrn) promoter and terminator sequences (Zoubenko, et al., 1994) to express the angiogenin gene in chloroplasts (FIG. 36).

Example 7

Production of Transgenic Plants Expressing Chimeric Angiogenin Genes

The genetic constructs may be introduced into the plant by any suitable technique. Techniques for incorporating the genetic constructs of the present invention into plant cells (for example by transduction, transfection or transformation). Such techniques include *Agrobacterium*-mediated introduction, electroporation of tissues, cells and protoplasts, protoplast fusion, injection into reproductive organs, injection into immature embryos and high velocity projectile introduction to cells, tissues, calli, immature and mature embryos, biolistic transformation and combinations thereof. The choice of technique will depend largely on the type of plant to be transformed and the appropriate vector for the method chosen will be used.

Cells incorporating the genetic constructs of the present invention may be selected, as directed by the vectors used, and then cultured in an appropriate medium to regenerate transformed plants, using techniques well established. The resulting plants may be reproduced, either sexually or asexually, to produce successive generations of transformed plants.

The present invention may be applied to a variety of plants, including monocotyledons [such as grasses (e.g. forage grasses including perennial ryegrass, tall fescue, Italian ryegrass, *brachiaria, paspalum*), sorghum, sugarcane, corn, oat, wheat, rice and barley)], dicotyledons [such as forage legumes (e.g. white clover, red clover, subterranean clover, alfalfa), soybean, lupin, peas, lentils, chickpeas, canola, vegetable brassicas, lettuce, spinach, fruiting plants (e.g. bananas, citrus, strawberries, apples), oil palm, linseed, cottonseed, safflower, tobacco] and gymnosperms.

Example 8

Transfection of Dicot and Monocot Protoplasts

Dicot Protoplast Transfection of Angiogenin

Protoplasts were released from mesophyll tissue of the dicot, *Nicotiana tabacum* using the method described in Spangenberg and Potrykus, 1996. The viability of tobacco protoplasts was assessed using Evans Blue stain as described in Huang et al., 1986 (FIG. 37).

DNA from two plasmids encoding either an expression cassette designed to express the ANG protein under control of the AtRbcS promoter (1031312_TaRbcS-p_ANG_nos-t; FIGS. 11 and 12), or a control expression cassette designed to express the fluorescent reporter (turboGFP) under control of the constitutive CaMV35S promoter (0957286 CaMV35s-p_turboGFP_nos-t; FIG. 13), were purified.

Both plasmid vectors were linearised by restriction endonuclease digestion and delivered to aliquots of protoplasts cells. After 24 hours, successful delivery and gene expression were confirmed by visualisation of the fluorescent marker in the control samples (Figure Transient Gene Expression and Detection of Angiogenin in Dicot Protoplasts To detect expression of Angiogenin, DNA-free RNA was purified from protoplast samples. Complimentary DNA (cDNA) was synthesised and reverse transcriptase-PCR (RT-PCR) analysis of each sample was conducted using primers, as outlined in Table 3, to Angiogenin (ANG F and R) and the endogenous house-keeping gene, Actin (Actin F and R).

TABLE 3

Primers for detection of ANG transgene and endogenous Actin expression.

| Primer Name | Primer Sequence | SEQ ID NO: |
|---|---|---|
| ANG_Forward (F) | 5' GAACGACATCAAGGCTATCTG 3' | 45 |
| ANG_Reverse (R) | 5' AGCACCGTATCTACAAGGAG 3' | 46 |
| Actin_Forward (F) | 5' CCCTCCCACATGCTATTCT 3' | 47 |
| Actin_Reverse (R) | 5' AGAGCCTCCAATCCAGACA 3' | 48 |
| oligo-dT_Reverse (R) | 5' TTCTAGAATTCAGCGGCCGCT$_{30}$RN 3' | 49 |
| poly-T_Reverse (R) | 5' TTCTAGAATTCAGCGGCCGCT 3' | 50 |

Each PCR sample was loaded onto an agarose gel, subjected to electrophoresis and the DNA was visualised (FIG. 39).

The integrity of the cDNA of both turboGFP and ANG transfected protoplast samples was confirmed by the presence of a band of expected size (524 bp) from samples amplified with the Actin primers. (FIG. 39, lanes 9 and 11, respectively). Confirmation that product amplification does not occur from the transfected DNA template can be observed by the absence of a band from both turboGFP and ANG transfected protoplast samples amplified with the same primers to which no reverse-transcriptase was added (FIG. 39, lanes 8 and 10).

Expression of Angiogenin was confirmed by the presence of a band of expected size (138 bp) in samples amplified with primers to ANG from cells transfected with 1031308 AtRbcS-p_ANG_nos-t (FIG. 29, lane 4) and the absence of a band in samples with the same primers to which no reverse-transcriptase was added (FIG. 39, lane 3). A positive control performed with ANG primers and 1031308 AtRbcS-p_ANG_nos-t plasmid DNA is observed in FIG. 39, lane 6 and indicates the size of the expected fragment.

Monocot Protoplast Transfection of Angiogenin

Protoplasts were released from mesophyll tissue of the monocot, *Triticum aestivum* using the method described in Spangenberg and Potrykus, 1996. The viability of tobacco protoplasts was assessed using Evans Blue stain as described in Huang et al, 1986

(FIG. 40).

DNA from two plasmids encoding either an expression cassette designed to express the ANG protein under control of the TaRbcS promoter (1031308_AtRbcS-p_ANG_nos-t; FIGS. 14 and 15) or a control expression cassette designed to express the fluorescent reporter (dsRED) under control of the constitutive ubiquitin promoter from *Zea mays* (0957284 ZmUbi-p_dsRED_nos-t; FIG. 16), were purified. Plasmid DNA was delivered to aliquots of protoplasts cells. After 24 hours, successful delivery and gene expression were confirmed by visualisation of the fluorescent marker in the control samples (FIG. 41).

Transient Gene Expression and Detection of Angiogenin in Monocot Protoplasts

To detect expression of Angiogenin, DNA-free RNA was purified from protoplasts and cDNA was synthesised with a oligo-dT reverse primer (Table 3). RT-PCR analysis of each sample was conducted using forward primers designed to Angiogenin or Actin and a poly-T reverse primer (Table 3) designed to anneal to the adapter sequence of the oligo-dT primer from which cDNA was synthesised, ensuring that there was no amplification from plasmid template.

Each PCR sample was loaded onto an agarose gel, subjected to electrophoresis and the DNA was visualised (FIG. 42).

The integrity of the cDNA of all wheat protoplast samples was confirmed by the presence of a band of expected size (920 bp) from samples amplified with the Actin_F and poly-T R primer. (FIG. 42, lanes 8 and 10) and absence of a band from samples amplified with the same primers to which no reverse-transcriptase was added (FIG. 42, lanes 7 and 9).

Expression of Angiogenin (Rnase5) was confirmed by the presence of a band of expected size (740 bp) in samples amplified with primers to ANG_F and poly-T_R primer from cells transfected with 1031312 TaRbcS-p_ANG_nos-t (FIG. 42, lane 4) and the absence of a band in samples with the same primers to which no reverse-transcriptase was added (FIG. 42, lane 3) and from samples that were not transfected with 1031312 TaRbcS-p_ANG_nos-t (FIG. 42, lanes 1 and 2).

Example 9

*Agrobacterium*-Mediated Transformation of Canola (*Brassica napus*) for Expression of Chimeric Angiogenin Genes Binary vectors containing chimeric ANG genes under control of different promoters are used for *Agrobacterium*-mediated transformation of *Brassica napus* hypocotyl segments as outlined below and demonstrated in FIG. 43.

*Brassica napus* seeds are surface sterilised in 70% ethanol for 2 minutes, washed 3 times in sterile water then further surface sterilised in a solution containing 1% (w/v) Calcium hypochlorite and 0.1% (v/v) Tween 20 for 30 minutes. The seeds are washed at least 3 times in sterile water and planted in 120 ml culture vessels containing a solidified germination medium containing 1× Murashige and Skoog (Murashige and Skoog *Physiol. Plant,* 15: 473-497, 1962) macronutrients, 1× micronutrients and B5 organic vitamins, supplemented with 500 mg/L MES, 2% (w/v) sucrose at a pH of 5.8 with the addition of 4 g/L Gelrite. The vessels are incubated at 25° C. under 16 h light/8 h dark conditions for 7 days to encourage germination.

After 7 days, seedlings of *Brassica napus* (whole seedlings) are transferred to a liquid medium consisting of 1× Murashige and Skoog macronutrients, 1× micronutrients and B5 organic vitamins, supplemented with 500 mg/L MES, 3% (w/v) sucrose at a pH of 5.8. Seedlings are grouped together and the roots and cotyledons removed prior to cutting the hypocotyls into 7-10 mm sections and plating on 9×1.5 cm petri dishes containing a preconditioning medium consisting of 1× Murashige and Skoog macronutrients, 1× micronutrients and B5 organic vitamins, supplemented with 500 mg/L MES, 3% (w/v) sucrose at a pH of 5.8 solidified with 6.4 g/l Bacto-Agar.

Hypocotyl sections are cultured for 24 hours prior to inoculation with an *Agrobacterium* suspension $OD_{600}$=0.2 for 30 minutes consisting of 1× Murashige and Skoog macronutrients, 1× micronutrients and B5 organic vitamins, supplemented with 500 mg/L MES, 100 µM Acetosyringone, 3% (w/v) sucrose at a pH of 5.8.

Following inoculation, hypocotyl sections are blotted on sterile paper towels and transferred to 9×1.5 cm petri dishes containing 1× Murashige and Skoog macronutrients, 1× micronutrients and B5 organic vitamins, supplemented with 500 mg/L MES, 100 µM Acetosyringone, 1 mg/L 2,4-D, 3% (w/v) sucrose at a pH of 5.8 solidified with 8 g/l Bacto-Agar. Explants are incubated at 25° C. under 16 h light/8 h dark conditions for 72 hours for co-cultivation.

Following co-cultivation, 20-30 hypocotyl explants are transferred to 9×1.5 cm petri dishes containing a solidified selection medium consisting of 1× Murashige and Skoog macronutrients, 1×micronutrients and B5 organic vitamins, supplemented with 500 mg/L MES, 1 mg/L 2,4-D, 3% (w/v) sucrose at a pH of 5.8 solidified with 8 g/l Bacto-Agar, supplemented with 250 mg/l timentin and 10 mg/l hygromycin to select for hygromycin-resistant shoots. Plates are incubated at 25° C. under 16 h light/8 h dark conditions.

After 7 days hypocotyl explants are transferred to 9×2.0 cm petri dishes containing a solidified regeneration media consisting of 1× Murashige and Skoog macronutrients, 1× micronutrients and B5 organic vitamins, supplemented with 500 mg/L MES, 1 mg/L 2,4-D, 3% (w/v) sucrose at a pH of 5.8 solidified with 8 g/l Bacto-Agar, supplemented with 4 mg/l BAP, 2 mg/l Zeatin, 5 mg/l Silver Nitrate, 250 mg/l timentin and 10 mg/l hygromycin. Plates are incubated under direct light at 25° C. under fluorescent light conditions (16 hr light/8 hr dark photoperiod; 55 µmol $m^{-2}$ $sec^{-1}$) for 4 weeks to encourage shoot development.

Regeneration is monitored weekly and hypocotyl explants transferred to fresh 9×2.0 cm petri dishes containing solidified regeneration media, RM supplemented with 4 mg/l benzyladenine, 2 mg/l zeatin, 5 mg/l silver nitrate, 250 mg/l timentin and 10 mg/l hygromycin for 6-8 weeks to encourage shoot development.

Hygromycin-resistant ($Hyg^r$) shoots are transferred to 120 ml vessels containing solidified root induction medium, RIM1, consisting of 1× Murashige and Skoog macronutrients, 1× micronutrients and B5 organic vitamins, supplemented with 500 mg/L MES, 1 mg/L 2,4-D, 1% (w/v) sucrose at a pH of 5.8 solidified with 8 g/l Bacto-Agar supplemented with 250 mg/l timentin. Shoots are incubated under direct fluorescent light at 25° C. (16 hr light/8 hr dark photoperiod; 55 µmol $m^{-2}$ $sec^{-1}$) to encourage shoot elongation and root development over 4-5 weeks. All $Hyg^r$ shoots with developed shoot and root systems are transferred to soil and grown under glasshouse conditions.

Example 10

Biolistic Transformation of Wheat (*Triticum aestivum* L.) for Expression of Chimeric Angiogenin Genes Transformation vectors containing chimeric ANG genes are used for biolistic transformation of wheat (*Triticum aestivum* L. MPB Bobwhite 26) as outlined below.

Step 1 (Donor Plant Production):

*Triticum aestivum* (Bobwhite 26) seed is used for the production of donor plant material. Wheat plants are grown in a nursery mix consisting of composted pine bark, perlite and vermiculite, with five plants per pot to a maximum pot size of 20 cm. Plants are kept under glasshouse conditions at approximately 22-24° C. for 12-16 weeks (FIG. 45A). Once the first spike emerges from the flag leaf, plants are tagged and embryos collected from the tallest heads 12-15 days post anthesis.

Step 2 (Day 1):

Spikes at the desired stage of development are harvested (FIG. 45B). Caryopsis are removed from the spikes and surface sterilised for 20 minutes in a 0.8% (v/v) NaOCl solution and rinsed at least four times in sterile distilled water.

Embryos up to 10 mm in length are aseptically excised from each caryopsis (removing the axis) using a dissecting microscope and cultured axial side down on an osmotic medium (E3maltose) consisting of 2× Murashige and Skoog (1962) macronutrients, 1× micronutrients and organic vitamins, 40 mg/L thiamine, 150 mg/L L-asparagine, supplemented with 15% (w/v) maltose, 0.8% (w/v) Sigma-agar and 2.5 mg/L 2,4-D (FIGS. 45C and D). Embryos are cultured on 60 mm×15 mm clear polypropylene petrie dishes with 15 mL of media. Culture plates are incubated at 24° C. in the dark for 4 hours prior to bombardment. Embryos are bombarded using a BioRad PDS1000 gene gun at 900 psi and at 6 cm with 1 µg of vector plasmid DNA precipitated onto 0.6 µm gold particles. Following bombardment, embryos are incubated overnight in the dark on the osmotic media.

Step 3 (Day 2):

Embryos are transferred to a callus induction medium (E3calli) consisting of 2× Murashige and Skoog (1962) macronutrients and 1× micronutrients and organic vitamins, 40 mg/L thiamine, 150 mg/L L-asparagine, supplemented with 6% (w/v) sucrose, 0.8% (w/v) Sigma-agar and 2.5 mg/L 2,4-D. Embryos are cultured for two weeks at 24° C. in the dark.

Step 4 (Day 16):

After 2 weeks of culture on E3calli, embryos have produced embryogenic callus and are subcultured onto a selection medium (E3Select) consisting of 2× Murashige and Skoog (1962) macronutrients and 1× micronutrients and organic vitamins, 40 mg/L thiamine, 150 mg/L L-asparagine, supplemented with 2% (w/v) sucrose, 0.8% (w/v) Sigma-agar, 5 mg/L of D,L phosphinothricin (PPT) and no plant growth regulators (FIGS. 45E-G). Cultures are incubated for further 14 days on E3Select at 24° C. in the light and a 12-hour photoperiod.

Step 5 (Day 30):

After 14 days culture on E3Select, embryogenic callus is sub-cultured onto fresh E3Select for a further 14 days (FIGS. 45E-G).

Step 6 (Day 44):

After about 4 weeks on E3Select, developing plantlets are excised from the embryonic callus mass and grown for a further three weeks in 65 mm×80 mm or 65 mm×150 mm polycarbonate tissue culture vessels containing root induction medium (RM). Root induction medium consists of 1× Murashige and Skoog (1962) macronutrients, micronutrients and organic vitamins, 40 mg/L thiamine, 150 mg/L L-asparagine, supplemented with 2% (w/v) sucrose, 0.8% (w/v) Sigma-agar, and 5 mg/L of PPT (FIG. 45H). Remaining embryogenic callus is sub-cultured onto E3Select for another 14 days.

Step 7 (Day 65+):

Regenerated plantlets surviving greater than 3 weeks on RM with healthy root formation are potted into a nursery mix consisting of peat and sand (1:1) and kept at 22-24° C.

with elevated humidity under a nursery humidity chamber system. After two weeks, plants are removed from the humidity chamber and hand watered and liquid fed Aquasol™ weekly until maturity. The $T_0$ plants are sampled for genomic DNA and molecular analysis. Ti seed is collected and planted for high-throughput Q-PCR analysis.

Example 11

Agrobacterium-Mediated Transformation of Wheat (*Triticum aestivum* L.) for Expression of Chimeric Angiogenin Genes Agrobacterium-mediated transformation of bread wheat is represented in FIG. 45. Wheat donor plants ready are harvested for use as source of embryo explants for *Agrobacterium* mediated transformation. Post infection from Agrobacterium, callus material is regenerated on tissue culture medium under appropriate selection until regenerating shoots are observed. Following several rounds of selection the rooted plant is potted in soil.

Example 12

Agrobacterium-Mediated Transformation of Tobacco (*Nicotiana benthamiana*) for Expression of Chimeric Angiogenin Genes In tobacco *Agrobacterium*-transformation adventitious shoots can be regenerated at high frequencies from leaf explants. *Agrobacterium*-mediated tobacco transformation is a four stage process.
1. Inoculation of regenerative explants with a cell suspension of *Agrobacterium*.
2. Co-cultivation of inoculated explants on regeneration medium for 2-3 days during gene transfer occurs.
3. Regeneration and selection of transformed shoots and the elimination of bacteria.
4. Biochemical and molecular analysis of putative transgenic plants.

Example 13

Agrobacterium-Mediated Transformation of Alfalfa (*Medicago sativa*) for Expression of Chimeric Angiogenin Genes Binary vectors containing chimeric ANG genes under control of different promoters are used for *Agrobacterium*-mediated transformation of *Medicago sativa* petiole explants from highly-regenerable alfalfa (*M. sativa*) clones.

Following co-cultivation with *Agrobacterium tumefaciens* strain LBA 4404 harbouring the binary vector, the alfalfa explants were washed with medium containing cefotaxime and used for induction of embryogenic callus under selective medium containing 25 mg/l kanamycin. Transgenic embryogenic alfalfa calli were recovered and allowed to regenerate transgenic alfalfa shoots, which were transferred on rooting medium leading to the recovery of transgenic alfalfa plants expressing chimeric ANG genes.

Example 14

Biolistic Transformation of Perennial Ryegrass (*Lolium perenne*) for Expression of Chimeric Angiogenin Genes Biolistic co-transformation of perennial ryegrass with the vectors containing the TaRbcS and LpRbcS regulatory sequences, driving the expression of the ANG gene (FIGS. 19, 20 and 21) and the pAcH1 vector for hygromycin resistance is conducted on embryogenic calli for perennial ryegrass. The pAcH1 vector was previously constructed and has been used successfully in plant transformation experiments (Bilang, et al., 1991; Spangenberg, et al., 1995a; Spangenberg, et al., 1995b; Ye, et al., 1997; Bai, et al., 2001). The perennial ryegrass biolistic transformation method is outlined in FIG. 44.

Example 15

Agrobacterium-Mediated Transformation of White Clover (*Trifolium repens*) for Expression of Chimeric Angiogenin Genes Vectors containing chimeric ANG genes under control of different promoters are used for *Agrobacterium*-mediated transformation of *Trifolium repens* cotelydons as outlined below.

All material in tissue culture are grown at 24° C. with a 16 h light/8 h dark regime. White clover seeds are washed in 70% v/v ethanol, surface-sterilised in 1.5% sodium hypochlorite (12.5 g/L active chlorine), rinsed in sterile distilled water and imbibed overnight at 4° C. in the dark. Cotyledonary explants are excised with a 1-2 mm segment of hypocotyl attached. Explants are incubated in *Agrobacterium* culture ($OD_{600}$=approx 0.35) for 40 min and co-cultivated on regeneration medium, consisting of: 1× Murashige and Skoog Basal Medium (Sigma), 30 g/L sucrose, 5 M thidiazuron (Sigma), 0.5 M naphthalene-acetic acid, 250 mg/L cefotaxime (Claforan, Hoechst) and 8 g/L Bacto-Agar (Becton-Dickinson), pH 5.75, supplemented with 40 mg/L acetosyringone. Explants are co-cultivated for 3 days at 24° C., and transferred to regeneration medium containing an appropriate selective agent and are subcultured every 2-3 weeks. Regenerated shoots are transferred to root-inducing medium, consisting of: 1×MS basal medium, 15 g/L sucrose, 1.2 M indole-butyric acid, 250 mg/L cefotaxime, an appropriate selective agent and 8 g/L Bacto-Agar, pH 5.75. Antibiotic-resistant plantlets are transferred to soil and established under glasshouse conditions. The white clover *Agrobacterium*-mediated transformation method is demonstrated in FIG. 46.

Example 16

Production of Transgenic White Clover Plants Expressing Chimeric Angiogenin Genes Use of constructs containing a light regulated promoter and endoplasmic reticulum retention signal The AtRbcS_ANG_35S expression cassette was incorporated into a vector backbone containing a selectable marker cassette of the neomycin phosphotransferase (npt II) gene driven by the nopaline synthase (nos) promoter and terminator sequences (FIG. 47). This vector was inserted into the white clover genome by *Agrobacterium* mediated transformation.

Example 17

Characterisation of Transgenic White Clover Plants Expressing Chimeric Angiogenin Genes Detection of Angiogenin Expression in Transgenic White Clover Total RNA was extracted from leaves and stems of white clover transformed with AtRbcS_ANG_35S and an untransformed control. Reverse transcriptase polymerase chain reaction (RT-PCR) analysis was performed using primers specific to the angiogenin gene to detect angiogenin expression in the transgenic plants (FIG. 48).

Detection of the Angiogenin Protein in Transgenic White Clover

Total protein extract was obtained from non-transgenic (control) and transgenic white clover plant tissue and separated using 2DE gel apparatus. Two dimensional protein profiles were compared between the non-transgenic and transgenic plants. The transgenic tissue was observed to contain a rich protein spot not observed in the control material (FIG. 49). The MOWSE scoring algorithm was used to determine the identity of this rich protein spot in the transgenic white clover leaf. This was achieved as follows.

The protein spot of interest was excised from the 2DE gel and digested with overnight porcine trypsin. The digested protein sample was then C18 zip-tipped and spotted onto an MALDI-TOF/TOF mass spectrometry target. The spotted protein sample was then sequenced using MALDI-TOF/TOF mass spectrometry (FIG. 50). The observed peptide masses obtained from the peptide mass fingerprint data and the observed peptide ion fragmentation masses obtained from the peptide ion fragmentation pattern were then combined together and searched against the NCBInr sequence database of known calculated peptide masses and known calculated ion fragmentation masses. The mass spectra obtained by MALDI-TOF/TOF mass spectrometry matched bovine angiogenin in the NCBInr sequence database. The protein score and ion scores received were positive for bovine angiogenin using the MOWSE scoring algorithm.

Protein Quantification of Bovine Angiogenin in Soluble Transgenic White Leaf Clover Leaf Extract Approximately, 50 µg of the soluble transgenic white clover leaf extract was loaded on to the 2DE gel. Bovine angiogenin represents 10% of the soluble transgenic white clover leaf extract and is therefore 5 µg of the soluble transgenic white clover leaf extract. This was determined by densitometry using Progenesis PG240 software (Non Linear Dynamics, Newcastle upon Tyne, UK).

The soluble transgenic white clover leaf extract was prepared by homogenising 200 mg of ground plant tissue in 1.5 ml of homogenisation buffer. The level of expression in transgenic white clover leaf equates to 7.5 µg of bovine angiogenin per milligram of plant extract. This level is equivalent to angiogenin expression in bovine cow's milk which is between 4-8 mg/ml.

Example 18

Production of Transgenic Plants Co-Expressing Angiogenin and Other Proteins for Enhanced Angiogenin Productivity It would be possible to pyramid existing technologies to generate a significant impact on the efficacy of a variety of applications by increasing the range of productivity in plants.

The productivity of angiogenin expressed in plants may be enhanced through co-expression with antimicrobials, protease inhibitors, RNase inhibitors, follistatin or delayed plant organ senescence nucleic acids and constructs.

Technologies for the extend life of plants (patent PCT/AU01/01092), increased biomass and high fructans (patent PCT/AU2009/001211), have been established. Pyramiding the current application technology with technologies that address these other factors should greatly increase plant health and production which should, in turn, increase animal health and production, as well as enhance the generation of value added products in plant biomass.

Example 19

Agrobacterium-Mediated Transformation of Arabidopsis (Arabidopsis thaliana) for Expression of Chimeric Angiogenin Genes Vectors containing chimeric ANG genes under control of different promoters are used for Agrobacterium-mediated transformation of Arabidopsis thaliana as outlined below.

1. Inoculation with a cell suspension of Agrobacterium to Arabidopsis using infiltration to facilitate access of Agrobacterium to immature flowers where T-DNA transfer may then take place.
2. Plant growth and monitoring and collection of potentially transgenic seed.
3. Regeneration and selection of transformed seeds on germination media with appropriate selection antibiotic.
4. Biochemical and molecular analysis of putative transgenic plants.

Example 20

Production of Transgenic Arabidopsis Plants Containing Chimeric Angiogenin Genes Use of constructs containing a light regulated promoter and endoplasmic reticulum retention signal The AtRbcS_ANG_nos expression cassette (FIG. 11) was incorporated into a vector backbone containing a selectable marker cassette of the hygromycin phsophotransferase (hp-tII) gene driven by the CSVMV promoter and CaMV35S terminator sequences (FIG. 18). This vector was inserted into the Arabidopsis genome by Agrobacterium mediated transformation.

Example 21

Characterisation of Transgenic White Clover Plants Containing Chimeric Angiogenin Genes Detection of the Angiogenin Gene in Transgenic Arabidopsis DNA was extracted from Arabidopsis leaves of two different transgenic lines with AtRbcS_ANG_nos and a wild-type untransformed control. Polymerase chain reaction (PCR) analysis was performed using primers specific to the angiogenin gene (Table 3) to detect the presence of the angiogenin gene in the transgenic plant lines (FIG. 51).

REFERENCES

Abenes, M., Holbrook, L., and Moloney, M. (1997) Transient expression and oil body targeting of an Arabidopsis oleosin-GUSreporter fusion protein in a range of oilseed embryos. Plant Cell Reports, 17:1-7.

Acharya, K. R., Shapiro, R., SC, Allen, S. C., Riordan, J. F., Vallee, B. L. Crystal structure of human angiogenin reveals the structural basis for its functional divergence from ribonuclease.

Baghdady, A., Blervacq, A., Jouanin, L., Grima-Pettenati, J., Sivadon, P., Hawkins, S. (2006) Eucalyptus gunnii CCR and CAD2 promoters are active in lignifying cells during primary and secondary xylem formation in Arabidopsis thaliana. Plant Physiol. Biochem., 44:674-683.

Bai, Y., et al. (2001) Genetic transformation of elite turf-type cultivars of Tall Fescue. International Turfgrass Society Research Journal, 9: 129-136.

Bilang, R., et al. (1991) The 3'-terminal region of the hygromycin-B-resistance gene is important for its activity in Escherichia coli and Nicotiana tabacum. Gene, 100: 247-250.

Bond, M. D., and Vallee, B. L. (1988). Isolation of bovine angiogenin using a placental ribonuclease inhibitor binding assay. *Biochemistry* 27: 6282-6287.

Borisjuk, N., Sitailo, L., Adler, K., Malysheva, L., Tewes, A., Borisjuk, L., Manteuffel, R. (1998) Calreticulin expression in plant cells: developmental regulation, tissue specificity and intracellular distribution. *Planta*, 206: 504-14.

Chen, Z. et al. (1988) A DNA sequence element that confers seed-specific enhancement to a constitutive promoter. *EMBO J.*, 7:297-302.

Christensen, A. H., et al. (1992). Maize polyubiquitin genes: structure, thermal perturbation of expression and transcript splicing, and promoter activity following transfer to protoplasts by electroporation. *Plant Mol Biol.*, 18: 675-689.

Daniell, H., Kumar, S. and Dufourmantel, N. (2005) Breakthrough in chloroplast genetic engineering of agronomically important crops. *TRENDS in Biotechnology*, 23: 238-245.

Denecke, j., Botterman, J. and Deblaere, R. (1990) Protein secretion in plant cells can occur via a default pathway. *Plant Cell*, 2: 51-59.

Doczi, R., et al. (2005) Conservation of the drought-inducible DS2genes and divergences from their ARS paralogues in solanaceous species. *Plant Phys. Biochem.*, 43: 269-276.

Fedorova, T. V., Komolova, G. S., Rabinovich, M. L., Tikhomirova, N. A., and Shalygina, A. M. (2002) Milk ultrafiltrate as a promising source of angiogenin. *Prikl. Biokhim. Mikrobiol.*, 38: 221-224.

Gao, X., Hu, H., Zhu, J. and Xu, Z. (2007) Identification and characterisation of folistatin as a noverl angiogenin-binding protein. *FEBS Lett.*, 581:5505-5510.

Gao, X., and Xu, Z. (2008) Mechanisms of action of angiogenin. *Acta Biochim Biophys Sin.*, 40: 619-24.

Gleba, D., Borisjuk, N. V., Borisjuk, L. G., Kneer, R., Poulev, A., Skarzhinskaya, M., Dushenkov, S., Logendra, S., Gleba, Y. Y. and Raskin, I. (1999) Use of plant roots for phytoremediation and molecular farming. *Proc. Natl. Acad. Sci. USA*, 96: 5973-5977.

Hara-Nishimura, I., Matsushima, R., Shimada T., Nishimura, M. (2004) Diversity and formation of endoplasmic reticulum-derived compartments in plants. Are these compartments specific to plant cells. *Plant Physiol.*, 136: 3435-3439.

Harper, J. W., Vallee, B. L. (1988) Conformational characterization of human angiogenin by limited proteolysis. *J Protein Chem.*, 7: 355-363.

Hashizume, F., Hino, S., Kakehashi, M., Okajima, T., Nadano, Aoki D. N. and Matsuda, T. (2008) Development and evaluation of transgenic rice seeds accumulating a type II-collagen tolerogenic peptide. *Transgenic Res.*, 17: 1117-1129

Hauffe K. D., Lee S. P., Subramaniam R., Douglas C. J. (1993) Combinatorial interactions between positive and negative cis-acting elements control spatial patterns of 4CL-1 expression in transgenic tobacco. *Plant J.*, 4: 235-253.

Huang, C. N., Cornejo, M. J., Bush, D. S., Jones, R. L. (1986) Estimating Viability of Plant Protoplasts Using Double and Single Staining. *Protoplasma*, 135:80-87.

Herbers, K., et al. (1994) Cloning and characterization of a cathepsin D inhibitor gene from *Solanum tuberosum* L. *Plant Mol Biol.*, 26:73-83.

Hu, H, goa, X., Sun, Y., Zhou, J., Yang, M. and Xu, Z. (2005) alpha-actin-2, a cytoskeletal protein binds to angiogenin. *Biochem. Biophys. Res. Commun.* 329: 661-667.

Jin, L. and Lui, J. (2008) Molecular cloning, expression profile and promoter analysis of the novel ethylene responsive transcription factor gene GhERF4 from cotton. *Plant Phys Biochem.*, 46: 46-53.

Kay, R., et al. (1987). Duplication of CaMV35S promoter sequences creates a strong enhancer for plant genes. *Science*, 236: 1299-1302.

Keller, B. and Baumgartner C. (1991) Vascular-Specific Expression of the Bean GRP 1.8 Gene Is Negatively Regulated. *Plant Cell*, 3: 1051-1061.

Kishimoto K, et al., (2005) Endogenous angiogenin in endothelial cells is a general requirement for cell proliferation and angiogenesis. *Oncogene*, 24:445-456.

Kragler F, Lametschwandtner G, Christmann J, Hartig A, Harada JJ. (1998) Identification and analysis of the plant peroxisomal targeting signal 1 receptor NtPEX5. *Proc. Natl. Acad. Sci. USA*, 95: 13336-41.

Kwak, M., et al. (2005) Two sweet potato ADP-glucose phsophorylase isoforms are regulated antagonistically in response to sucrose content in storage roots. *Gene*, 366: 87-96.

Lamacchia, C., Shewry, P. R., Di Fonzo, N., Forsyth, J. L., Harris, N., Lazzeri, P. A., Napier, J. A., Halford, N. G., Barcelo, P., (2001) Endosperm-specific activity of a storage protein gene promoter in transgenic wheat seed. *J Exp Bot.* 52:243-50.

Lee, W. S., Tzen, J. T., Kridl, J. C., Radke, S. E. and Huang, A. H. (1991) Maize oleosin is correctly targeted to seed oil bodies in *Brassica napus* transformed with the maize oleosin gene. *Proc. Natl. Acad. Sci. USA*, 88: 6181-6185.

Li M., Singh, R., Bazanova, N., Milligan, A. S., Shirley, N., Langridge, P., Lopato, S., (2008) Spatial and temporal expression of endosperm transfer cell-specific promoters in transgenic rice and barley. *Plant Biotechnol J.* 6:465-476.

Li, X., et al. (2001) Sucrose regulation of ADP-glucose pyrophosphorylase subunit genes transcript levels in leaves and fruit. *Plant Science*, 162: 239-244.

Lin, K., et al. (2008) Generation and analysis of the transgenic potatoes expressing heterologous Thermostable B-amylase. *Plant science*, 174: 649-657.

Liu, D., et al. (2003) High transgene expression levels in sugarcane (*Saccharum officinarum* L.) driven by the rice ubiquitin promoter RUBQ2. *Plant Science*, 165: 743-750.

Markert, Y., Koditz, J., Mansfeld, J., Arnold, U., Ulbrich-Hofmann, R. (2001) Increased proteolytic resistance of ribonuclease A by protein engineering. *Protein Eng.*, 14: 791-796.

Marraccini, P., Deshayes, A., Pétiard, P., Rogers, W. J. (1999) Molecular cloning of the complete 11S seed storage protein gene of *Coffea arabica* and promoter analysis in transgenic tobacco plants. *Plant Physiol. Biochem.*, 37: 273-282.

Marty, F. (1999) Plant Vacuoles. *Plant Cell*, 11: 587-600.

McElroy, D., et al. (1990). Isolation of an efficient actin promoter for use in rice transformation. *Plant Cell*, 2: 163-171.

Murray, E. E, Lotzer, J. and Eberle, M. (1989) Codon usage in plants. *Nuleic Acids Research*, 17:477-498.

Ouellet, F., et al. (1998) The wheat wcs120 promoter is cold-inducible in both monocottyledeonous and dicotelydonous species. *FEBS Letters*, 423: 324-328.

Pedersen, K., Devereux, J., Wilson, D. R., Sheldon, E. and Larkins, B. A. (1982) Cloning and sequence analysis reveal structural variation among related zein genes in maize. *Cell,* 29: 1015-1026.

Ramírez, Y., Tasciotti, E., Gutierrez-Ortega, A., and Torres, A. J. D. (2007) Fruit-Specific Expression of the Human Immunodeficiency Virus Type 1 Tat Gene in Tomato Plants and Its Immunogenic Potential in Mice. *Clin Vaccine Immunol.* 14: 685-692.

Romero, H., et al. (2006) Expression profile analysis and biochemical properties of the peptide methionine sulfoxide reductase A (PMSRA) gene family in *Arabidopsis. Plant Science,* 170: 705-714.

Sasanuma, (2001). Characterization of the rbcS multigene family in wheat: subfamily classification, determination of chromosomal location and evolutionary analysis. *Mol Genetics Genomics,* 265: 161-171.

Schernthaner, J. P., Matzke, M, A, Matzke, A. J., (1988) Endosperm-specific activity of a zein gene promoter in transgenic tobacco plants. *EMBO J.* 7:1249-1255.

Schunmann, P. H. D., Richardson, A. E., Smith, F. W. and Delhaize, E. (2004) Characterization of promoter expression patterns derived from the Pht1 phosphate transporter genes of barley (*Hordeum vulgare* L.). *Journal of Experimental Botany,* 55: 855-865.

Selinger, D. A., Lisch, D. and Chandler, V. L. (1998) The Maize Regulatory Gene B-Peru Contains a DNA Rearrangement That Specifies Tissue-Specific Expression Through Both Positive and Negative Promoter Elements. *Genetics,* 149: 1125-1138.

Siebertz, B., et al. (1989) cis-Analysis of the wound inducible promoter wun-1 in transgenic tobacco plants and histochemical localisation of its expression. *The Plant Cell,* 1: 960-968.

Spangenberg, G., et al. (1995a). Transgenic tall fescue and red fescue plants from microprojectile bombardment of embryogenic suspension cells. *J Plant Physiol.,* 145: 693-701.

Spangenberg, G. and Potrykus, I. (1996) Polyethylene glycol-mediated direct gene transfer to tobacco protoplasts and regeneration of transgenic plants: Gene transfer to plants (eds. I Potrykus and G. Spangenberg, Springer-Verlag Berlin, Heidelberg New York, pp 59-65)

Shapiro, R. and Vallee, B. L. (1987) Human placental ribonuclease inhibitor abolishes both angiogenic and ribonucleolytic activities of angiogenin. *Proceedings of the National Academy of Sciences USA,* 84: 2238-2241.

Spangenberg, G., et al. (1995b). Transgenic perennial ryegrass (*Lolium perenne*) plants from microprojectile bombardment of embryogenic suspension cells. *Plant Sci.,* 108: 209-217.

Stark, D. et al. (1992) Regulation of the Amount of Starch in Plant Tissues by ADP Glucose Pyrophosphorylase. *Science,* 258: 287-292.

Szopa, J., et al. (2003) Structural organisation, expression, and promoter analysis of a 16R isoform of 14-3-3 protein gene from potato. *Plant Phys Biochem.,* 41: 417-423.

Takayoshi Koyama, Toshiro Ono, Masami Shimizu, Tetsuro Jinbo, Rie Mizuno, Keiji Tomita, Norihiro Mitsukawa, Tetsu Kawazu, Tetsuya Kimura, Kunio Ohmiya and Kazuo Sakka (2005) Promoter Of *Arabidopsis Thaliana* Phosphate Transporter Gene Drives Root-Specific Expression of Transgene in Rice. *Journal of Bioscience and Bioengineering,* 99: 38-42.

Tran, L. et al. (2004) Isolation and functional analysis of *Arabidopsis* stress-inducible NAC transcription factors that bind to a drought-responsive cis-element in the early responsive to dehydration stress 1 promoter. *Plant Cell,* 16: 2481-98.

Wan, B., et al. (2007) Expression of rice $Ca^{2+}$-dependent protein kinases (CDPKs) genes under different environmental stresses. *FEBS Letters,* 581: 1179-1189.

Xiangwei, G., et al., (2007) Identification and characterization of follistatin as a novel angiogenin-binding protein. *FEBS letters,* 581: 5505-5510.

Xu, Z., Monti D. M., and Hu, G. (2001) Angiogenin activates human umbilical artery smooth muscle cells. Biochem Biophysi Res Commun, 285: 909-914.

Yamaguchi-Shinozaki K. and Shinozaki K. (1993) Characterisation of the expression of a desiccation-responsive rd29 gene of *Arabidopsis thaliana* and analysis of its promoter in transgenic plants. *Mol. Gen. Genet.,* 236: 331-340.

Yang, N. S. and Russell, D. (1990) Maize sucrose synthase-I promoter directs phloem cell-specific expression of GUS gene in transgenic tobacco plants. *Proc. Natl. Acad. Sci. USA,* 87: 4144-4148.

Ye, X., et al. (1997) Transgenic Italian ryegrass (*Lolium multiflorum*) plants from microprojectile bombardment of embryogenic suspension cells. *Plant Cell Rep.,* 16: 379-384.

Zeng, W. K., et al. (1995). PCR Amplification and Sequencing of a Wheat rbcS Gene Promoter. *Acta Bot Sinica* 37: 496-500.

Zhang, X., et al. (2004) The indigenous plasmid pQBR103 encodes plant-inducible genes, including three putative helicases. *FEMS Micro. Ecol.,* 51: 9-17.

Zhang, H., et al., (2008) Interaction between angiogenin and fibulin 1: Evidence and implication. *Acta Biochimica et Biophysica Sinica,* 40: 375-380.

Zoubenko, O. V., Allison, L. A., Svab, Z. and Maliga, P. (1994) Efficient targeting of foreign genes into the tobacco plastid genome. *Nucleic Acids Res.,* 22: 3819-3824.

SEQUENCE LISTING

```
<160> NUMBER OF SEQ ID NOS: 53

<210> SEQ ID NO 1
<211> LENGTH: 447
<212> TYPE: DNA
<213> ORGANISM: Bos taurus

<400> SEQUENCE: 1
atggtcatgg tcctgagccc cctgttttg  gtcttcatac tgggtctggg tctgacccca        60
gtggccccgg ctcaagatga ctacagatac atacacttcc tgacccagca ctacgatgcc       120
```

```
aaaccaaagg gccggaatga cgaatattgt tttaacatga tgaaaaatcg acgcctgacc    180
agaccttgca aagaccgcaa caccttatt catggcaaca agaatgacat taaggccatc    240
tgtgaggaca gaaatggaca gccttacaga ggcgatctca gaataagcaa gtctgaattc    300
cagatcacca tctgcaagca taaggaggt tcctcccggc ctccatgccg gtacggagcc    360
acagaagact ccagagtcat tgttgtcggc tgtgaaaatg gcttgcccgt ccactttgat    420
gagtccttta tcactccacg ccactag                                        447
```

<210> SEQ ID NO 2
<211> LENGTH: 148
<212> TYPE: PRT
<213> ORGANISM: Bos taurus

<400> SEQUENCE: 2

```
Met Val Met Val Leu Ser Pro Leu Phe Leu Val Phe Ile Leu Gly Leu
1               5                   10                  15
Gly Leu Thr Pro Val Ala Pro Ala Gln Asp Asp Tyr Arg Tyr Ile His
            20                  25                  30
Phe Leu Thr Gln His Tyr Asp Ala Lys Pro Lys Gly Arg Asn Asp Glu
        35                  40                  45
Tyr Cys Phe Asn Met Met Lys Asn Arg Arg Leu Thr Arg Pro Cys Lys
    50                  55                  60
Asp Arg Asn Thr Phe Ile His Gly Asn Lys Asn Asp Ile Lys Ala Ile
65                  70                  75                  80
Cys Glu Asp Arg Asn Gly Gln Pro Tyr Arg Gly Asp Leu Arg Ile Ser
                85                  90                  95
Lys Ser Glu Phe Gln Ile Thr Ile Cys Lys His Lys Gly Gly Ser Ser
            100                 105                 110
Arg Pro Pro Cys Arg Tyr Gly Ala Thr Glu Asp Ser Arg Val Ile Val
        115                 120                 125
Val Gly Cys Glu Asn Gly Leu Pro Val His Phe Asp Glu Ser Phe Ile
    130                 135                 140
Thr Pro Arg His
145
```

<210> SEQ ID NO 3
<211> LENGTH: 447
<212> TYPE: DNA
<213> ORGANISM: Artificial Sequence
<220> FEATURE:
<223> OTHER INFORMATION: Modified Bos taurus sequence

<400> SEQUENCE: 3

```
atggtcatgg tcctgagccc cctgttcctg gtcttcatcc tgggtctggg tctgacccca    60
gtggccccag ctcaagatga ctacagatac atccacttcc tgacccagca ctacgatgcc   120
aaaccaaagg gccggaacga cgagtactgc ttcaacatga tgaagaaccg acgcctgacc   180
agaccttgca aagaccgcaa caccttcatc cacggcaaca gaacgacat caaggccatc    240 tgtgaggaca gaaatggaca gccttacaga ggcgatctca gaatcagcaa gtctgagttc    300
cagatcacca tctgcaagca taaggaggt tcctcccggc ctccatgccg gtacggagcc    360
acagaagact ccagagtcat tgttgtcggc tgtgagaatg gcttgcccgt ccactttgat    420
gagtccttta tcactccacg ccactag                                        447
```

<210> SEQ ID NO 4

<211> LENGTH: 444
<212> TYPE: DNA
<213> ORGANISM: Homo sapiens

<400> SEQUENCE: 4

```
atggtgatgg gcctgggcgt tttgttgttg gtcttcgtgc tgggtctggg tctgacccca      60
ccgaccctgg ctcaggataa ctccaggtac acacacttcc tgacccagca ctatgatgcc     120
aaaccacagg gccgggatga cagatactgt gaaagcatca tgaggagacg gggcctgacc     180
tcaccctgca aagacatcaa cacatttatt catggcaaca agcgcagcat caaggccatc     240
tgtgaaaaca gaatggaaa ccctcacaga gaaaacctaa gaataagcaa gtcttctttc     300
caggtcacca cttgcaagct acatggaggt tcccctggc ctccatgcca gtaccgagcc     360
acagcggggt tcagaaacgt tgttgttgct tgtgaaaatg gcttacctgt ccacttggat     420
cagtcaattt tccgtcgtcc gtaa                                              444
```

<210> SEQ ID NO 5
<211> LENGTH: 444
<212> TYPE: DNA
<213> ORGANISM: Gorilla gorilla

<400> SEQUENCE: 5

```
atggtgatgg gcctgggcgt tttgttgttg gtcttcgtgc tgggtctggg tctgacccca      60
ccgaccctgg ctcaggataa ctccaggtac acacacttcc tgacccagca ctatgatgcc     120
aaaccacagg gccgggatga cagatactgt gaaagcatca tgaggagacg gggcctgacc     180
tcaccctgca aagacatcaa cacatttatt catggcaaca agcgcagcat caaggccatc     240
tgtgaaaaca gaatggaaa ccctcacaga gaaaacctaa gaataagcaa gtcttctttc     300
caggtcacca cttgcaagct acatggaggg tcccctggc ctccatgcca gtaccgagcc     360
acagcggggt tcagaaacgt tgttgttgct tgtgaaaatg gcttacctgt ccacttggat     420
cagtcaattt tccgtcgtcc gtaa                                              444
```

<210> SEQ ID NO 6
<211> LENGTH: 444
<212> TYPE: DNA
<213> ORGANISM: Pan troglodytes

<400> SEQUENCE: 6

```
atggtgatgg gcctgggcgt tttgttgttg gtcttcgtgc tgggtctggg tctgacccca      60
ccgaccctgg ctcaggataa ctccaggtac acacacttcc tgacccagca ctatgatgcc     120
aaaccacagg gccgggatca cagatactgt gaaagcatca tgaggagacg gggcctgacc     180
tcaccctgca aagacatcaa cacatttatt catggcaaca agcgcagcat caaggccatc     240
tgtgaaaaca gaatggaaa ccctcacaga gaaaacctaa gaataagcaa gtcttctttc     300
caggtcacca cttgcaagct acatggaggg tcccctggc ctccatgcca gtaccgagcc     360
acagcggggt tcagaaacgt tgttgttgct tgtgaaaatg gcttacctgt ccacttggat     420
cagtcaattt tccgtcgtcc gtaa                                              444
```

<210> SEQ ID NO 7
<211> LENGTH: 441
<212> TYPE: DNA
<213> ORGANISM: Macaca mulatta

<400> SEQUENCE: 7

```
atggtgatgg gcctgggcct tttcttgttg gtcttcatgc tgggtctggg tctgacccca      60
```

```
cccaccctgg ctcaggataa ctccaggtac agagacttcc tgaccaagca ctatgatgcc      120
acaccacagg gccggaatga cagatactgt gaaagcatga tgaggagacg gggcctgacc      180
tcaccctgca aagacatcaa cacctttatt catggcaaca gtcgccacat caaggccatc      240
tgtggagatg agaatggaaa cccttacgga gaaaacctaa gaataagcaa gtctcctttc      300
caggtcacca cttgcaacct acgtggagga tcctcccggc tccatgccg gtaccgagcc       360 acagcagggt tcagaaacat tgttgttgct tgtgaaaatg acctgcctgt ccacttggat      420
cagtcaattt tccgtccgta a                                                441

<210> SEQ ID NO 8
<211> LENGTH: 441
<212> TYPE: DNA
<213> ORGANISM: Equus caballus

<400> SEQUENCE: 8
atggcgatga gcctgtgccc cctgttgttg gtcttcgtgc tgggtctggg tctgacccca       60
ccatccctgg ctcaggatga ttccaggtac agacagttcc tgaccaagca ctatgatgcc      120
aatccaaggg gccggaatga cagatactgt gaaagcatga tggtgagacg acacctgacc      180
acaccctgca aagacaccaa cactttttat catggcagca gagcagcat caaggccatc       240 tgtggaaata agaatggaaa cccttacgga gaaactttaa gaataagcaa gactcgtttc      300
caggtcacca cttgcaagca tgcaggaggg tcccccggc tccatgccg atacagagcc        360 acaccagggt tcagaagcat tgtcattgcc tgtgaaaacg gcttgcctgt ccactttgat      420
gagtcctttt tccgtccata a                                                441

<210> SEQ ID NO 9
<211> LENGTH: 443
<212> TYPE: DNA
<213> ORGANISM: Sus scrofa

<400> SEQUENCE: 9
atggtgatat tgctgggccc cctgctgttg gtcttcatgc tgggtctggg tctggccccg       60
ctgagcctgg ctaaggatga agacaggtac acacacttcc tgacccagca ctacgatgcc      120
aaaccaaagg gccgggatgg cagatactgt gaaagcataa tgaagcaacg aggcctgacc      180
agaccctgca aagaggtcaa cacctttatt catggcacga ggaatgatat caaggccatc      240
tgtaatgata agaatggaga gccttacaac aatttcagaa gaagcaagtc tcctttccaa      300
attaccactt gcaagcataa gggagggtcc aaccggcctc catgtgggta cagggccaca      360
gcagggttca gaaccatagc tgttgcctgt gaaaatggct tgcctgtcca ctttgatgag      420
tcctttatca ttacaagcca gta                                              443

<210> SEQ ID NO 10
<211> LENGTH: 438
<212> TYPE: DNA
<213> ORGANISM: Rattus rattus

<400> SEQUENCE: 10
atggagatga gcctgcgtcc tctgttgttg gttttgtgc tgggtctggt ttcgacccct         60
tcaactctgg ctcaggacga ccccaggtac acgaagttcc tgactcagca ctatgatgcc      120
aagcccaagg gtcgggatgc cagatactgc gaaagtatga tgaggagaag aggcctaacc      180
tcgccctgca aagaggtcaa cacctttatc catggcaaca agggcagcat caaggccatc      240
```

```
tgtggcgcga atggaagccc ttacggagaa aacttaagaa taagccagtc tcccttccag    300
atcaccacct gcaagcatac aggagggtct ccccggcccc cttgccggta ccgagcctct    360
gcagggttca gacatgttgt tattgcctgt gaaaatggct tgcctgtcca ctttgatgag    420
tcttttatca gtctctag                                                  438

<210> SEQ ID NO 11
<211> LENGTH: 438
<212> TYPE: DNA
<213> ORGANISM: Mus musculus

<400> SEQUENCE: 11
atggcgataa gcccaggccc gttgttcttg atcttcgtgc tgggtctggt tgtgatccct     60
cccactctgg ctcaggatga ctccaggtac acaaaattcc tgactcagca ccatgacgcc    120
aagccaaagg gccgggacga cagatactgt gaacgtatga tgaagagaag aagcctaacc    180
tcaccctgca agatgtcaa cacctttatc catggcaaca agagcaacat caaggccatc    240
tgtggagcga atggaagccc ttacagagaa aacttaagaa tgagcaagtc tcccttccag    300
gtcaccactt gcaagcacac aggagggtct ccccggcctc catgccagta ccgagcctct    360
gcagggttca gacatgttgt tattgcctgt gagaatggct tgccggtcca cttcgatgag    420
tcatttttca gtctatag                                                  438

<210> SEQ ID NO 12
<211> LENGTH: 435
<212> TYPE: DNA
<213> ORGANISM: Gallus gallus

<400> SEQUENCE: 12
atgacaatga gcccatgtcc tttgttgttg gtcttcgtgc tgggtctggt tgtgattcct     60
ccaactctgg ctcagaatga agggtacgaa aaattcctac gtcagcacta tgatgccaag    120
ccaaagggcc gggacgacag atactgtgaa agtatgatga ggaaagaaa gctaacctcg    180 ccttgcaaag atgtcaacac ctttatccat ggcaccaaga aaacatcag gccatctgc     240 ggaaagaaag gaagccctta tggagaaaac ttcagaataa gcaattctcc cttccagatc    300
accacttgta cgcactcagg agcgtctccc aggcctccat gtgggtaccg agcctttaaa    360
gatttcagat atattgttat tgcctgtgaa gatggctggc ctgtccactt cgatgagtct    420
tttatcagtc cgtag                                                     435

<210> SEQ ID NO 13
<211> LENGTH: 147
<212> TYPE: PRT
<213> ORGANISM: Homo sapiens

<400> SEQUENCE: 13

Met Val Met Gly Leu Gly Val Leu Leu Val Phe Val Leu Gly Leu
1               5                  10                  15

Gly Leu Thr Pro Pro Thr Leu Ala Gln Asp Asn Ser Arg Tyr Thr His
            20                  25                  30

Phe Leu Thr Gln His Tyr Asp Ala Lys Pro Gln Gly Arg Asp Asp Arg
        35                  40                  45

Tyr Cys Glu Ser Ile Met Arg Arg Arg Gly Leu Thr Ser Pro Cys Lys
    50                  55                  60

Asp Ile Asn Thr Phe Ile His Gly Asn Lys Arg Ser Ile Lys Ala Ile
65                  70                  75                  80
```

```
Cys Glu Asn Lys Asn Gly Asn Pro His Arg Glu Asn Leu Arg Ile Ser
                85                  90                  95

Lys Ser Ser Phe Gln Val Thr Thr Cys Lys Leu His Gly Gly Ser Pro
            100                 105                 110

Trp Pro Pro Cys Gln Tyr Arg Ala Thr Ala Gly Phe Arg Asn Val Val
        115                 120                 125

Val Ala Cys Glu Asn Gly Leu Pro Val His Leu Asp Gln Ser Ile Phe
    130                 135                 140

Arg Arg Pro
145

<210> SEQ ID NO 14
<211> LENGTH: 147
<212> TYPE: PRT
<213> ORGANISM: Gorilla gorilla

<400> SEQUENCE: 14

Met Val Met Gly Leu Gly Val Leu Leu Leu Val Phe Val Leu Gly Leu
1               5                   10                  15

Gly Leu Thr Pro Pro Thr Leu Ala Gln Asp Asn Ser Arg Tyr Thr His
            20                  25                  30

Phe Leu Thr Gln His Tyr Asp Ala Lys Pro Gln Gly Arg Asp His Arg
        35                  40                  45

Tyr Cys Glu Ser Ile Met Arg Arg Arg Gly Leu Thr Ser Pro Cys Lys
    50                  55                  60

Asp Ile Asn Thr Phe Ile His Gly Asn Lys Arg Ser Ile Lys Ala Ile
65                  70                  75                  80

Cys Glu Asn Lys Asn Gly Asn Pro His Arg Glu Asn Leu Arg Ile Ser
                85                  90                  95

Lys Ser Ser Phe Gln Val Thr Thr Cys Lys Leu His Gly Gly Ser Pro
            100                 105                 110

Trp Pro Pro Cys Gln Tyr Arg Ala Thr Ala Gly Phe Arg Asn Val Val
        115                 120                 125

Val Ala Cys Glu Asn Gly Leu Pro Val His Leu Asp Gln Ser Ile Phe
    130                 135                 140

Arg Arg Pro
145

<210> SEQ ID NO 15
<211> LENGTH: 147
<212> TYPE: PRT
<213> ORGANISM: Pan troglodytes

<400> SEQUENCE: 15

Met Val Met Gly Leu Gly Val Leu Leu Leu Val Phe Val Leu Gly Leu
1               5                   10                  15

Gly Leu Thr Pro Pro Thr Leu Ala Gln Asp Asn Ser Arg Tyr Thr His
            20                  25                  30

Phe Leu Thr Gln His Tyr Asp Ala Lys Pro Gln Gly Arg Asp Asp Arg
        35                  40                  45

Tyr Cys Glu Ser Ile Met Arg Arg Arg Gly Leu Thr Ser Pro Cys Lys
    50                  55                  60

Asp Ile Asn Thr Phe Ile His Gly Asn Lys Arg Ser Ile Lys Ala Ile
65                  70                  75                  80

Cys Glu Asn Lys Asn Gly Asn Pro His Arg Glu Asn Leu Arg Ile Ser
                85                  90                  95
```

Lys Ser Ser Phe Gln Val Thr Thr Cys Lys Leu His Gly Gly Ser Pro
                100                 105                 110

Trp Pro Pro Cys Gln Tyr Arg Ala Thr Ala Gly Phe Arg Asn Val Val
            115                 120                 125

Val Ala Cys Glu Asn Gly Leu Pro Val His Leu Asp Gln Ser Ile Phe
        130                 135                 140

Arg Arg Pro
145

<210> SEQ ID NO 16
<211> LENGTH: 146
<212> TYPE: PRT
<213> ORGANISM: Macaca mulatta

<400> SEQUENCE: 16

Met Val Met Gly Leu Gly Leu Phe Leu Leu Val Phe Met Leu Gly Leu
1               5                   10                  15

Gly Leu Thr Pro Pro Thr Leu Ala Gln Asp Asn Ser Arg Tyr Arg Asp
            20                  25                  30

Phe Leu Thr Lys His Tyr Asp Ala Thr Pro Gln Gly Arg Asn Asp Arg
        35                  40                  45

Tyr Cys Glu Ser Met Met Arg Arg Arg Gly Leu Thr Ser Pro Cys Lys
    50                  55                  60

Asp Ile Asn Thr Phe Ile His Gly Asn Ser Arg His Ile Lys Ala Ile
65                  70                  75                  80

Cys Gly Asp Glu Asn Gly Asn Pro Tyr Gly Glu Asn Leu Arg Ile Ser
                85                  90                  95

Lys Ser Pro Phe Gln Val Thr Thr Cys Asn Leu Arg Gly Gly Ser Ser
                100                 105                 110

Arg Pro Pro Cys Arg Tyr Arg Ala Thr Ala Gly Phe Arg Asn Ile Val
            115                 120                 125

Val Ala Cys Glu Asn Asp Leu Pro Val His Leu Asp Gln Ser Ile Phe
        130                 135                 140

Arg Pro
145

<210> SEQ ID NO 17
<211> LENGTH: 146
<212> TYPE: PRT
<213> ORGANISM: Equus caballus

<400> SEQUENCE: 17

Met Ala Met Ser Leu Cys Pro Leu Leu Leu Val Phe Val Leu Gly Leu
1               5                   10                  15

Gly Leu Thr Pro Pro Ser Leu Ala Gln Asp Asp Ser Arg Tyr Arg Gln
            20                  25                  30

Phe Leu Thr Lys His Tyr Asp Ala Asn Pro Arg Gly Arg Asn Asp Arg
        35                  40                  45

Tyr Cys Glu Ser Met Met Val Arg Arg His Leu Thr Pro Cys Lys
    50                  55                  60

Asp Thr Asn Thr Phe Ile His Gly Ser Lys Ser Ser Ile Lys Ala Ile
65                  70                  75                  80

Cys Gly Asn Lys Asn Gly Asn Pro Tyr Gly Glu Thr Leu Arg Ile Ser
                85                  90                  95

Lys Thr Arg Phe Gln Val Thr Cys Lys His Ala Gly Gly Ser Pro
                100                 105                 110

```
Arg Pro Pro Cys Arg Tyr Arg Ala Thr Pro Gly Phe Arg Ser Ile Val
        115                 120                 125

Ile Ala Cys Glu Asn Gly Leu Pro Val His Phe Asp Glu Ser Phe Phe
130                 135                 140

Arg Pro
145

<210> SEQ ID NO 18
<211> LENGTH: 147
<212> TYPE: PRT
<213> ORGANISM: Sus scrofa

<400> SEQUENCE: 18

Met Val Ile Leu Leu Gly Pro Leu Leu Leu Val Phe Met Leu Gly Leu
1               5                   10                  15

Gly Leu Ala Pro Leu Ser Leu Ala Lys Asp Glu Asp Arg Tyr Thr His
            20                  25                  30

Phe Leu Thr Gln His Tyr Asp Ala Lys Pro Lys Gly Arg Asp Gly Arg
        35                  40                  45

Tyr Cys Glu Ser Ile Met Lys Gln Arg Gly Leu Thr Arg Pro Cys Lys
    50                  55                  60

Glu Val Asn Thr Phe Ile His Gly Thr Arg Asn Asp Ile Lys Ala Ile
65                  70                  75                  80

Cys Asn Asp Lys Asn Gly Glu Pro Tyr Asn Asn Phe Arg Arg Ser Lys
                85                  90                  95

Ser Pro Phe Gln Ile Thr Thr Cys Lys His Lys Gly Gly Ser Asn Arg
            100                 105                 110

Pro Pro Cys Gly Tyr Arg Ala Thr Ala Gly Phe Arg Thr Ile Ala Val
        115                 120                 125

Ala Cys Glu Asn Gly Leu Pro Val His Phe Asp Glu Ser Phe Ile Ile
130                 135                 140

Thr Ser Gln
145

<210> SEQ ID NO 19
<211> LENGTH: 145
<212> TYPE: PRT
<213> ORGANISM: Rattus rattus

<400> SEQUENCE: 19

Met Glu Met Ser Leu Arg Pro Leu Leu Leu Val Phe Val Leu Gly Leu
1               5                   10                  15

Val Ser Thr Pro Ser Thr Leu Ala Gln Asp Asp Pro Arg Tyr Thr Lys
            20                  25                  30

Phe Leu Thr Gln His Tyr Asp Ala Lys Pro Lys Gly Arg Asp Ala Arg
        35                  40                  45

Tyr Cys Glu Ser Met Met Arg Arg Arg Gly Leu Thr Ser Pro Cys Lys
    50                  55                  60

Glu Val Asn Thr Phe Ile His Gly Asn Lys Gly Ser Ile Lys Ala Ile
65                  70                  75                  80

Cys Gly Ala Asn Gly Ser Pro Tyr Gly Glu Asn Leu Arg Ile Ser Gln
                85                  90                  95

Ser Pro Phe Gln Ile Thr Thr Cys Lys His Thr Gly Gly Ser Pro Arg
            100                 105                 110

Pro Pro Cys Arg Tyr Arg Ala Ser Ala Gly Phe Arg His Val Val Ile
        115                 120                 125
```

```
Ala Cys Glu Asn Gly Leu Pro Val His Phe Asp Glu Ser Phe Ile Ser
        130                 135                 140
Leu
145

<210> SEQ ID NO 20
<211> LENGTH: 145
<212> TYPE: PRT
<213> ORGANISM: Mus musculus

<400> SEQUENCE: 20

Met Ala Ile Ser Pro Gly Pro Leu Phe Leu Ile Phe Val Leu Gly Leu
1               5                   10                  15

Val Val Ile Pro Pro Thr Leu Ala Gln Asp Asp Ser Arg Tyr Thr Lys
                20                  25                  30

Phe Leu Thr Gln His His Asp Ala Lys Pro Lys Gly Arg Asp Asp Arg
            35                  40                  45

Tyr Cys Glu Arg Met Met Lys Arg Arg Ser Leu Thr Ser Pro Cys Lys
50                  55                  60

Asp Val Asn Thr Phe Ile His Gly Asn Lys Ser Asn Ile Lys Ala Ile
65                  70                  75                  80

Cys Gly Ala Asn Gly Ser Pro Tyr Arg Glu Asn Leu Arg Met Ser Lys
                85                  90                  95

Ser Pro Phe Gln Val Thr Thr Cys Lys His Thr Gly Gly Ser Pro Arg
            100                 105                 110

Pro Pro Cys Gln Tyr Arg Ala Ser Ala Gly Phe Arg His Val Val Ile
        115                 120                 125

Ala Cys Glu Asn Gly Leu Pro Val His Phe Asp Glu Ser Phe Phe Ser
    130                 135                 140
Leu
145

<210> SEQ ID NO 21
<211> LENGTH: 144
<212> TYPE: PRT
<213> ORGANISM: Gallus gallus

<400> SEQUENCE: 21

Met Thr Met Ser Pro Cys Pro Leu Leu Leu Val Phe Val Leu Gly Leu
1               5                   10                  15

Val Val Ile Pro Pro Thr Leu Ala Gln Asn Glu Gly Tyr Glu Lys Phe
                20                  25                  30

Leu Arg Gln His Tyr Asp Ala Lys Pro Lys Gly Arg Asp Asp Arg Tyr
            35                  40                  45

Cys Glu Ser Met Met Lys Glu Arg Lys Leu Thr Ser Pro Cys Lys Asp
50                  55                  60

Val Asn Thr Phe Ile His Gly Thr Lys Lys Asn Ile Arg Ala Ile Cys
65                  70                  75                  80

Gly Lys Lys Gly Ser Pro Tyr Gly Glu Asn Phe Arg Ile Ser Asn Ser
                85                  90                  95

Pro Phe Gln Ile Thr Thr Cys Thr His Ser Gly Ala Ser Pro Arg Pro
            100                 105                 110

Pro Cys Gly Tyr Arg Ala Phe Lys Asp Phe Arg Tyr Ile Val Ile Ala
        115                 120                 125

Cys Glu Asp Gly Trp Pro Val His Phe Asp Glu Ser Phe Ile Ser Pro
    130                 135                 140
```

<210> SEQ ID NO 22
<211> LENGTH: 378
<212> TYPE: DNA
<213> ORGANISM: Artificial Sequence
<220> FEATURE:
<223> OTHER INFORMATION: Modified Bos taurus sequence

<400> SEQUENCE: 22

| atgcaggacg | actaccgcta | catccacttt | ctcacccagc | actacgacgc | caagccaaag | 60 |
| ggccgcaacg | acgagtactg | cttcaacatg | atgaagaacc | gccgcctcac | ccgcccatgc | 120 |
| aaggaccgca | caccttcat  | ccacggcaac | aagaacgaca | tcaaggccat | ctgcgaggac | 180 |
| cgcaacggcc | agccatacag | gggcgacctc | cgcatctcca | agtccgagtt | ccagatcacc | 240 |
| atctgcaagc | acaagggcgg | ctcctcccgc | ccaccatgca | ggtacggcgc | caccgaggac | 300 |
| tcccgcgtga | tcgtggtggg | ctgcgagaac | ggcctcccag | tgcacttcga | cgagtccttc | 360 |
| atcaccccac | gccactga | | | | | 378 |

<210> SEQ ID NO 23
<211> LENGTH: 378
<212> TYPE: DNA
<213> ORGANISM: Artificial Sequence
<220> FEATURE:
<223> OTHER INFORMATION: Modified Bos taurus sequence

<400> SEQUENCE: 23

| atgcaggacg | actaccgtta | catccatttc | ttgactcagc | actacgacgc | taagcctaag | 60 |
| ggaagaaacg | atgagtactg | cttcaacatg | atgaagaaca | gaaggcttac | caggccttgc | 120 |
| aaggatagaa | cactttcat  | ccacggaaac | aagaacgaca | tcaaggctat | ctgcgaggat | 180 |
| agaaacggac | aaccttacag | aggtgatctc | aggatctcta | agtctgagtt | ccagatcact | 240 |
| atctgcaagc | acaagggtgg | aagctctaga | cctccttgta | gatacggtgc | tactgaggat | 300 |
| tctagagtta | tcgttgttgg | atgcgagaac | ggacttcctg | ttcatttcga | tgagtctttc | 360 |
| atcacccccta | ggcactaa | | | | | 378 |

<210> SEQ ID NO 24
<211> LENGTH: 912
<212> TYPE: DNA
<213> ORGANISM: Artificial Sequence
<220> FEATURE:
<223> OTHER INFORMATION: Fusion gene

<400> SEQUENCE: 24

| atggcggata | cagctagagg | aacccatcac | gatatcatcg | gcagagacca | gtacccgatg | 60 |
| atgggccgag | accgagacca | gtaccagatg | tccggacgag | gatctgacta | ctccaagtct | 120 |
| aggcagattg | ctaaagctgc | aactgctgtc | acagctggtg | gttccctcct | tgttctctcc | 180 |
| agccttaccc | ttgttggaac | tgtcatagct | ttgactgttg | caacacctct | gctcgttatc | 240 |
| ttcagcccaa | tccttgtccc | ggctctcatc | acagttgcac | tcctcatcac | cggttttctt | 300 |
| tcctctggag | ggtttggcat | tgccgctata | accgttttct | cttggattta | caagtacgca | 360 |
| acggagagc  | acccacaggg | atcagacaag | ttggacagtg | caaggatgaa | gttgggaagc | 420 |
| aaagctcagg | atctgaaaga | cagagctcag | tactacggac | agcaacatac | tggtggggaa | 480 |
| catgaccgtg | accgtactcg | tgtggccag  | cacactactc | ttgttcctcg | tggatctcag | 540 |
| gacgactacc | gttacatcca | tttcttgact | cagcactacg | acgctaagcc | taagggaaga | 600 |
| aacgatgagt | actgcttcaa | catgatgaag | aacagaaggc | ttaccaggcc | ttgcaaggat | 660 |

```
agaaacactt tcatccacgg aaacaagaac gacatcaagg ctatctgcga ggatagaaac    720
ggacaacctt acagaggtga tctcaggatc tctaagtctg agttccagat cactatctgc    780
aagcacaagg gtggaagctc tagacctcct tgtagatacg gtgctactga ggattctaga    840
gttatcgttg ttggatgcga gaacggactt cctgttcatt tcgatgagtc tttcatcacc    900
cctaggcact aa                                                          912
```

<210> SEQ ID NO 25
<211> LENGTH: 303
<212> TYPE: PRT
<213> ORGANISM: Artificial Sequence
<220> FEATURE:
<223> OTHER INFORMATION: Fusion protein

<400> SEQUENCE: 25

```
Met Ala Asp Thr Ala Arg Gly Thr His His Asp Ile Ile Gly Arg Asp
1               5                   10                  15

Gln Tyr Pro Met Met Gly Arg Asp Arg Asp Gln Tyr Gln Met Ser Gly
                20                  25                  30

Arg Gly Ser Asp Tyr Ser Lys Ser Arg Gln Ile Ala Lys Ala Ala Thr
            35                  40                  45

Ala Val Thr Ala Gly Gly Ser Leu Leu Val Leu Ser Ser Leu Thr Leu
        50                  55                  60

Val Gly Thr Val Ile Ala Leu Thr Val Ala Thr Pro Leu Leu Val Ile
65                  70                  75                  80

Phe Ser Pro Ile Leu Val Pro Ala Leu Ile Thr Val Ala Leu Leu Ile
                85                  90                  95

Thr Gly Phe Leu Ser Ser Gly Gly Phe Gly Ile Ala Ala Ile Thr Val
                100                 105                 110

Phe Ser Trp Ile Tyr Lys Tyr Ala Thr Gly Glu His Pro Gln Gly Ser
            115                 120                 125

Asp Lys Leu Asp Ser Ala Arg Met Lys Leu Gly Ser Lys Ala Gln Asp
        130                 135                 140

Leu Lys Asp Arg Ala Gln Tyr Tyr Gly Gln Gln His Thr Gly Gly Glu
145                 150                 155                 160

His Asp Arg Asp Arg Thr Arg Gly Gly Gln His Thr Thr Leu Val Pro
                165                 170                 175

Arg Gly Ser Gln Asp Asp Tyr Arg Tyr Ile His Phe Leu Thr Gln His
            180                 185                 190

Tyr Asp Ala Lys Pro Lys Gly Arg Asn Asp Glu Tyr Cys Phe Asn Met
        195                 200                 205

Met Lys Asn Arg Arg Leu Thr Arg Pro Cys Lys Asp Arg Asn Thr Phe
    210                 215                 220

Ile His Gly Asn Lys Asn Asp Ile Lys Ala Ile Cys Glu Asp Arg Asn
225                 230                 235                 240

Gly Gln Pro Tyr Arg Gly Asp Leu Arg Ile Ser Lys Ser Glu Phe Gln
                245                 250                 255

Ile Thr Ile Cys Lys His Lys Gly Gly Ser Ser Arg Pro Pro Cys Arg
            260                 265                 270

Tyr Gly Ala Thr Glu Asp Ser Arg Val Ile Val Val Gly Cys Glu Asn
        275                 280                 285

Gly Leu Pro Val His Phe Asp Glu Ser Phe Ile Thr Pro Arg His
    290                 295                 300
```

<210> SEQ ID NO 26
<211> LENGTH: 2396
<212> TYPE: DNA
<213> ORGANISM: Artificial Sequence
<220> FEATURE:
<223> OTHER INFORMATION: expression cassette

<400> SEQUENCE: 26

```
gaattcaaat ttattatgtg ttttttttcc gtggtcgaga ttgtgtatta ttctttagtt      60
attacaagac ttttagctaa aatttgaaag aatttacttt aagaaaatct taacatctga     120
gataatttca gcaatagatt atattttttca ttactctagc agtattttg cagatcaatc     180
gcaacatata tggttgttag aaaaaatgca ctatatatat atatattatt ttttcaatta     240
aaagagcatg atatataata tatatatata tatatatatg tgtgtgtgta tatggtcaaa     300
gaaattctta tacaaatata cacgaacaca tatatttgac aaaatcaaag tattacacta     360
aacaatgagt tggtgcatgg ccaaaacaaa tatgtagatt aaaaattcca gcctccaaaa     420
aaaaatccaa gtgttgtaaa gcattatata tatatagtag atcccaaatt tttgtacaat     480
tccacactga tcgaatttt aaagttgaat atctgacgta ggattttttt aatgtcttac     540
ctgaccattt actaataaca ttcatacgtt tcatttgaa atatcctcta taattatatt     600
gaatttggca cataataaga aacctaattg gtgatttatt ttactagtaa atttctggtg     660
atgggctttc tactagaaag ctctcggaaa atcttggacc aaatccatat tccatgactt     720
cgattgttaa ccctattagt tttcacaaac atactatcaa tatcattgca acggaaaagg     780
tacaagtaaa acattcaatc cgataggaa gtgatgtagg aggttgggaa gacaggccca     840
gaaagagatt tatctgactt gttttgtgta tagttttcaa tgttcataaa ggaagatgga     900
gacttgagaa gtttttttg gactttgttt agctttgttg ggcgttttt tttttttgatc     960
aataactttg ttgggcttat gatttgtaat attttcgtgg actctttagt ttatttagac    1020
gtgctaactt tgttgggctt atgacttgtt gtaacatatt gtaacagatg acttgatgtg    1080
cgactaatct ttacacatta aacatagttc tgttttttga agttcttat tttcattttt    1140
atttgaatgt tatatatttt tctatatttta taattctagt aaaaggcaaa ttttgctttt    1200
aaatgaaaaa aatatatatt ccacagtttc acctaatctt atgcatttag cagtacaaat    1260
tcaaaaattt cccatttta ttcatgaatc ataccattat atattaacta aatccaaggt    1320
aaaaaaaagg tatgaaagct ctatagtaag taaaatataa attccccata aggaaagggc    1380
caagtccacc aggcaagtaa aatgagcaag caccactcca ccatcacaca atttcactca    1440
tagataacga taagattcat ggaattatct tccacgtggc attattccag cggttcaagc    1500
cgataagggt ctcaacacct ctccttaggc ctttgtggcc gttaccaagt aaaattaacc    1560
tcacacatat ccacactcaa aatccaacgg tgtagatcct agtccacttg aatctcatgt    1620
atcctagacc ctccgatcac tccaaagctt gttctcattg ttgttatcat tatatataga    1680
tgaccaaagc actagaccaa acctcagtca cacaaagagt aaagaagaac aatgcaggac    1740
gactaccgtt acatccattt cttgactcag cactacgacg ctaagcctaa gggaagaaac    1800
gatgagtact gcttcaacat gatgaagaac agaaggctta ccaggccttg caaggataga    1860
aacactttca tccacggaaa caagaacgac atcaaggcta tctgcgagga tagaaacgga    1920
caaccttaca gaggtgatct caggatctct aagtctgagt tccagatcac tatctgcaag    1980
cacaagggtg gaagctctag acctccttgt agatacggtg ctactgagga ttctagagtt    2040
atcgttgttg gatgcgagaa cggacttcct gttcatttcg atgagtcttt catcacccct    2100
```

| | |
|---|---:|
| aggcacaagg atgagctcta aagaaggagt gcgtcgaagc agatcgttca acatttggc | 2160 |
| aataaagttt cttaagattg aatcctgttg ccggtcttgc gatgattatc atataatttc | 2220 |
| tgttgaatta cgttaagcat gtaataatta acatgtaatg catgacgtta tttatgagat | 2280 |
| gggtttttat gattagagtc ccgcaattat acatttaata cgcgatagaa aacaaaatat | 2340 |
| agcgcgcaaa ctaggataaa ttatcgcgcg cggtgtcatc tatgttacta gatcga | 2396 |

<210> SEQ ID NO 27
<211> LENGTH: 1290
<212> TYPE: DNA
<213> ORGANISM: Artificial Sequence
<220> FEATURE:
<223> OTHER INFORMATION: expression cassette

<400> SEQUENCE: 27

| | |
|---|---:|
| ggatccacgg gctcactggc ggatatagag ggctggaaag ctttcaatag ttgccttgcg | 60 |
| agaggggaaa gaacttgttc tgcgtgtgga cggttactat gctagttcaa ttaattgtac | 120 |
| caacaaaaca tatattttat tttgagaaac ggtgtacaaa tgtagacgtt cacatacaca | 180 |
| catgtacaac aacccctata aatgcacaca cgcacactct acgcctatgg gcatactttc | 240 |
| gagagagtga gccatcagat cttatgataa aatgtaaaat attttgcccg caccactcaa | 300 |
| gtcgcatctc agaaaatttg tactcaagaa acttttggct ttaaatgaaa ccaaaaacaa | 360 |
| gaaaagctgg aaaaaggttg tgtggcagcc agccaatgac atgaaggact gaaatttcca | 420 |
| gcacacacaa cgcatccgac ggccatgctt cttccactga tccggagaag ataaggaaac | 480 |
| gaggcaacca gagaacgtca gccaccccaa ccacatctgt accaaagaaa cgacgctaag | 540 |
| tgtctggcta tataccgt agtgacccgg caatggtggc ctcacctgta gccggcatcc | 600 |
| tcctctcctc cgataataca ataccatgca ggacgactac cgctacatcc actttctcac | 660 |
| ccagcactac gacgccaagc caagggccg caacgacgag tactgcttca acatgatgaa | 720 |
| gaaccgccgc ctcacccgcc catgcaagga ccgcaacacc ttcatccacg caacaagaa | 780 |
| cgacatcaag gccatctgcg aggaccgcaa cggccagcca tacaggggcg acctccgcat | 840 |
| ctccaagtcc gagttccaga tcaccatctg caagcacaag ggcggctcct cccgcccacc | 900 |
| atgcaggtac ggcgccaccg aggactcccg cgtgatcgtg gtgggctgcg agaacggcct | 960 |
| cccagtgcac ttcgacgagt ccttcatcac cccacgccac aaggatgagc tctgaagaag | 1020 |
| gagtgcgtcg aagcagatcg ttcaaacatt tggcaataaa gtttcttaag attgaatcct | 1080 |
| gttgccggtc ttgcgatgat tatcatataa tttctgttga attacgttaa gcatgtaata | 1140 |
| attaacatgt aatgcatgac gttatttatg agatgggttt ttatgattag agtcccgcaa | 1200 |
| ttatacattt aatacgcgat agaaaacaaa atatagcgcg caaactagga taaattatcg | 1260 |
| cgcgcggtgt catctatgtt actagatcga | 1290 |

<210> SEQ ID NO 28
<211> LENGTH: 2320
<212> TYPE: DNA
<213> ORGANISM: Artificial Sequence
<220> FEATURE:
<223> OTHER INFORMATION: Expression casette

<400> SEQUENCE: 28

| | |
|---|---:|
| ccgtggtcga gattgtgtat tattctttag ttattacaag acttttagct aaaatttgaa | 60 |
| agaatttact ttaagaaaat cttaacatct gagataattt cagcaataga ttatattttt | 120 |
| cattactcta gcagtatttt tgcagatcaa tcgcaacata tatggttgtt agaaaaaatg | 180 |

-continued

```
cactatatat atatatatta tttttttcaat taaaagtgca tgatatataa tatatatata      240
tatatatata tgtgtgtgtg tatatggtca aagaaattct tatacaaata tacacgaaca      300
catatatttg acaaaatcaa agtattacac taaacaatga gttggtgcat ggccaaaaca      360
aatatgtaga ttaaaaattc cagcctccaa aaaaaaatcc aagtgttgta aagcattata      420
tatatatagt agatcccaaa tttttgtaca attccacact gatcgaattt ttaaagttga      480
atatctgacg taggattttt ttaatgtctt acctgaccat ttactaataa cattcatacg      540
ttttcatttg aaatatcctc tataattata ttgaatttgg cacataataa gaaacctaat      600
tggtgattta ttttactagt aaatttctgg tgatgggctt tctactagaa agctctcgga      660
aaatcttgga ccaaatccat attccatgac ttcgattgtt aaccctatta gttttcacaa      720
acatactatc aatatcattg caacggaaaa ggtacaagta aaacattcaa tccgataggg      780
aagtgatgta ggaggttggg aagacaggcc cagaaagaga tttatctgac ttgttttgtg      840
tatagttttc aatgttcata aaggaagatg gagacttgag aagttttttt tggactttgt      900
ttagctttgt tgggcgtttt ttttttttga tcaataactt tgttgggctt atgatttgta      960
atattttcgt ggactcttta gtttatttag acgtgctaac tttgttgggc ttatgacttg     1020
ttgtaacata ttgtaacaga tgacttgatg tgcgactaat ctttacacat taaacatagt     1080 tctgttttttt gaaagttctt attttcattt ttatttgaat gttatatatt tttctatatt     1140
tataattcta gtaaaaggca aattttgctt ttaaatgaaa aaaatatata ttccacagtt     1200
tcacctaatc ttatgcattt agcagtacaa attcaaaaat ttcccatttt tattcatgaa     1260
tcataccatt atatattaac taaatccaag gtaaaaaaaa ggtatgaaag ctctatagta     1320
agtaaaatat aaattcccca taaggaaagg gccaagtcca ccaggcaagt aaaatgagca     1380
agcaccactc caccatcaca caatttcact catagataac gataagattc atggaattat     1440
cttccacgtg gcattattcc agcggttcaa gccgataagg gtctcaacac ctctccttag     1500
gcctttgtgg ccgttaccaa gtaaaattaa cctcacacat atccacactc aaaatccaac     1560
ggtgtagatc ctagtccact tgaatctcat gtatcctaga ccctccgatc actccaaagc     1620
ttgttctcat tgttgttatc attatatata gatgaccaaa gcactagacc aaacctcagt     1680
cacacaaaga gtaaagaagg atcctctaga atgcaagatg actacagata catccacttc     1740
ctgacccagc actacgatgc caaaccaaag ggccggaacg acgagtactg cttcaacatg     1800
atgaagaacc gacgcctgac cagaccttgc aaagaccgca acaccttcat ccacggcaac     1860
aagaacgaca tcaaggccat ctgtgaggac agaaatggac agccttacag aggcgatctc     1920
agaatcagca agtctgagtt ccagatcacc atctgcaagc ataaaggagg ttcctcccgg     1980
cctccatgcc ggtacggagc cacagaagac tccagagtca ttgttgtcgg ctgtgagaat     2040
ggcttgcccg tccactttga tgagtccttt atcactccac gccacaagga tgagctctag     2100
ctgcaggcat gcccgctgaa atcaccagtc tctctctaca aatctatctc tctctataat     2160
aatgtgtgag tagttcccag ataagggaat tagggttctt atagggtttc gctcatgtgt     2220
tgagcatata agaacccctt agtatgtatt tgtatttgta aaatacttct atcaataaaa     2280
tttctaattc ctaaaaccaa aatccagggg taccgagctc                           2320
```

<210> SEQ ID NO 29
<211> LENGTH: 2320
<212> TYPE: DNA
<213> ORGANISM: Artificial Sequence
<220> FEATURE:

<223> OTHER INFORMATION: Expression casette

<400> SEQUENCE: 29

```
ccgtggtcga gattgtgtat tattctttag ttattacaag acttttagct aaaatttgaa      60
agaatttact ttaagaaaat cttaacatct gagataattt cagcaataga ttatatttt     120
cattactcta gcagtatttt tgcagatcaa tcgcaacata tatggttgtt agaaaaaatg    180
cactatatat atatatatta tttttcaat taaaagtgca tgatatataa tatatatata    240
tatatatata tgtgtgtgtg tatatggtca aagaaattct tatacaaata tacacgaaca    300
catatatttg acaaaatcaa agtattacac taaacaatga gttggtgcat ggccaaaaca    360
aatatgtaga ttaaaaattc cagcctccaa aaaaaaatcc aagtgttgta aagcattata    420
tatatatagt agatcccaaa tttttgtaca attccacact gatcgaattt ttaaagttga    480
atatctgacg taggattttt ttaatgtctt acctgaccat ttactaataa cattcatacg    540
ttttcatttg aaatatcctc tataattata ttgaatttgg cacataataa gaaacctaat    600
tggtgattta ttttactagt aaatttctgg tgatgggctt tctactagaa agctctcgga    660
aaatcttgga ccaaatccat attccatgac ttcgattgtt aaccctatta gttttcacaa    720
acatactatc aatatcattg caacggaaaa ggtacaagta aaacattcaa tccgataggg    780
aagtgatgta ggaggttggg aagacaggcc cagaaagaga tttatctgac ttgttttgtg    840
tatagttttc aatgttcata aaggaagatg gagacttgag aagttttttt tggactttgt    900
ttagctttgt tgggcgtttt tttttttga tcaataactt tgttgggctt atgatttgta    960
atattttcgt ggactcttta gtttatttag acgtgctaac tttgttgggc ttatgacttg   1020
ttgtaacata ttgtaacaga tgacttgatg tgcgactaat cttacacat taaacatagt   1080
tctgtttttt gaaagttctt attttcattt ttatttgaat gttatatatt tttctatatt   1140
tataattcta gtaaaaggca aattttgctt ttaaatgaaa aaaatatata ttccacagtt   1200
tcacctaatc ttatgcattt agcagtacaa attcaaaaat ttcccatttt tattcatgaa   1260
tcataccatt atatattaac taaatccaag gtaaaaaaaa ggtatgaaag ctctatagta   1320
agtaaaatat aaaattcccca taaggaaagg gccaagtcca ccaggcaagt aaaatgagca   1380
agcaccactc caccatcaca caatttcact catagataac gataagattc atggaattat   1440
cttccacgtg gcattattcc agcggttcaa gccgataagg gtctcaacac ctctccttag   1500
gcctttgtgg ccgttaccaa gtaaaattaa cctcacacat atccacactc aaaatccaac   1560
ggtgtagatc ctagtccact tgaatctcat gtatcctaga ccctccgatc actccaaagc   1620
ttgttctcat tgttgttatc attatatata gatgaccaaa gcactagacc aaacctcagt   1680
cacacaaaga gtaaagaagg atcctctaga atgcaggacg actaccgcta catccacttt   1740
ctcacccagc actacgacgc caagccaaag ggccgcaacg acgagtactg cttcaacatg   1800
atgaagaacc gccgcctcac ccgcccatgc aaggaccgca acccttcat ccacggcaac    1860
aagaacgaca tcaaggccat ctgcgaggac cgcaacggcc agccatacag gggcgacctc   1920
cgcatctcca gtccgagtt ccagatcacc atctgcaagc acaagggcgg ctcctcccgc   1980
ccaccatgca gtacggcgc caccgaggac tcccgcgtga tcgtggtggg ctgcgagaac   2040
ggcctcccag tgcacttcga cgagtccttc atcaccccac gccacaagga tgagctctga   2100
ctgcaggcat gcccgctgaa atcaccagtc tctctctaca aatctatctc tctctataat   2160
aatgtgtgag tagttcccag ataagggaat tagggttctt atagggtttc gctcatgtgt   2220
tgagcatata agaaacccctt agtatgtatt tgtatttgta aaatacttct atcaataaaa   2280
```

<210> SEQ ID NO 30
<211> LENGTH: 1708
<212> TYPE: DNA
<213> ORGANISM: Artificial Sequence
<220> FEATURE:
<223> OTHER INFORMATION: Expression casette

<400> SEQUENCE: 30

```
atctgttcat ctaccttact agtctgcatg attagtttat tcgttatttt cgtagtcatg      60
atttatcaat tactcgtacg gattatttca tatggatatt tgcttatatt tccaacaatt     120
tacactgtcg agttttggcg cggctgctgg agttactctt agagtagttg gacttgagac     180
aaaagctaga atatcaatta tatataggag tgaggagtta ttctttcgaa agaactttaa     240
acggtagctg cacttagtcg tcgcaatgaa atacttgtcg tactaccatg ataattggta     300
atatgagagg gaatattaat tcctcagtga tttgaatttt gtgtgctcat gtgcagtcac     360
ccacgccatg catccgacga cgggcggcta taccaactct tgcactgatc cggagggata     420
aggcgccatg caaccaggga acgtcgtcca ccccttccac atcctgtatc aaattaagga     480
acgggcgctg agcctatgcc gagacatata taatgcggcg actcggacat ggaggggcct     540
caggcatagc ccagctagtt atctcattct ctccttagca ataatactta gcaccatggc     600
ccccgcggtg gaattcatgc aggacgacta ccgctacatc cactttctca cccagcacta     660
cgacgccaag ccaaagggcc gcaacgacga gtactgcttc aacatgatga agaaccgccg     720
cctcacccgc ccatgcaagg accgcaacac cttcatccac ggcaacaaga cgacatcaa     780
ggccatctgc gaggaccgca acggccagcc atacagggggc gacctccgca tctccaagtc     840
cgagttccag atcaccatct gcaagcacaa gggcggctcc tcccgcccac catgcaggta     900
cggcgccacc gaggactccc gcgtgatcgt ggtgggctgc gagaacggcc tcccagtgca     960
cttcgacgag tccttcatca ccccacgcca aaggatgag ctctgagaat tcaacaataa    1020
ttttctgagc ctagtatcca tgatcatgat atagtaaggg aaaaatcata tctataagtt    1080
tccgaactta gtgaaaaaaa acctgtaaaa gatatgcagt catatacaca tgtgaaatta    1140
ggtaggaaaa tatgataatc tcgtagatga ggaaaaaata ttgtacacca aactattgta    1200
agttacagta atgtaatgta aaaaaagttt ttaagttaca gaaggtacat accgcaaata    1260
atcatattat tttaccaaga tatttttttc tggagtattc ctttcaagta tctttatct    1320
ctagaatctt ctccaatcat gagtggcaac cgaaatggag ctcctgtgtt gctccccgtg    1380
tctcaccccct ttcggcccca ctgtcattgg gtggacctat tctcacggcg ctgtcctga    1440
gaaacaaaaa tagcagctga atgaagacac ggcgacacg caagccagca tctctcattg    1500
aacctgcgga gtgagatagc tctcgtggcg ctgctctact tgacgcgttt gtctcataca    1560
acagcgcatg gctccttcat gtcaggtcca tgatccacag atggtatgat tgggtttgga    1620
acattttttg ggtttgtgat atgtcgtaga tacaagggga aatgtctgaa gcatgcatgg    1680
atgggttccc tgctcatgta ctcaatgt                                       1708
```

<210> SEQ ID NO 31
<211> LENGTH: 1769
<212> TYPE: DNA
<213> ORGANISM: Artificial Sequence
<220> FEATURE:
<223> OTHER INFORMATION: Expression casette

<400> SEQUENCE: 31

```
attgggaagc tttcttcatc ggtgattgat tccttcaaag acttatgttt cttatcttgc    60
ttctgaggca agtattcagt taccagttac cacttatatt ctggactttc tgactgcatc   120
ctcattttc caacatttta aatttcacta ttggctgaat gcttcttctt tgaggaagaa   180
acaattcagg tggcagaaat gtatcaacca atgcatatat gcaaatgtac ctcttgttct   240
caaaacatct atcggatggt tccatttgct ttgtcatcca attagtgact actttatatt   300
attcactcct ctttattact attttcatgc gaggttgcca tgtacattat atttgtaagg   360
attgacgcta ttgagcgttt ttcttcaatt ttctttattt tagacatggg tatgaaatgt   420
gtgttagagt tgggttgaat gagatatacg ttcaagtgaa tggcataccg ttctcgagta   480
aggatgacct acccattctt gagacaaatg ttacatttta gtatcagagt aaaatgtgta   540
cctataactc aaattcgatt gacatgtatc cattcaacat aaaattaaac cagcctgcac   600
ctgcatccac atttcaagta ttttcaaacc gttcggctcc tatccaccgg gtgtaacaag   660
acggattccg aatttggaag attttgactc aaattcccaa tttatattga ccgtgactaa   720
atcaacttta acttctataa ttctgattaa gctcccaatt tgtattccca acggcattac   780
ctccaaaatt tatagactct catcccctt taaaccaact tagtaaacgt ttttttttt    840
aattttatga agttaagttt ttaccttgtt tttaaaaga atcgttcata agatgccatg   900
ccagaacatt agctacacgt tacacatagc atgcagccgc ggagaattgt ttttcttcgc   960
cacttgtcac tcccttcaaa cacctaagag cttctctctc acagcacaca catacaatca  1020
catgcgtgca tgcattatta cacgtgatcg ccatgcaaat ctcctttata gcctataaat  1080
taactcatcc gcttcactct ttactcaaac caaaactcat caatacaaac aagattaaaa  1140
acatacacca tgggcgaata tgcaggacga ctaccgttac atccatttct tgactcagca  1200
ctacgacgct aagcctaagg gaagaaacga tgagtactgc ttcaacatga tgaagaacag  1260
aaggcttacc aggccttgca aggatagaaa cactttcatc cacggaaaca agaacgacat  1320
caaggctatc tgcgaggata gaaacggaca accttacaga ggtgatctca ggatctctaa  1380
gtctgagttc cagatcacta tctgcaagca caagggtgga agctctagac tccttgtag   1440
atacggtgct actgaggatt ctagagttat cgttgttgga tgcgagaacg gacttcctgt  1500
tcatttcgat gagtctttca tcaccccag gcacaaggat gagctctaac tgcaggcatg  1560
cccgctgaaa tcaccagtct ctctctacaa atctatctct ctctataata atgtgtgagt  1620
agttcccaga taagggaatt agggttctta tagggtttcg ctcatgtgtt gagcatataa  1680
gaaacccta gtatgtattt gtatttgtaa aatacttcta tcaataaaat ttctaattcc  1740
taaaaccaaa atccagggggt accgagctc                                   1769
```

<210> SEQ ID NO 32
<211> LENGTH: 1810
<212> TYPE: DNA
<213> ORGANISM: Artificial Sequence
<220> FEATURE:
<223> OTHER INFORMATION: expression cassette

<400> SEQUENCE: 32

```
aagctttctt catcggtgat tgattccttt aaagacttat gtttcttatc ttgcttctga    60
ggcaagtatt cagttaccag ttaccactta tattctggac tttctgactg catcctcatt   120
tttccaaacat tttaaatttc actattggct gaatgcttct tctttgagga agaaacaatt   180
cagatggcag aaatgtatca accaatgcat atatacaaat gtacctcttg ttctcaaaac   240
```

```
atctatcgga tggttccatt tgctttgtca tccaattagt gactacttta tattattcac     300
tcctctttat tactattttc atgcgaggtt gccatgtaca ttatatttgt aaggattgac     360
gctattgagc gttttctcc aattttcttt attttagaca tgggtatgaa atgtgtgtta     420
gagttgggtt gaatgagata tacgttcaag tgaagtggca taccgttctc gagtaaggat     480
gacctaccca ttcttgagac aaatgttaca ttttagtatc agagtaaaat gtgtacctat     540
aactcaaatt cgattgacat gtatccattc aacataaaat taaaccagcc tgcacctgca     600
tccacatttc aagtatttc aaaccgttcg gctcctatcc accgggtgta acaagacgga     660
ttccgaattt ggaagatttt gactcaaatt cccaatttat attgaccgtg actaaatcaa     720
ctttaacttc tataattctg attaagctcc caatttatat tcccaacggc actacctcca     780
aaatttatag actctcatcc ccttttaaac caacttagta aacgtttttt ttttaatttt     840
tatgaagtta agttttacc ttgtttttaa aaagaatcgt tcataagatg ccatgccaga     900
acattagcta cacgttacac atagcatgca gccgcggaga attgttttc ttcgccactt     960 gtcactccct tcaaacacct aagagcttct ctctcacagc acacacatac aatcacatgc    1020
gtgcatgcat tattacacgt gatcgccatg caaatctcct ttatagccta taaattaact    1080
catccgcttc actctttact caaaccaaaa ctcatcaata caaacaagat taaaaacata    1140
cacgaatgca ggacgactac cgttacatcc atttcttgac tcagcactac gacgctaagc    1200
ctaagggaag aaacgatgag tactgcttca acatgatgaa gaacagaagg cttaccaggc    1260
cttgcaagga tagaaacact ttcatccacg gaaacaagaa cgacatcaag gctatctgcg    1320
aggatagaaa cggacaacct tacagaggtg atctcaggat ctctaagtct gagttccaga    1380
tcactatctg caagcacaag ggtggaagct ctagacctcc ttgtagatac ggtgctactg    1440
aggattctag agttatcgtt gttggatgcg agaacggact tcctgttcat ttcgatgagt    1500
ctttcatcac ccctaggcac aaggatgagc tctaaagaag gagtgcgtcg aagcagatcg    1560
ttcaaacatt tggcaataaa gtttcttaag attgaatcct gttgccggtc ttgcgatgat    1620
tatcatataa tttctgttga attacgttaa gcatgtaata attaacatgt aatgcatgac    1680
gttatttatg agatgggttt ttatgattag agtcccgcaa ttatacatttt aatacgcgat    1740 agaaaacaaa atatagcgcg caaactagga taaattatcg cgcgcggtgt catctatgtt    1800
actagatcga                                                           1810
```

<210> SEQ ID NO 33
<211> LENGTH: 1555
<212> TYPE: DNA
<213> ORGANISM: Artificial Sequence
<220> FEATURE:
<223> OTHER INFORMATION: Expression casette

<400> SEQUENCE: 33

```
gaattcttga caaactagtt agtccatgtg tttgtgttgt tcgtcaacca ccaaaattaa      60
ttataggaaa tggttaaccc tatttccctt tcacaactca actgtcgtgg tactccatta     120
cagcacttac gtacacgagt tctatgagag cagacctcca aaatgaatat ctgctaagtg     180
tttatctact tagatgaagg acgacaatca ctttcttggg aaatattagc gacacaactc     240
cttacttcct cctcttcttc ctagtgtttt tgttgtgat tgagtcgaca caacaacaac     300
actgcactat tacaaccagt acgactatat caactagcaa tgtcttcctt atatgttact     360
atttattttg ctaatattca ttatgtttaa atcacatgtg caccctttcta ttgacatcaa     420
```

```
aaaattagta tcaactttct agattaaaat gcaactaaaa gtacataaat ttctatcggt      480
ggggatcgag tgattcttta aaccgattat tacacaagtt aaccacacta aaattaacat      540
tggtgaatcg tgccatgatt tttttctagt gcaaaatagc caaaccaagc aaaacatatg      600
tggctatcgt tacacatgtg taaaggtatt gcatcacacc attgtcaccc atgtatttgg      660
acaataccga gaggaaaaac cacttattta ttgtatttta tcaagtttat cttgcttacg      720
tataaattat aacccaacaa agtaatcact aaatgtcaaa accaactaga taccatgtca      780
tctctacctt atcttactaa tattcttttt gcaaaatcga aaattaatct tgcacaagca      840
caaggactga gatgtgtata aatatctctt agattagcta gctaatatat cgcacatatt      900
attgagacca actagcaata tagaaagcac aatattgtac caataatgca ggacgactac      960
cgctacatcc actttctcac ccagcactac gacgccaagc caagggccg caacgacgag     1020 tactgcttca acatgatgaa gaaccgccgc ctcacccgcc catgcaagga ccgcaacacc     1080
ttcatccacg gcaacaagaa cgacatcaag gccatctgcg aggaccgcaa cggccagcca     1140 tacagggggcg acctccgcat ctccaagtcc gagttccaga tcaccatctg caagcacaag     1200
ggcggctcct cccgcccacc atgcaggtac ggcgccaccg aggactcccg cgtgatcgtg     1260
gtgggctgcg agaacggcct cccagtgcac ttcgacgagt ccttcatcac ccacgccac     1320 aaggatgagc tctgactgca ggcatgcccg ctgaaatcac cagtctctct ctacaaatct     1380
atctctctct ataataatgt gtgagtagtt cccagataag ggaattaggg ttcttatagg     1440
gtttcgctca tgtgttgagc atataagaaa cccttagtat gtatttgtat ttgtaaaata     1500
cttctatcaa taaatttctc aattcctaaa accaaaatcc aggggtaccg agctc         1555
```

<210> SEQ ID NO 34
<211> LENGTH: 1610
<212> TYPE: DNA
<213> ORGANISM: Artificial Sequence
<220> FEATURE:
<223> OTHER INFORMATION: expression cassette

<400> SEQUENCE: 34

```
gaattcttga caaactagtt agtccatgtg tttgtgttgt tcgtcaacca ccaaaattaa       60
ttataggaaa tggttaaccc tatttcctt tcacaactca actgtcgtgg tactccatta      120
cagcacttac gtacacgagt tctatgagag cagacctcca aaatgaatat ctgctaagtg      180
tttatctact tagatgaagg acgacaatca ctttcttggg aaatattagc gacacaactc      240
cttacttcct cctcttcttc ctagtgtttt tgttgtgat tgagtcgaca caacaacaac      300
actgcactat tacaaccagt acgactatat caactagcaa tgtcttcctt atatgttact      360
atttattttg ctaatattca ttatgtttaa atcacatgtg cacctttcta ttgacatcaa      420
aaaattagta tcaactttct agattaaaat gcaactaaaa gtacataaat ttctatcggt      480
ggggatcgag tgattcttta aaccgattat tacacaagtt aaccacacta aaattaacat      540
tggtgaatcg tgccatgatt tttttctagt gcaaaatagc caaaccaagc aaaacatatg      600
tggctatcgt tacacatgtg taaaggtatt gcatcacacc attgtcaccc atgtatttgg      660
acaataccga gaggaaaaac cacttattta ttgtatttta tcaagtttat cttgcttacg      720
tataaattat aacccaacaa agtaatcact aaatgtcaaa accaactaga taccatgtca      780
tctctacctt atcttactaa tattcttttt gcaaaatcga aaattaatct tgcacaagca      840
caaggactga gatgtgtata aatatctctt agattagcta gctaatatat cgcacatatt      900
attgagacca actagcaata tagaaagcac aatattgtac caataatgca ggacgactac      960
```

```
cgctacatcc actttctcac ccagcactac gacgccaagc caaagggccg caacgacgag    1020
tactgcttca acatgatgaa gaaccgccgc ctcacccgcc catgcaagga ccgcaacacc    1080
ttcatccacg gcaacaagaa cgacatcaag gccatctgcg aggaccgcaa cggccagcca    1140
tacaggggcg acctccgcat ctccaagtcc gagttccaga tcaccatctg caagcacaag    1200
ggcggctcct cccgcccacc atgcaggtac ggcgccaccg aggactcccg cgtgatcgtg    1260
gtgggctgcg agaacggcct cccagtgcac ttcgacgagt ccttcatcac ccacgccac     1320 aaggatgagc tctgaagaag gagtgcgtcg aagcagatcg ttcaaacatt tggcaataaa    1380
gtttcttaag attgaatcct gttgccggtc ttgcgatgat tatcatataa tttctgttga    1440
attacgttaa gcatgtaata attaacatgt aatgcatgac gttatttatg agatgggttt    1500
ttatgattag agtcccgcaa ttatacattt aatacgcgat agaaaacaaa atatagcgcg    1560
caaactagga taaattatcg cgcgcggtgt catctatgtt actagatcga             1610
```

<210> SEQ ID NO 35
<211> LENGTH: 3472
<212> TYPE: DNA
<213> ORGANISM: Artificial Sequence
<220> FEATURE:
<223> OTHER INFORMATION: expression cassette

<400> SEQUENCE: 35

```
cactcaaaac gagaaaactc attgacacgt gattaattaa gtattaatct ctatatcttc      60
tctactatta taaaaactga agaagtattt gtcagtaatt tggtacatca tccgtgtatg     120
agttggtttt taaattcgtt cgcttttgta aatacagaag gtgtcgtata agaaatatat     180
ttaaaaaact cgcatgctaa cttgagacga tcggacttct aactgcagct tatgattttc     240
taaaaaaaaa tatgttcttt ttttgcgagg aaaaagatat atgttcaagt gaattctcag     300
ggagaatttc actttagcta aaccatataa caataataat attaaaatag tctttacccg     360
ttacaacgca cgggcatttt tctagtcatt tgaaaatttt aaaaatatgt ttattcaaat     420
agatctaaga acttctaaaa catatttgga catgcaaaca atctcaagtg aaaggtcatt     480
aacttcaaag ttgtagattt cgtcgagctc tacaattttg atataaagtt ggttttcatc     540
caacaacctc atatgagaaa gtggtttcta aaaaaatatg cacatatgat atgagtaggt     600
ccatttctaa aggcacacct ctcaaaataa aattttagag gtgatcgctt aaggcaaccg     660
cctctagaat tgaggaggca attaagacga tcgcctctaa aaatctattt tataggtgat     720
tttctaatgc agttacatag accattcatc actagaaatc aggctatttt taaagttgat     780
ctgtttatat ggctgcctct aaaaatcaat gtctagtggt tgtccatgac tgcgggtcca     840
ttatatacgt tggttttctt ataaactata tgtacagtaa caatcacgat aatttaatat     900
atgtggtctc ttagtttatg tgtgtgtacg gtgtgtgtat ttatttgttt ctttgcatct     960
ccataatcat ggttatttg aatggtttgt ttttcaggct accgtgttcc tgcttccctc    1020
gcttaatgct tatgtgtcct gccagttgca ttatcacgga taactgatca tatgccattt    1080
tatggcttca gtcataatat attgttttac taagtttgtc tacatgataa agagatacac    1140
atggatctct cctaaataaa gtcatcattg atgtccacat gcattattat gtatgttaat    1200
ttacaagtga taaaacacat actactacta cacccaagat gtggtatagc tcaaacacac    1260
cccaacgtag taattttctct agtgagagaa caatcatata tagcaaaata tcctattgag    1320
cctggcgata ataactcata gtaataattt tattatgtaa gaagtttgtt tttagttatc    1380
```

```
acacacactg ggtgcatctt aatgctatat atttatttgg ccacacaaaa gtagttcttc    1440
ctctaatgcc tttcattctc aactttcatc atttatttgt cctttttgtt aggttccgtc    1500
aacctaatat gggtgaaaag acagttttct attaatatgt tttaatgcaa gatctgtgat    1560
ttttatattt tctttttgagt tacaattttt atactagctt attatgcatg atggtcgaat    1620
atctctcatg aaccataata ttattttagt aatcaagtgt gatgcaaaat cctttaaatt    1680
tagtatatta cataaaaaaa taattctcaa tttctacttc ttagcttata ggctgtgcgc    1740
atatagaatt tgaattttag aagttttaaa gttgattttg gtttttttatc atatttattt    1800 ttagcactga cttttgaata gctaaaattg aaaaacttat cgtaaaaaat attattattg    1860
gttgcttcgt ttattctgga tgcatcttaa catttactgt aaaaatataa cctatggttt    1920
acttatattt aatcaacaat atttattgtt aaaaagtaat agacaagaga aaaacaatct    1980
tttcttccat ctattaacat tatgttaatg gacaactaac ggaaagggca ataagatat     2040 caaatttaag ataagtgta taagagggga agccaatttt gtgagaataa ataaggaacc     2100
gatcaagtct agaggacaca taagaatttt tctcatcatg gtgttcatat aactagcccg    2160
ttgaactgtg agattgaata cttttgggat agtgaaagaa tatttgactt aatattttc     2220 ttgaacacta caatctgcta tttgtttcac atataaaaaa gtgaatattg catcctcaat    2280
aaatgatcta acataaggta cataaatatc taaatctttc tctattaatg tgtcatacat    2340
ggatgcatat atcttagtaa atatctaaat cttttctctat taatgtgtgg attcatacat    2400
ggatgcatat atcttcaata agtgagtagt aaatatctaa atctttctct attaatgtgt    2460
ggattcatac atggatgcat atatcttcaa taaatgagta gcaaatgttt aaatcttttc    2520
tttattaatg tgtgggttca acatgcatgg atgcatatat cttaaataaa tgagccaatt    2580
aaatatgagg tgcacaaata tccaaatctt tgcatgcata ggctctctct tcaccattga    2640
ttttacatcc aatggataca attcgagcaa catgtcaact tttcccctcg atggccttat    2700
ataaacccaa ctatccccaa ctagaagata cacaccacaa caatatagcc actgtatgat    2760
atcaagaaaa aggtctatcc tagctgcttt atactaaagc aatagccatg caggacgact    2820
accgctacat ccactttctc acccagcact acgacgccaa gccaaagggc cgcaacgacg    2880
agtactgctt caacatgatg aagaaccgcc gcctcacccg cccatgcaag gaccgcaaca    2940
ccttcatcca cggcaacaag aacgacatca aggccatctg cgaggaccgc aacgccagc     3000 catacagggg cgacctccgc atctccaagt ccgagttcca gatcaccatc tgcaagcaca    3060
agggcggctc ctcccgccca ccatgcaggt acggcgccac cgaggactcc cgcgtgatcg    3120
tggtgggctg cgagaacggc ctcccagtgc acttcgacga gtccttcatc accccacgcc    3180
acaaggatga gctctgaaga aggagtgcgt cgaagcagat cgttcaaaca tttggcaata    3240
aagtttctta agattgaatc ctgttgccgg tcttgcgatg attatcatat aatttctgtt    3300
gaattacgtt aagcatgtaa taattaacat gtaatgcatg acgttattta tgagatgggt    3360
ttttatgatt agagtcccgc aattatacat ttaatacgcg atagaaaaca aaatatagcg    3420
cgcaaactag gataaattat cgcgcgcggt gtcatctatg ttactagatc ga            3472
```

<210> SEQ ID NO 36
<211> LENGTH: 1917
<212> TYPE: DNA
<213> ORGANISM: Artificial Sequence
<220> FEATURE:
<223> OTHER INFORMATION: expression cassette

<400> SEQUENCE: 36

```
gcatgcaaat atgcaacata atttcctttt tacttggcta attatatttg ataaatattt     60
cacagatata caataatcaa acacaataaa tcatatgtgt ttttagtttt agttctcata    120
tccaaatata caatagctaa ccaaatctca tcgggaagtt agccatgccg aggtaggttg    180
ttgccggaat gtttttagtt ttagttctca tacaaccaaa tctcattcaa atatataaaa    240
cattccggca acaacttgtg gcgtacatct agttacaagg gaatattagt gatggcgtga    300
gcaagcgata aggccaagga gagaagaagt gcatcgtcta cggaggccag ggaaagacaa    360
tggacatgca gagaggcagg ggcggggaag aaacacttgg agatcataga agaagataag    420
aggttaaaca taggaggagg atataatgga caattaaatc tgcgttagtt gaactcattt    480
gggaagtaaa caaattttct attctgtgta aaccaaacta tttgacgcgg attttctctg    540
aagatcctat attaatttta gacatggttt ggctagttca tttgtcgtga aaaggtgttt    600
ccataagtcc aaaattctac aactttttt gtatggcacg tcatagcata gatagatgtt    660
gtgagtcact ggatagatat tgtgagtcat agcatggatt cgtgttgctg gaaatccaac    720
tacatgacaa gcaacaaaac ctgaaatggg ctttaggagt taacaattta cttgttccat    780
gcaggctacc ttccactact cgacatgctt agaagctttg agtggccgta gatttgcaaa    840
agcaatggct aacagacaca tattctgcca aaccccaaga aggataatca cttttcttag    900
ataaaaaaga acagaccaat atacaaacat ccacacttct gcaaacaata catcagaact    960
aggattacgc cgattacgtg gctttagcag actgtccaaa aatctgtttt gcaaagctcc   1020
aattgctcct tgcttatcca gcttcttttg tgttggcaaa ctgcgctttt ccaaccgatt   1080
ttgttcttct cgcgctttct tcttaggcta acaaacctc accgtgcacg cagccatggt   1140
cctgaacctt cacctcgtcc ctataaaagc ctagccaacc ttcacaatct tatcatcacc   1200
cacaacaccg agcaccacaa actagagatc aattcactga tagtccaccg agatgcagga   1260
cgactaccgc tacatccact ttctcaccca gcactacgac gccaagccaa agggccgcaa   1320
cgacgagtac tgcttcaaca tgatgaagaa ccgccgcctc acccgcccat gcaaggaccg   1380
caacaccttc atccacggca acaagaacga catcaaggcc atctgcgagg accgcaacgg   1440
ccagccatac aggggcgacc tccgcatctc caagtccgag ttccagatca ccatctgcaa   1500
gcacaagggc ggctcctccc gcccaccatg caggtacggc gccaccgagg actcccgcgt   1560
gatcgtggtg ggctgcgaga acggcctccc agtgcacttc gacgagtcct tcatcacccc   1620
acgccacaag gatgagctct gaagaaggag tgcgtcgaag cagatcgttc aaacatttgg   1680
caataaagtt tcttaagatt gaatcctgtt gccggtcttg cgatgattat catataattt   1740
ctgttgaatt acgttaagca tgtaataatt aacatgtaat gcatgacgtt atttatgaga   1800
tgggttttta tgattagagt cccgcaatta tacatttaat acgcgataga aaacaaaata   1860
tagcgcgcaa actaggataa attatcgcgc gcggtgtcat ctatgttact agatcga      1917
```

<210> SEQ ID NO 37
<211> LENGTH: 1666
<212> TYPE: DNA
<213> ORGANISM: Artificial Sequence
<220> FEATURE:
<223> OTHER INFORMATION: Expression casette

<400> SEQUENCE: 37

```
ttatagagag agatagattt gtagagagag actggtgatt tcagcgtgtc ctctccaaat     60
gaaatgaact tccttatata gaggaagggt cttgcgaagg atagtgggat tgtgcgtcat    120
```

```
cccttacgtc agtggagata tcacatcaat ccacttgctt tgaagacgtg gttggaacgt    180
cttctttttc cacgatgctc ctcgtgggtg ggggtccatc tttgggacca ctgtcggcag    240
aggcatcttg aacgatagcc tttcctttat cgcaatgatg gcatttgtag gtgccacctt    300
ccttttctac tgtcttcatg atgaagtgac agatagctgg gcaatggaat ccgaggaggt    360
ttcccgaaat tacccttttgt tggaaagtct caattgccct ttggtcttct gagactgtat    420
ccttgatatt tttggagtag accagagtgt cgtgctccac catgttgacg aagattttct    480
tcttgtcatt gagtcgtaag agactctgta tgaactgttc gccagttttc acggcgagtt    540
ctgttagatc ctcgatttga atctttgact ccatggcctt tgattcagta ggaactactt    600
ttttagagac tccaatctct attacttgcc ttggtttatg aagcaagcct tgaatcgtcc    660
atactggaat agtacttctg atcttgagaa atatatcttt ctctgtgttc ttgatgcagt    720
tagtcctgaa tcttttgact gcatctttaa ccttcttggg aaggtatttg atctcctgga    780
gattattact cgggtagatc gtcttaatga gacctgctgc gtaggcctct ctaaccatct    840
gtgggttagc gttcttctg aaattgaaga ggctaatctt ctcattatca gtggtgaaca    900
tagtatcgtc accttcaccg tcgaactttc ttcctagatc gtagagatag aggaagtcgt    960
ccattgtaat ctccggggca aaggagatcc atggctactc aacgaagggc aaaccctagc   1020
tctctccatc taattactgt attctctctg ctcgtcgctg tcgtctccgc tcaggacgac   1080
taccgttaca tccatttctt gactcagcac tacgacgcta agcctaaggg aagaaacgat   1140
gagtactgct tcaacatgat gaagaacaga aggcttacca ggccttgcaa ggatagaaac   1200
actttcatcc acggaaacaa gaacgacatc aaggctatct gcgaggatag aaacggacaa   1260
ccttacagag gtgatctcag gatctctaag tctgagttcc agatcactat ctgcaagcac   1320
aagggtggaa gctctagacc tccttgtaga tacggtgcta ctgaggattc tagagttatc   1380
gttgttggat gcgagaacgg acttcctgtt catttcgatg agtctttcat cacccctagg   1440
cactaactgc aggcatgccc gctgaaatca ccagtctctc tctacaaatc tatctctctc   1500
tataataatg tgtgagtagt tcccagataa gggaattagg gttcttatag ggtttcgctc   1560
atgtgttgag catataagaa acccttagta tgtatttgta tttgtaaaat acttctatca   1620
ataaaatttc taattcctaa aaccaaaatc caggggtacc gagctc                  1666
```

<210> SEQ ID NO 38
<211> LENGTH: 2551
<212> TYPE: DNA
<213> ORGANISM: Artificial Sequence
<220> FEATURE:
<223> OTHER INFORMATION: Expression casette

<400> SEQUENCE: 38

```
gaattcctac aatgttgaat aaacgtaggt agtggctact taatttcttc gatttcttaa     60
gtgcttagta ctttttcaaca ttaaaaatgt tgttaccaag tctaaatttt cttcacaact    120
tgtaactaaa cttttcatta tgtgtaatcg taaaggatta gcgctacaaa tagatggtga    180
ttcccttcta atggacgagt tgacattgac gcattatgtc tctggttagc tagtccgacg    240
tttgaacaag tactcttacc gctctcgaaa caaaattaaa accaaaattt tatagatcta    300
ttagtaaaat ctactattgt taattttatc acatagtcca tgtgtgtgtt aatattaagg    360
atgaagtcaa tgtatatata tatatcaaat ctctattcct actagatatg gaatcaccct    420
acttgtataa atggcaaact cattcaacga gctacacacg acttttccaa cttatttcag    480
tgtttgagat cattttaatg caacaactat atgttaaagg gaaattggtc tagaagcggc    540
```

```
tatttcttgg tcttgaaatc atattgttct tctatagtgt agtgacattt cctataatta      600
atttgaaaaa aggaagaaat tgtgttggca atgaaaacat catatgtatg gtgtgaagta      660
tatacaaaaa aaaaatccca ttcgtgaatg aaaactacgg tgtatatatg tgaaagacat      720
atatggagcc ttcactatac ggtgtagttc atttacataa gaatggttgg aaatggagat      780
gccatatttt ttttattttt tttttccaca atggagatgc catatctata aaaaaagaaa      840
agaggttgaa ctagttgggt cggcgcgacg aaaagagaaa atacaacttg ctgggctaaa      900
tctagaaatt tccatttctg taaatgcctt aaattaatgg ctcttattta tcaaatacgg      960
gacaaaccct ctttacacct tacaagttac gggtataggg tgtttattct cccgtacccg     1020
ttcaaactac actatataat aaaccattga cattgtagac ctattacaca tcctgcagtt     1080
attggcttat tgcgatcttt attaaatcca aagatacata ctatatcgaa gaaacaaaaa     1140
gtcaagaaat aataaaacga aaataaatga aggcatcaat aaaagcttac cgctcacatg     1200
tttattttct aataactaat ttttatttaa aaagcagttt atacatctac caaatttatt     1260
tcttagcata aatatatatt tgggttttga cttttaagtt ctttctgact tctgagtgat     1320
aatcaccagt ttgcaactta tatttgccta aaccgcatgc caattgtcat gtatcgtatc     1380
tagtaatggt attaatgacg aggatcccaa aatttaaatt ccactttcca agcattgagc     1440
tctttaaaca attcatggtc aacttaatta caaggaaaaa aaagaactta ttgttatagt     1500
ggaacagcta ttttttttgga tattaaaaga ataataacag caaaacagaa ttatcgtgtc     1560
ctaataatac ctaaggtcct aaacgaagca aaaaagttgg taaataagga agagaaaacc     1620
tacaagatat taaaacggtg tcgttgttcg gaagaatata ccgaagtagc aaaaggaata     1680
tctcattaga gagtccctta taaatgaccg ttttaataca cttcaactct gtccttgttc     1740
ataggcagct tcaacgatca ttccacttcc ttcttcctct ctctcaacat tttcccctga     1800
aaataaggaa actaaagatt cttcctctct ctttctacac tcttctgaca atactaaaac     1860
actttatcag atcagatggc tactcaacga agggcaaacc ctagctctct ccatctaatt     1920
actgtattct ctctgctcgt cgctgtcgtc tccgctcagg acgactaccg ttacatccat     1980
ttcttgactc agcactacga cgctaagcct aaggaagaa acgatgagta ctgcttcaac      2040
atgatgaaga acagaaggct taccaggcct tgcaaggata gaaacacttt catccacgga     2100
aacaagaacg acatcaaggc tatctgcgag gatagaaacg gacaaccttca cagaggtgat     2160 ctcaggatct ctaagtctga gttccagatc actatctgca agcacaaggg tggaagctct     2220
agacctcctt gtagatacgg tgctactgag gattctagag ttatcgttgt tggatgcgag     2280
aacggacttc ctgttcattt cgatgagtct ttcatcaccc ctaggcacta actgcaggca     2340
tgcccgctga aatcaccagt ctctctctac aaatctatct ctctctataa taatgtgtga     2400
gtagttccca gataagggaa ttagggttct tatagggttt cgctcatgtg ttgagcatat     2460
aagaaaccct tagtatgtat ttgtatttgt aaaaatacttc tatcaataaa atttctaatt     2520
cctaaaacca aaatccaggg gtaccgagct c                                     2551
```

<210> SEQ ID NO 39
<211> LENGTH: 1555
<212> TYPE: DNA
<213> ORGANISM: Artificial Sequence
<220> FEATURE:
<223> OTHER INFORMATION: Expression casette

<400> SEQUENCE: 39

| | |
|---|---|
| attgttttca tagaagtttg tcgaaaacat cgttttttcag taaaaaaatc ataaagcact | 60 |
| gaaatatcga ttgacatact tttaacaaga aaactaacaa tagggcccgg tcgtcaggcc | 120 |
| tacgtggcac caggtgacag cccgcagaga caatgtttgt ctggtccatt aaaaagaaaa | 180 |
| gaaggcccac ctgtcagctg cccagcccac tagcagtcat cttcaacctt ctgccagaag | 240 |
| gaaaaagttg agtcgcgtgc acagagaagc tgccacctcc ggcctgcctg atcccaagc | 300 |
| ctcattccct tcgccagtga tgctgcataa acctgctccg ccaatccccg tcgctcacag | 360 |
| attccctctc acagtcttac tctcctgctc gaatccccat cttagtccac agcatgccgt | 420 |
| cggcgtcttc cttcgcccgt gcgactacta gcctcccctc cccgtgagc atccccacc | 480 |
| agaggatttg gatcgaggca tcctgtagga agcgcaagtc gttatggtgc tcgcctctga | 540 |
| ccatcggtcc ctcgctccga ttcatcgatg ttgctaatcc acgacgcctc ctctcgctat | 600 |
| cacacacaac gcgttggcct tgccaagcct ctgatgtcgt gcgtgacaag cctcgcaact | 660 |
| ccatgctttg tcgccaacac cgtctgctcc ggccaccgcc gtcaacataa aggacgacac | 720 |
| tcccaggcat ccccggctgg cccgaccaga cgaacgtgcc caaggtgagc agccggttct | 780 |
| tccctctcta cttccttctc catttgcacc ctccggagag cctccgatga cgaccgtgcc | 840 |
| tcggccgcca ctctgctccg ccacgagctc gatgtgggca tggctactca acgaagggca | 900 |
| aaccctagct ctctccatct aattactgta ttctctctgc tcgtcgctgt cgtctccgct | 960 |
| caggacgact accgctacat ccactttctc acccagcact acgacgccaa gccaaagggc | 1020 |
| cgcaacgacg agtactgctt caacatgatg aagaaccgcc gcctcacccg cccatgcaag | 1080 |
| gaccgcaaca ccttcatcca cggcaacaag aacgacatca aggccatctg cgaggaccgc | 1140 |
| aacggccagc catacagggg cgacctccgc atctccaagt ccgagttcca gatcaccatc | 1200 |
| tgcaagcaca agggcggctc ctcccgccca ccatgcaggt acgcgccac cgaggactcc | 1260 |
| cgcgtgatcg tggtgggctg cgagaacggc ctcccagtgc acttcgacga gtccttcatc | 1320 |
| accccacgcc actgactgca ggcatgcccc tgaaatcac cagtctctct ctacaaatct | 1380 |
| atctctctct ataataatgt gtgagtagtt cccagataag ggaattaggg ttcttatagg | 1440 |
| gtttcgctca tgtgttgagc atataagaaa cccttagtat gtatttgtat ttgtaaaata | 1500 |
| cttctatcaa taaaatttct aattcctaaa accaaaatcc aggggtaccg agctc | 1555 |

<210> SEQ ID NO 40
<211> LENGTH: 1991
<212> TYPE: DNA
<213> ORGANISM: Artificial Sequence
<220> FEATURE:
<223> OTHER INFORMATION: Expression casette

<400> SEQUENCE: 40

| | |
|---|---|
| cccaacctcg gtcttggtca caccaggaac tctctggtaa gctagctcca ctccccagaa | 60 |
| acaaccggcg ccaaattgcg cgaattgctg acctgaagac ggaacatcat cgtcgggtcc | 120 |
| ttgggcgatt gcggcggaag atgggtcagc ttgggcttga ggacgagacc cgaatccgag | 180 |
| tctgttgaaa aggttgttca ttggggattt gtatacggag attggtcgtc gagaggtttg | 240 |
| agggaaagga caaatgggtt tggctctgga gaaagagagt gcggctttag agagagaatt | 300 |
| gagaggttta gagagagatg cggcggcgat gagcggagga gagacgacga ggacctgcat | 360 |
| tatcaaagca gtgacgtggt gaaatttgga acttttaaga ggcagataga tttattattt | 420 |
| gtatccattt tcttcattgt tctagaatgt cgcggaacaa atttaaaac taaatcctaa | 480 |
| attttttctaa ttttgttgcc aatagtggat atgtgggccg tatagaagga atctattgaa | 540 |

```
ggcccaaacc catactgacg agcccaaagg ttcgttttgc gttttatgtt tcggttcgat      600
gccaacgcca cattctgagc taggcaaaaa acaaacgtgt ctttgaatag actcctctcg      660
ttaacacatg cagcggctgc atggtgacgc cattaacacg tggcctacaa ttgcatgatg      720
tctccattga cacgtgactt ctcgtctcct ttcttaatat atctaacaaa cactcctacc      780
tcttccaaaa tatatacaca tcttttgat caatctctca ttcaaaatct cattctctct       840
agtaaacaag aacaaaaaaa tggcggatac agctagagga acccatcacg atatcatcgg      900
cagagaccag tacccgatga tgggccgaga ccgagaccag taccagatgt ccggacgagg      960
atctgactac tccaagtcta ggcagattgc taaagctgca actgctgtca cagctggtgg     1020
ttccctcctt gttctctcca gccttaccct tgttggaact gtcatagctt tgactgttgc     1080
aacacctctg ctcgttatct tcagcccaat ccttgtcccg gctctcatca cagttgcact     1140
cctcatcacc ggttttcttt cctctggagg gtttggcatt gccgctataa ccgttttctc     1200
ttggatttac aagtacgcaa cgggagagca cccacaggga tcagacaagt tggacagtgc     1260
aaggatgaag ttgggaagca agctcagga tctgaaagac agagctcagt actacggaca      1320
gcaacatact ggtggggaac atgaccgtga ccgtactcgt ggtggccagc acactactct     1380
tgttcctcgt ggatctcagg acgactaccg ttacatccat ttcttgactc agcactacga     1440
cgctaagcct aagggaagaa acgatgagta ctgcttcaac atgatgaaga acagaaggct     1500
taccaggcct tgcaaggata gaaacacttt catccacgga aacaagaacg acatcaaggc     1560
tatctgcgag gatagaaacg gacaacctta cagaggtgat ctcaggatct ctaagtctga     1620
gttccagatc actatctgca agcacaaggg tggaagctct agacctcctt gtagatacgg     1680
tgctactgag gattctagag ttatcgttgt tggatgcgag aacggacttc ctgttcattt     1740
cgatgagtct ttcatcaccc ctaggcacta actgcaggca tgcccgctga atcaccagt      1800 ctctctctac aaatctatct ctctctataa taatgtgtga gtagttccca gataagggaa     1860
ttagggttct tatagggttt cgctcatgtg ttgagcatat aagaaaccct tagtatgtat     1920
ttgtatttgt aaaatacttc tatcaataaa atttctaatt cctaaaacca aaatccaggg     1980
gtaccgagct c                                                          1991
```

<210> SEQ ID NO 41
<211> LENGTH: 891
<212> TYPE: DNA
<213> ORGANISM: Artificial Sequence
<220> FEATURE:
<223> OTHER INFORMATION: Expression casette

<400> SEQUENCE: 41

```
gctcccccgc cgtcgttcaa tgagaatgga taagaggctc gtgggattga cgtgaggggg       60
cagggatggc tatatttctg ggagcgaact ccggcgaat acgaagcgct tggatacaat       120
gcaggacgac taccgttaca tccatttctt gactcagcac tacgacgcta agcctaaggg      180
aagaaacgat gagtactgct tcaacatgat gaagaacaga aggcttacca ggccttgcaa      240
ggatagaaac actttcatcc acggaaacaa gaacgacatc aaggctatct gcgaggatag      300
aaacggacaa ccttacagag gtgatctcag gatctctaag tctgagttcc agatcactat      360
ctgcaagcac aagggtggaa gctctagacc tccttgtaga tacggtgcta ctgaggattc      420
tagagttatc gttgttggat gcgagaacgg acttcctgtt catttcgatg agtctttcat      480
cacccctagg cactaagatc ctggcctagt ctataggagg ttttgaaaag aaggagcaa      540
```

```
taatcatttt cttgttctat caagagggtg ctattgctcc tttctttttt tctttttatt    600
tatttactag tattttactt acatagactt ttttgtttac attatagaaa aagaaggaga    660
ggttattttc ttgcatttat tcatgattga gtattctatt ttgattttgt atttgtttaa    720
aattgtagaa atagaacttg tttctcttct tgctaatgtt actatatctt tttgattttt    780
tttttccaaa aaaaaaatca aattttgact tcttcttatc tcttatcttt gaatatctct    840
tatctttgaa ataataatat cattgaaata agaaagaaga gctatattcg a             891
```

<210> SEQ ID NO 42
<211> LENGTH: 125
<212> TYPE: PRT
<213> ORGANISM: Artificial Sequence
<220> FEATURE:
<223> OTHER INFORMATION: Gel protein sequence

<400> SEQUENCE: 42

```
Ala Gln Asp Asp Tyr Arg Tyr Ile His Phe Leu Thr Gln His Tyr Asp
1               5                   10                  15

Ala Lys Pro Lys Gly Arg Asn Asp Glu Tyr Cys Phe Asn Met Met Lys
            20                  25                  30

Asn Arg Arg Leu Thr Arg Pro Cys Lys Asp Arg Asn Thr Phe Ile His
        35                  40                  45

Gly Asn Lys Asn Asp Ile Lys Ala Ile Cys Glu Asp Arg Asn Gly Gln
    50                  55                  60

Pro Tyr Arg Gly Asp Leu Arg Ile Ser Lys Ser Glu Phe Gln Ile Thr
65                  70                  75                  80

Ile Cys Lys His Lys Gly Gly Ser Ser Arg Pro Pro Cys Arg Tyr Gly
                85                  90                  95

Ala Thr Glu Asp Ser Arg Val Ile Val Val Gly Cys Asn Gly Leu
            100                 105                 110

Pro Val His Phe Asp Glu Ser Phe Ile Thr Pro Arg His
        115                 120                 125
```

<210> SEQ ID NO 43
<211> LENGTH: 9
<212> TYPE: PRT
<213> ORGANISM: Bos taurus

<400> SEQUENCE: 43

```
Arg Asn Gly Gln Pro Tyr Arg Gly Asp
1               5
```

<210> SEQ ID NO 44
<211> LENGTH: 24
<212> TYPE: PRT
<213> ORGANISM: Bos taurus

<400> SEQUENCE: 44

```
Met Val Met Val Leu Ser Pro Leu Phe Leu Val Phe Ile Leu Gly Leu
1               5                   10                  15

Gly Leu Thr Pro Val Ala Pro Ala
            20
```

<210> SEQ ID NO 45
<211> LENGTH: 21
<212> TYPE: DNA
<213> ORGANISM: Artificial Sequence
<220> FEATURE:
<223> OTHER INFORMATION: primer sequence

<400> SEQUENCE: 45
gaacgacatc aaggctatct g                                                21

<210> SEQ ID NO 46
<211> LENGTH: 20
<212> TYPE: DNA
<213> ORGANISM: Artificial Sequence
<220> FEATURE:
<223> OTHER INFORMATION: primer sequence

<400> SEQUENCE: 46
agcaccgtat ctacaaggag                                                  20

<210> SEQ ID NO 47
<211> LENGTH: 19
<212> TYPE: DNA
<213> ORGANISM: Artificial Sequence
<220> FEATURE:
<223> OTHER INFORMATION: primer sequence

<400> SEQUENCE: 47
ccctcccaca tgctattct                                                   19

<210> SEQ ID NO 48
<211> LENGTH: 19
<212> TYPE: DNA
<213> ORGANISM: Artificial Sequence
<220> FEATURE:
<223> OTHER INFORMATION: primer sequence

<400> SEQUENCE: 48
agagcctcca atccagaca                                                   19

<210> SEQ ID NO 49
<211> LENGTH: 52
<212> TYPE: DNA
<213> ORGANISM: Artificial Sequence
<220> FEATURE:
<223> OTHER INFORMATION: primer sequence
<220> FEATURE:
<221> NAME/KEY: misc_feature
<222> LOCATION: (52)..(52)
<223> OTHER INFORMATION: n is a, c, g, or t

<400> SEQUENCE: 49
ttctagaatt cagcggccgc ttttttttttt tttttttttt tttttttttt rn             52

<210> SEQ ID NO 50
<211> LENGTH: 21
<212> TYPE: DNA
<213> ORGANISM: Artificial Sequence
<220> FEATURE:
<223> OTHER INFORMATION: primer sequence

<400> SEQUENCE: 50
ttctagaatt cagcggccgc t                                                21

<210> SEQ ID NO 51
<211> LENGTH: 4
<212> TYPE: PRT
<213> ORGANISM: Artificial Sequence
<220> FEATURE:
<223> OTHER INFORMATION: ER Retention Signal

<400> SEQUENCE: 51

Lys Asp Glu Leu

```
1

<210> SEQ ID NO 52
<211> LENGTH: 375
<212> TYPE: DNA
<213> ORGANISM: Artificial Sequence
<220> FEATURE:
<223> OTHER INFORMATION: modified Bos Taurus

<400> SEQUENCE: 52
caagatgact acagatacat ccacttcctg acccagcact acgatgccaa accaaagggc      60
cggaacgacg agtactgctt caacatgatg aagaaccgac gcctgaccag accttgcaaa     120
gaccgcaaca ccttcatcca cggcaacaag aacgacatca aggccatctg tgaggacaga     180
aatggacagc cttacagagg cgatctcaga atcagcaagt ctgagttcca gatcaccatc     240
tgcaagcata aaggaggttc ctcccggcct ccatgccggt acggagccac agaagactcc     300
agagtcattg ttgtcggctg tgagaatggc ttgcccgtcc actttgatga gtcctttatc     360
actccacgcc actag                                                      375

<210> SEQ ID NO 53
<211> LENGTH: 4
<212> TYPE: PRT
<213> ORGANISM: Artificial Sequence
<220> FEATURE:
<223> OTHER INFORMATION: Vacuole N-Terminal Target Signal

<400> SEQUENCE: 53

Asn Pro Ile Arg
1
```

The claims defining the invention are as follows:

1. A plant cell, wherein the plant cell is part of a monocotyledon or a dicotyledon plant callus, plant, seed or other plant part, said plant cell containing a nucleic acid encoding an angiogenin, wherein said nucleic acid encoding an angiogenin comprises:
   (a) an N-terminal plant signal sequence that when expressed as the N-terminus of an angiogenin protein drives angiogenin accumulation in the plant cell to a sub-cellular component selected from mitochondria, chloroplast, nucleus and nucleolus, and
   (b) a nucleotide sequence encoding a functional angiogenin protein, optimized for expression in a monocotyledon or a dicotyledon plant cell said monocotyledon optimized nucleotide sequence selected from the group consisting of:
   (i) SEQ ID NO: 22, and
   (ii) variants of SEQ ID NO: 22 having at least 98% sequence identity to the full length of SEQ ID NO: 22; and
   said dicotyledon optimized nucleotide sequence selected from the group consisting of:
   (iii) SEQ ID NO: 23, and
   (iv) variants of SEQ ID NO: 23, having at least 98% sequence identity to the full length of SEQ ID NO: 23,
   wherein said nucleic acid provides for a production of angiogenin protein at a level of between approximately 5 and 30% (weight/volume) of the total soluble protein of said plant cell,
   wherein said monocotyledon is selected from the group consisting of forage grasses, sorghum, sugarcane, corn, oat, wheat, rice, and barley, and
   wherein said dicotyledon is selected from the group consisting of forage legumes, soybean, lupin, peas, lentils, chickpeas, canola, vegetable brassicas, lettuce, spinach, bananas, citrus, strawberries, apples, oil palm, linseed, cottonseed, and safflower.

2. The plant cell of claim 1, wherein the sequence encoding a functional angiogenin is SEQ ID NO: 22 or 23.

3. The plant cell of claim 2, wherein the N-terminal signal is selected from one or more of the 4-amino-acid sequence NTPP (SEQ ID NO: 53), an N-terminal MTS, a nucleotide sequence encoding oleosin or an N-terminal NLS or NOS.

4. An artificial construct comprising a nucleic acid encoding an angiogenin and a promoter, operatively linked to the nucleic acid encoding an angiogenin,
   wherein the promoter is effective for enabling expression of the nucleic acid encoding an angiogenin in a monocotyledon or dicotyledon plant cell; and wherein said nucleic acid encoding an angiogenin comprises (a) an N-terminal plant signal sequence that when expressed as the N-terminus of an angiogenin protein drives angiogenin accumulation in the plant cell to a sub-cellular component selected from mitochondria, chloroplast, nucleus and nucleolus, and (b) a nucleotide sequence encoding a functional angiogenin protein optimized for expression in a monocotyledon or a dicotyledon plant cell said monocotyledon optimized nucleotide sequence selected from the group consisting of:

(i) SEQ ID NO: 22, and (ii) variants of SEQ ID NO: 22 having at least 98% sequence identity to the full length of SEQ ID NO: 22; and said dicotyledon optimized nucleotide sequence selected from the group consisting of:
(iii) SEQ ID NO: 23, and
(iv) variants of SEQ ID NO: 23, having at least 98% sequence identity to the full length of SEQ ID NO: 23,
wherein said nucleic acid provides for a production of angiogenin protein at a level of between approximately 5% and 30% (weight/volume) of the total soluble protein of a transfected plant cell,
wherein said monocotyledon is selected from the group consisting of forage grasses, sorghum, sugarcane, corn, oat, wheat, rice, and barley, and
wherein said dicotyledon is selected from the group consisting of forage legumes, soybean, lupin, peas, lentils, chickpeas, canola, vegetable brassicas, lettuce, spinach, bananas, citrus, strawberries, apples, oil palm, linseed, cottonseed, and safflower.

5. The artificial construct according to claim 4, wherein the sequence encoding a functional angiogenin is SEQ ID NO: 22 or 23.

6. The artificial construct of claim 5, wherein the N-terminal signal is selected from one or more of the 4-amino-acid sequence NTPP (SEQ ID NO: 53), an N-terminal MTS, a nucleotide sequence encoding oleosin or an N-terminal NLS or NOS.

7. A plant cell according to claim 1, wherein said monocotyledon is a forage grass selected from the group consisting of perennial ryegrass, tall fescue, Italian ryegrass, *brachiaria*, and *paspalum*.

8. An artificial construct according to claim 4, wherein said monocotyledon is a forage grass selected from the group consisting of perennial ryegrass, tall fescue, Italian ryegrass, *brachiaria*, and *paspalum*.

9. A plant cell according to claim 1, wherein said dicotyledon is a forage legume selected from the group consisting of white clover, red clover, subterranean clover, and alfalfa.

10. An artificial construct according to claim 4, wherein said dicotyledon is forage legume selected from the group consisting of white clover, red clover, subterranean clover, and alfalfa.

* * * * *